United States Patent
Meerpoel et al.

(10) Patent No.: US 9,975,899 B2
(45) Date of Patent: *May 22, 2018

(54) ANTIFUNGAL 5,6-DIHYDRO-4H-PYRROLO[1,2-A][1,4]BENZO-DIAZEPINES AND 6H-PYRROLO[1,2-A][1,4]BENZODIAZEPINES SUBSTITUTED WITH HETEROCYCLIC DERIVATIVES

(71) Applicant: JANSSEN PHARMACEUTICA NV, Beerse (BE)

(72) Inventors: Lieven Meerpoel, Turnhoutseweg (BE); Louis Jules Roger Marie Maes, Prinsstraat (BE); Kelly de Wit, Merksem (BE); Koen Jan Ludovicus Augustyns, Prinsstraat (BE)

(73) Assignee: Janssen Pharmaceutica NV, Beerse (BE)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/342,646

(22) Filed: Nov. 3, 2016

(65) Prior Publication Data
US 2017/0073348 A1 Mar. 16, 2017

Related U.S. Application Data

(63) Continuation of application No. 14/113,356, filed as application No. PCT/EP2012/058142 on May 3, 2012, now Pat. No. 9,493,468.

(30) Foreign Application Priority Data

May 5, 2011 (EP) ..................... 11164960

(51) Int. Cl.
| | | |
|---|---|---|
| A61K 31/551 | (2006.01) | |
| C07D 487/04 | (2006.01) | |
| A61K 9/28 | (2006.01) | |
| A61K 9/48 | (2006.01) | |

(52) U.S. Cl.
CPC .......... *C07D 487/04* (2013.01); *A61K 9/2866* (2013.01); *A61K 9/4866* (2013.01)

(58) Field of Classification Search
CPC ............................ A61K 31/551; C07D 487/04
USPC .......................................... 514/220; 540/561
See application file for complete search history.

(56) References Cited

U.S. PATENT DOCUMENTS 4,775,671 A 10/1988 Hunkeler et al.
4,959,361 A 9/1990 Walser
5,693,795 A 12/1997 Bender et al.

FOREIGN PATENT DOCUMENTS

| CN | 85101490 A | 1/1987 |
|---|---|---|
| CN | 1034722 A | 8/1989 |
| CN | 1150152 A | 5/1997 |
| WO | WO 02/34752 A1 | 5/2002 |

OTHER PUBLICATIONS

National Center for Biotechnology Information, PubChem Compound Database: CID=53213469, http://pubchem.ncbi.nim.nih.gov/compound/53213469 (create date Jun. 21, 2011).*
National Center for Biotechnology Information, PubChem Compound Database: CID=12297971, http://pubchem.ncbi.nim.nih.gov/compound/12297971 (create date Feb. 7, 2007).*
Butin, A., et al., "Furan Ring Opening-Pyrrole Ring Closure: A New Synthetic Route to Aryl(heteroaryl)-annylated Pyrrolo[1,2-α][1,4]Diazepines", Organic & Biomedical Chemistry, vol. 8, pp. 3316-3327 (2010).
Cheeseman, G., et al., "Synthesis of 5,6-Dihydro-4H-pyrrolo[1,3-α][1,4] Benzodiazepines", J. Heterocyclic Chemistry, vol. 16, pp. 241-144 (2979).
Cheeseman, G., et al, "Further Cyclisation Reactions of 1-Ayrlpyrroles", J. Chemical Society, pp. 2732-2734 (1971).
Meerpoel, L, et al, {"Pyrrolo[1,2-60 ][1,4]Benzodiazpine: A Novel Class of Non-Azole Anti-Dermatophyte Anti-Fungal Agents", Bioorganic & Medicinal Chemistry Letters, vol. 15, pp. 3453-3458 (2005).
Raines, S., et al., "Mannich Reactions. Synthesis of 4,5-Dihydropyrrolo[1,2-60 ]Quinoxalines, 2,3,4,5-Tetrahydro-1 H-prrolo] 1,2-60 ] [1.4] Diazepines and 5,6-Dihydro-4H-prrolo[1,2-60 ] [1.4] Benzodiazepines", J. Heterocyclic Chemistry, vol. 13, pp. 711-716 (1976).
Trinka, P., et al., "A Convenient Synthesis of Ethyl (2-Amin-5,6-dichlorobenzyl)glycinate", J. Prakt. Chem., vol. 338, pp. 675-678 (1996).
European Search Report for Application No. EP10192321 dated Mar. 2, 2011.

(Continued)

*Primary Examiner* — Brenda L Coleman
(74) *Attorney, Agent, or Firm* — Thomas J. Dodd

(57) ABSTRACT

The present invention is concerned with novel antifungal 5,6-dihydro-4H-pyrrolo-[1,2-a][1,4]benzodiazepines and 6H-pyrrolo[1,2-a][1,4]benzodiazepines substituted with heterocyclic derivatives of Formula (I)

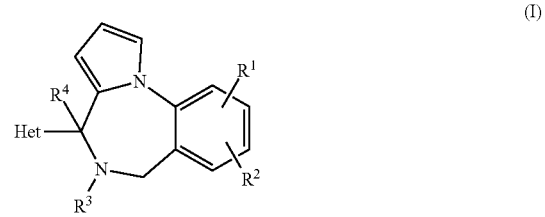

wherein $R^1$, $R^2$, $R^3$, $R^4$ and Het have the meaning defined in the claims. The compounds according to the present invention are active mainly against dermatophytes and systemic fungal infections. The invention further relates to processes for preparing such novel compounds, pharmaceutical compositions comprising said compounds as an active ingredient as well as the use of said compounds as a medicament.

8 Claims, No Drawings

(56) References Cited

OTHER PUBLICATIONS

International Search Report for Application No. PCT/EP2011/070458 dated May 23, 2013.
International Search Report for Application No. PCTE2011/073215 dated Jun. 25, 2013.
European Search Report for Application No. EP10196201 dated Mar. 4, 2011.
European Search Report dated Aug. 8, 2011 for Application No. EP11164960.
International Search Report dated Nov. 5, 2013 for Application No. PCT/EP2012/058142.
You, et al., Pharmacochemistry, Medicinal Chemistry, 2014, pp. 32-34, 1st edition (see English translation as provided).
RN 1281941-80-7, Database Registry [Online], Apr. 18, 2011, Retrieved from STN.
RN 739314-23-9, Database Registry [Online], Sep. 3, 2004, Retrieved from STN.

\* cited by examiner

ANTIFUNGAL 5,6-DIHYDRO-4H-PYRROLO[1,2-A][1,4]BENZO-DIAZEPINES AND 6H-PYRROLO[1,2-A][1,4]BENZODIAZEPINES SUBSTITUTED WITH HETEROCYCLIC DERIVATIVES

CROSS-REFERENCE TO RELATED APPLICATIONS

This application is a continuation of U.S. application Ser. No. 14/113,356 filed on May 3, 2012, which claims priority of the benefits of the filing of Application Nos. EP 11164960.4 filed May 5, 2011, and PCT/EP2012/058142 (WO2012/150305) filed May 3, 2012. The complete disclosures of the aforementioned related patent applications are hereby incorporated herein by reference for all purposes.

FIELD OF THE INVENTION

The present invention is concerned with novel antifungal 5,6-dihydro-4H-pyrrolo-[1,2-a][1,4] benzodiazepines and 6H-pyrrolo[1,2-a][1,4]benzodiazepines, both substituted with heterocyclic derivatives, active mainly against dermatophytes and systemic fungal infections. The invention further relates to processes for preparing such novel compounds, pharmaceutical compositions comprising said compounds as an active ingredient as well as the use of said compounds as a medicament.

BACKGROUND OF THE INVENTION

Dermatophyte is a common label for a group of 3 types of fungi that commonly causes skin disease in animals and humans. These anamorphic (asexual or imperfect fungi) genera are: *Microsporum, Epidermophyton* and *Trichophyton*. There are about 40 species in these 3 genera.

Dermatophytes cause infections of the skin, hair and nails due to their ability to obtain nutrients from keratinized material. The organisms colonize the keratin tissues and inflammation is caused by host response to metabolic by-products. They are usually restricted to the cornified layer of the epidermis because of their inability to penetrate viable tissue of an immunocompetent host. However, occasionally the organisms do invade subcutaneous tissues, resulting in kerion development. Invasion does elicit a host response ranging from mild to severe. Acid proteinases, elastase, keratinases, and other proteinases reportedly act as virulence factors.

Systemic fungal infections (SFI) are life-threatening conditions that most commonly affect patients with reduced immunity often resulting from therapeutic interventions to treat malignant diseases. The number of SFI's in modern hospitals keeps increasing, and the number of different fungi that have been involved in SFI is large and still growing. Despite many cases of invasive candidiasis and aspergillosis there has been an increased incidence of infections due to other molds like *Scedosporium apiospermum, Fusarium* spp., and *Zygomycetes, Rhizopus* and *Mucor* spp. Effective therapeutic agents treating all these infections very well therefore need to have very broad spectrum of activity. In the past few decades itraconazole, fluconazole, ketoconazole, and intravenous or liposomal amphotericin B have been used in SFI, and all of these agents have their limitations with regard to spectrum, safety or ease of administration. More recently a third generation of azoles have been investigated and introduced to the market, improving the treatment options in intensive care units. Voriconazole (Vfend™) and posaconazole (Noxafil™) show much improvement of treatment towards life threatening invasive SFI such as candidiasis, aspergillosis, and infections due to *Fusarium* species at clinical relevant dosages. Moreover posaconazole shows efficacy against infections caused by the emerging *Zygomycetes* spp. Echinocandins, such as anidulafungin, caspofungin, and micafungin, which are non-competitive inhibitors of 1,3-β-glucan synthesis in fungal cell walls, display high efficacy against *Candida* spp. and *Aspergillus* spp., but no activity against *Cryptococcus, Fusarium*, or *Zygomycetes* spp. Of all antimycotic agents, azoles still represent a unique class of compounds displaying the broadest antifungal spectrum via inhibition of 14-α-demethylase, an enzyme being essential for ergosterol biosynthesis in fungi.

Onychomycosis is the most common disease of the nails and constitutes about a half of all nail abnormalities. The prevalence of onychomycosis is about 6-8% in the adult population. The causative pathogens of onychomycosis include dermatophytes, *Candida*, and non-dermatophytic moulds. Dermatophytes are the fungi most commonly responsible for onychomycosis in the temperate western countries; meanwhile, *Candida* and non-dermatophytic moulds are more frequently involved in the tropics and subtropics. *Trichophyton rubrum* is the most common dermathophyte involved in onychomycosis. Other dermatophytes that may be involved are *Trichophyton interdigitale, Epidermophyton floccosum, Trichophyton violaceum, Microsporum gypseum, Trichophyton tonsurans, Trichophyton soudanense* and *Trichophyton verrucosum*. Other causative pathogens include *Candida* and non-dermatophytic moulds, in particular members of the mould generation *Scytalidium* (also *Neoscytalidium*), *Scopulariopsis*, and *Aspergillus*. 5,6-Dihydro-4H-pyrrolo[1,2-a][1,4]benzodiazepines have been described in J. Chem. Soc.(C), 2732-2734 (1971); J. Heterocyclic Chem., 13, 711-716 (1976); and J. Heterocyclic Chem., 16, 241-244 (1979). The compounds disclosed in these references all have a phenyl moiety in the 4-position and no biological activities were reported in any of these references.

A new synthetic route to aryl(heteroaryl)-annulated pyrrolo[1,2-a][1,4]diazepines has been described in Org. Biomol. Chem., 8, 3316-3327 (2010).

WO02/34752 describes 4-substituted 5,6-dihydro-4H-pyrrolo[1,2-a][1,4]benzo-diazepines as a new class of antifungal compounds. However, WO02/34752 only discloses compounds with a phenyl moiety in the 4-position.

The PhD thesis of De Wit K. describes the implementation of an in vitro and in vivo mycological evaluation platform and activity profiling of antifungal pyrrolobenzodiazepines (PhD Thesis; University of Antwerp, Belgium; Faculty of Pharmaceutical, Biomedical and Veterinary Sciences; Department of Biomedical Sciences; 2011; 220 p.).

The antifungal compounds of the present invention or part of the compounds of the present invention are structurally different and may have improved potency, improved metabolic stability properties, improved solubility, improved plasma binding, reduced hERG channel inhibition, reduced cytochrome P450 liabilities, or improved bioavailability compared with compounds disclosed in the prior art. Preferably said compounds have a broad antifungal spectrum, and maintain adequately high thereapeutic efficacy and adequately low toxicity or other side effects.

The compounds of the present invention are useful as squalene epoxidase inhibitors.

It is accordingly an object of the present invention to provide novel compounds with antifungal activity to overcome or ameliorate at least one of the disadvantages of the prior art, or to provide useful alternative compounds.

SUMMARY OF THE INVENTION

It has been found that the compounds of the present invention are useful as antifungal compounds.

The present invention concerns novel compounds of Formula (I):

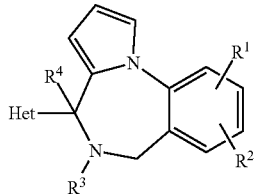

(I)

and stereoisomeric forms thereof, wherein
$R^1$ is hydrogen, halo, $C_{1-4}$alkyl or $C_{1-4}$alkyloxy;
$R^2$ is hydrogen, halo, $C_{1-4}$alkyl or $C_{1-4}$alkyloxy;
$R^3$ and $R^4$ are hydrogen;
or $R^3$ and $R^4$ taken together form a bond;
Het is a monocyclic or bicyclic heterocyclic radical selected from

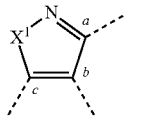

(d-1)

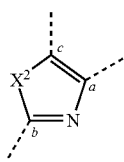

(d-2)

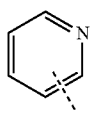

(d-3)

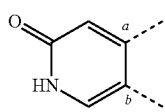

(d-4)

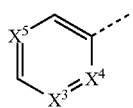

(d-5)

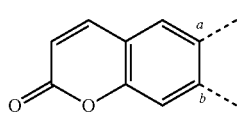

(d-6)

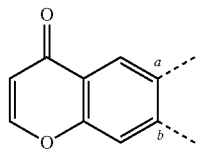

(d-7)

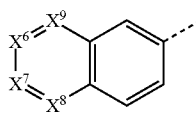

(d-8)

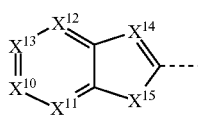

(d-9)

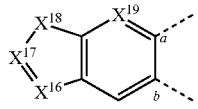

(d-10)

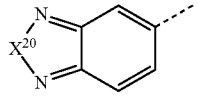

(d-11)

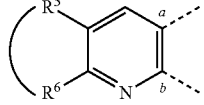

(d-12)

(d-1) and (d-2) are attached to the remainder of the molecule with a bond in position a, b or c;
(d-4), (d-6), (d-7), (d-10) and (d-12) are attached to the remainder of the molecule with a bond in position a or b;
$X^1$ is O, S or NH;
$X^2$ is O or S;
$X^3$, $X^4$ and $X^5$ each independently are CH or N; provided that exactly two of $X^3$, $X^4$ and $X^5$ are N, the other being CH;
$X^6$, $X^7$, $X^8$ and $X^9$ each independently are CH or N; provided that one or two of $X^6$, $X^7$, $X^8$ and $X^9$ are N, the other being CH;
$X^{10}$, $X^{11}$, $X^{12}$ and $X^{13}$ each independently are CH or N; provided that maximum one of $X^{10}$, $X^{11}$, $X^{12}$ and $X^{13}$ is N, the other being CH;
$X^{14}$ is CH or N;
$X^{15}$ is NH, O or S;
$X^{16}$ is CH or N;
$X^{17}$ is CH or N;
$X^{18}$ is NH, S or O;
$X^{19}$ is CH or N;
$X^{20}$ is NH or S;
$R^5$ and $R^6$ taken together form a bivalent radical —$R^5$-$R^6$—, having formula:

$$-(CH_2)_m-O-(CH_2)_{n-m}- \quad (a),$$

$$-(CH_2)_{n-m}-O-(CH_2)_m- \quad (b),$$

$$-(CH_2)_s- \quad (c), or$$

$$-CH=CH-CH=CH- \quad (d);$$

wherein the bivalent radical —$R^5$-$R^6$— may, where possible, be substituted with one or more substituents selected from the group consisting of halo, $C_{1-4}$alkyl, hydroxyl, $C_{1-4}$alkyloxy and oxo;

m represents 0, 1 or 2;

n represents 2, 3 or 4;

s represents 3, 4 or 5;

wherein radicals (d-1)-(d-11) may be substituted with one or more substituents each independently selected from the group consisting of $C_{1-4}$alkyloxy, halo, $C_{1-4}$alkylcarbonyl, $C_{1-4}$alkylthio, $C_{1-4}$alkylsulphonyl, $C_{1-4}$alkylsulphinyl, and $C_{1-4}$alkyl optionally substituted with one or more halo substituents;

provided that radicals (d-1)-(d-11) are not substituted in the α-positions to the carbon atom of attachment;

and the pharmaceutically acceptable addition salts, and the solvates thereof;

provided that the compound is not 5,6-dihydro-4-(2-pyridinyl)-4H-pyrrolo[1,2-a][1,4]benzodiazepine .HCl.

The present invention also concerns methods for the preparation of compounds of Formula (I) and pharmaceutical compositions comprising them.

The present compounds are useful agents for combating fungi in vivo.

The novel compounds described in the present invention may be useful in the treatment or prevention of infections caused by dermatophytes, systemic fungal infections and onychomycosis; in particular infections caused by dermatophytes.

The novel compounds described in the present invention may be active against a wide variety of fungi, such as *Candida* spp., e.g. *Candida albicans*, *Candida glabrata*, *Candida krucei*; *Candida parapsilosis*, *Candida kefyr*, *Candida tropicalis*; *Aspergillus* spp., e.g. *Aspergillus fumigatus*, *Aspergillus niger*, *Aspergillus flavus*; *Cryptococcus neoformans*; *Sporothrix schenckii*; *Epidermophyton floccosum*; *Microsporum* spp., e.g. *Microsporum canis*, *Microsporum gypseum*; *Trichophyton* spp., e.g. *Trichophyton mentagrophytes*, *Trichophyton rubrum*, *Trichophyton quinckeanum*, *Trichophyton tonsurans*, *Trichophyton verrucosum*, *Trichophyton violaceum*, *Trichophyton interdigitale*, *Trichophyton soudanense*; *Fusarium* spp., e.g. *Fusarium solani*, *Fusarium oxysporum*, *Fusarium proliferatum*, *Fusarium verticillioides*; *Rhizomucor* spp., e.g. *Rhizomucor miehei*, *Rhizomucor pusillus*; *Mucor circinelloides*; *Rhizopus* spp., e.g. *Rhizopus oryzae*, *Rhizopus microspores*; *Malassezia furfur*; *Acremonium* spp.; *Paecilomyces*; *Scopulariopsis*; *Arthrographis* spp.; *Scytalidium*; *Scedosporium* spp., e.g. *Scedosporium apiospermum*, *Scedosporium prolificans*; *Trichoderma* spp.; *Penicillium* spp.; *Penicillium marneffei*; *Blastoschizomyces*.

In view of the aforementioned pharmacology of the present compounds, it follows that they are suitable for use as a medicament.

The invention also relates to a compound according to the general Formula (I), the stereoisomeric forms thereof and the pharmaceutically acceptable addition salts and the solvates thereof, for use in the treatment or prevention of fungal infections.

One advantage of the compounds or a part of the compounds of the present invention may lie in their enhanced bioavailability, improved metabolic stability properties, improved PK properties, reduced hERG channel inhibition, or reduced cytochrome P450 liabilities compared with the compounds disclosed in the prior art.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

DETAILED DESCRIPTION

When describing the compounds of the invention, the terms used are to be construed in accordance with the following definitions, unless a context dictates otherwise.

Whenever the term "substituted" is used in the present invention, it is meant, unless otherwise is indicated or is clear from the context, to indicate that one or more hydrogens, in particular from 1 to 4 hydrogens, preferably from 1 to 3 hydrogens, more preferably 1 hydrogen, on the atom or radical indicated in the expression using "substituted" are replaced with a selection from the indicated group, provided that the normal valency is not exceeded, and that the substitution results in a chemically stable compound, i.e. a compound that is sufficiently robust to survive isolation to a useful degree of purity from a reaction mixture, and formulation into a therapeutic agent.

The term "halo" or "halogen" as a group or part of a group is generic for fluoro, chloro, bromo, iodo unless otherwise is indicated or is clear from the context.

The term "$C_{1-4}$alkyl" as a group or part of a group (e.g. in $C_{1-4}$alkylcarbonyl, $C_{1-4}$alkylthio, $C_{1-4}$alkylsulphonyl, $C_{1-4}$alkylsulphinyl) refers to a hydrocarbyl radical of Formula $C_nH_{2n+1}$ wherein n is a number ranging from 1 to 4. $C_{1-4}$alkyl groups comprise from 1 to 4 carbon atoms, preferably from 1 to 3 carbon atoms, still more preferably 1 to 2 carbon atoms. Alkyl groups may be linear or branched and may be substituted as indicated herein. When a subscript is used herein following a carbon atom, the subscript refers to the number of carbon atoms that the named group may contain. Thus, for example, $C_{1-4}$alkyl includes all linear, or branched alkyl groups with between 1 and 4 carbon atoms, and thus includes such as for example methyl, ethyl, n-propyl, i-propyl, 2-methyl-ethyl, butyl and its isomers (e.g. n-butyl, isobutyl and tert-butyl), and the like.

The term "$C_{1-4}$alkyloxy" as a group or part of a group refers to a radical having the Formula —$OR^a$ wherein $R^a$ is $C_{1-4}$alkyl. Non-limiting examples of suitable $C_{1-4}$alkyloxy include methyloxy (also methoxy), ethyloxy (also ethoxy), propyloxy, isopropyloxy, butyloxy, isobutyloxy, sec-butyloxy and tert-butyloxy.

The chemical names of the compounds of the present invention were generated according to the nomenclature rules agreed upon by the Chemical Abstracts Service, using Advanced Chemical Development, Inc., nomenclature software (ACD/Labs Release 12.00 Product version 12.01; Build 33104, 27 May 2009).

In case of tautomeric forms, it should be clear that the other non-depicted tautomeric form is also included within the scope of the present invention.

The atoms in the tricyclic system are numbered as shown in the following formula (Q):

(Q)

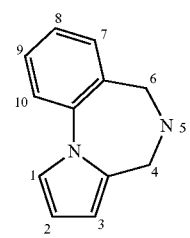

When any variable occurs more than one time in any constituent, each definition is independent.

Whenever radicals (d-1)-(d-11) are substituted with one or more substituents, those substituents may replace any hydrogen atom bound to a carbon or nitrogen atom, including NH and CH groups in the definition of $X^1$, $X^3$-$X^{14}$, $X^{16}$-$X^{20}$, provided however that NH and CH groups in the α-positions to the carbon atom of attachment are not substituted.

For example, (d-11)

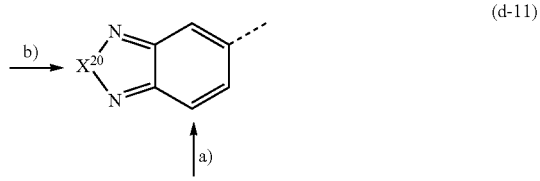

may be substituted on the CH group in position a), but also on the NH group in position b) in case $X^{20}$ represents NH.

It will be appreciated that some of the compounds of Formula (I) and their pharmaceutically acceptable addition salts and solvates may contain one or more centers of chirality and exist as stereoisomeric forms.

Hereinbefore and hereinafter, the term "compound(s) of formula (I)" is meant to include the addition salts, the solvates and the stereoisomers thereof.

The terms "stereoisomers", "stereoisomeric forms" or "stereochemically isomeric forms" hereinbefore or hereinafter are used interchangeably.

The term "stereoisomeric forms" as used hereinbefore defines all the possible isomeric forms that the compounds of Formula (I) may possess. Unless otherwise mentioned or indicated, the chemical designation of compounds denotes the mixture of all possible stereochemically isomeric forms. The invention includes all stereoisomers of the compound of Formula (I) either as a pure stereoisomer or as a mixture of two or more stereoisomers. The definition of "compound of formula (I)" inherently includes all stereoisomers of the compound of formula (I) either as a pure stereoisomer or as a mixture of two or more stereoisomers.

Enantiomers are stereoisomers that are non-superimposable mirror images of each other. A 1:1 mixture of a pair of enantiomers is a racemate or racemic mixture. More in particular, stereogenic centers may have the R- or S-configuration. Diastereomers (or diastereoisomers) are stereoisomers that are not enantiomers, i.e. they are not related as mirror images. If a compound contains a double bond, the substituents may be in the E or the Z configuration at said double bond. Substituents on bivalent cyclic (partially) saturated radicals may have either the cis- or trans-configuration; for example if a compound contains a disubstituted cycloalkyl group, the substituents may be in the cis or trans configuration. Stereoisomeric forms of the compounds of Formula (I) are embraced within the scope of this invention. Therefore, the invention includes enantiomers, diastereomers, racemates, E isomers, Z isomers, cis isomers, trans isomers and mixtures thereof, whenever chemically possible.

The absolute configuration is specified according to the Cahn-Ingold-Prelog system. The configuration at an asymmetric atom is specified by either R or S. Resolved compounds whose absolute configuration is not known can be designated by (+) or (−) depending on the direction in which they rotate plane polarized light. When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other isomers. Thus, when a compound of formula (I) is for instance specified as (R), this means that the compound is substantially free of the (S) isomer; when a compound of formula (I) is for instance specified as E, this means that the compound is substantially free of the Z isomer; when a compound of formula (I) is for instance specified as cis, this means that the compound is substantially free of the trans isomer.

Some of the compounds according to formula (I) may also exist in their tautomeric form. Such forms although not explicitly indicated in the above formula are intended to be included within the scope of the present invention.

For therapeutic use, salts of the compounds of Formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove or hereinafter are meant to comprise the therapeutically active non-toxic acid and base addition salt forms which the compounds of Formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-amino-salicylic, pamoic and the like acids. Conversely said salt forms can be converted by treatment with an appropriate base into the free base form.

The compounds of Formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term solvate comprises the hydrates and solvent addition forms which the compounds of Formula (I) are able to form, as well as the salts thereof. Examples of such forms are e.g. hydrates, alcoholates and the like.

The compounds of Formula (I) as prepared in the processes described below may be synthesized in the form of mixtures of enantiomers, in particular racemic mixtures of enantiomers that can be separated from one another following art-known resolution procedures. A manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

In the framework of this application, a compound according to the invention is inherently intended to comprise all isotopic combinations of its chemical elements. In the framework of this application, a chemical element, in particular when mentioned in relation to a compound according to Formula (I), comprises all isotopes and isotopic mixtures of this element. For example, when hydrogen is mentioned, it is understood to refer to $^1H$, $^2H$, $^3H$ and mixtures thereof.

A compound according to the invention therefore inherently comprises a compound with one or more isotopes of one or more element, and mixtures thereof, including a radioactive compound, also called radiolabelled compound, wherein one or more non-radioactive atoms has been replaced by one of its radioactive isotopes. By the term "radiolabelled compound" is meant any compound according to Formula (I), or a pharmaceutically acceptable salt thereof, which contains at least one radioactive atom. For example, a compound can be labelled with positron or with gamma emitting radioactive isotopes. For radioligand-binding techniques, the $^3H$-atom or the $^{125}I$-atom is the atom of choice to be replaced. For imaging, the most commonly used positron emitting (PET) radioactive isotopes are $^{11}C$, $^{18}F$, $^{15}O$ and $^{13}N$, all of which are accelerator produced and have half-lives of 20, 100, 2 and 10 minutes respectively.

Since the half-lives of these radioactive isotopes are so short, it is only feasible to use them at institutions which have an accelerator on site for their production, thus limiting their use. The most widely used of these are $^{18}F$, $^{99m}Tc$, $^{201}Tl$ and $^{123}I$. The handling of these radioactive isotopes, their production, isolation and incorporation in a molecule are known to the skilled person.

In particular, the radioactive atom is selected from the group of hydrogen, carbon, nitrogen, sulfur, oxygen and halogen. In particular, the radioactive isotope is selected from the group of $^3H$, $^{11}C$, $^{18}F$, $^{122}I$, $^{123}I$, $^{125}I$, $^{131}I$, $^{75}Br$, $^{76}Br$, $^{77}Br$ and $^{82}Br$.

As used in the specification and the appended claims, the singular forms "a", "an," and "the" also include plural referents unless the context clearly dictates otherwise. By way of example, "a compound" means one compound or more than one compound.

The terms described above and others used in the specification are well understood to those in the art.

Preferred features of the compounds of this invention are now set forth.

In an embodiment, the present invention concerns novel compounds of Formula (I):

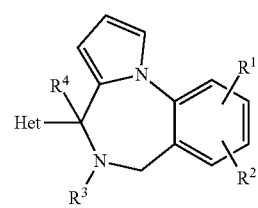

(I)

and stereoisomeric forms thereof, wherein $R^1$ is hydrogen, halo, $C_{1-4}$alkyl or $C_{1-4}$alkyloxy;

$R^2$ is hydrogen, halo, $C_{1-4}$alkyl or $C_{1-4}$alkyloxy;

$R^3$ and $R^4$ are hydrogen;

or $R^3$ and $R^4$ taken together form a bond;

Het is a monocyclic or bicyclic heterocyclic radical selected from

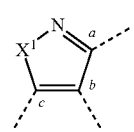

(d-1)

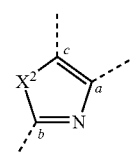

(d-2)

(d-3)

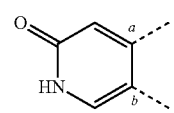

(d-4)

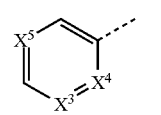

(d-5)

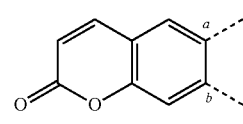

(d-6)

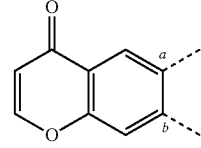

(d-7)

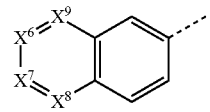

(d-8)

-continued

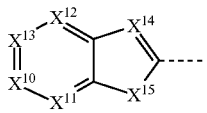
(d-9)

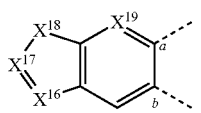
(d-10)

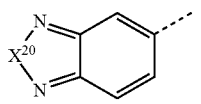
(d-11)

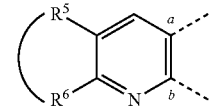
(d-12)

(d-1) and (d-2) are attached to the remainder of the molecule with a bond in position a, b or c;
(d-4), (d-6), (d-7), (d-10) and (d-12) are attached to the remainder of the molecule with a bond in position a or b;
$X^1$ is O, S or NH;
$X^2$ is O or S;
$X^3$, $X^4$ and $X^5$ each independently are CH or N; provided that exactly two of $X^3$, $X^4$ and $X^5$ are N, the other being CH;
$X^6$, $X^7$, $X^8$ and $X^9$ each independently are CH or N; provided that exactly one of $X^6$, $X^7$, $X^8$ and $X^9$ is N, the other being CH;
$X^{10}$, $X^{11}$, $X^{12}$ and $X^{13}$ each independently are CH or N; provided that maximum one of $X^{10}$, $X^{11}$, $X^{12}$ and $X^{13}$ is N, the other being CH;
$X^{14}$ is CH or N;
$X^{15}$ is O or S;
$X^{16}$ is CH or N;
$X^{17}$ is CH or N;
$X^{18}$ is NH, S or O;
$X^{19}$ is CH or N;
$X^{20}$ is NH or S;
$R^5$ and $R^6$ taken together form a bivalent radical —$R^5$-$R^6$—, having formula:

$$—(CH_2)_m—O—(CH_2)_{n-m}— \quad (a),$$

$$—(CH_2)_{n-m}—O—(CH_2)_m— \quad (b), \text{ or}$$

$$—(CH_2)_s— \quad (c),$$

wherein the bivalent radical —$R^5$-$R^6$— may, where possible, be substituted with one or more substituents selected from the group consisting of halo, $C_{1-4}$alkyl, hydroxyl, $C_{1-4}$alkyloxy and oxo;
m represents 0, 1 or 2;
n represents 2, 3 or 4;
s represents 3, 4 or 5;
wherein radicals (d-1)-(d-11) may be substituted with one or more substituents each independently selected from the group consisting of $C_{1-4}$alkyloxy, halo, $C_{1-4}$alkylcarbonyl, $C_{1-4}$alkylthio, $C_{1-4}$alkylsulphonyl, $C_{1-4}$alkylsulphinyl, and $C_{1-4}$alkyl optionally substituted with one or more halo substituents; provided that radicals (d-1)-(d-11) are not substituted in the α-positions to the carbon atom of attachment;

and the pharmaceutically acceptable addition salts, and the solvates thereof.

In an embodiment, the present invention concerns novel compounds of Formula (I):

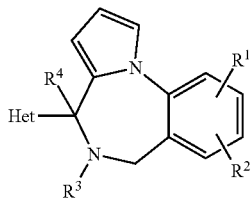
(I)

and stereoisomeric forms thereof, wherein
$R^1$ is hydrogen, halo, $C_{1-4}$alkyl or $C_{1-4}$alkyloxy;
$R^2$ is hydrogen, halo, $C_{1-4}$alkyl or $C_{1-4}$alkyloxy;
$R^3$ and $R^4$ are hydrogen;
or $R^3$ and $R^4$ taken together form a bond;
Het is a monocyclic or bicyclic heterocyclic radical selected from

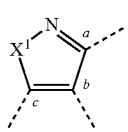
(d-1)

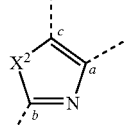
(d-2)

(d-3)

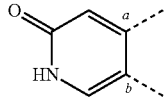
(d-4)

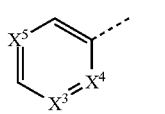
(d-5)

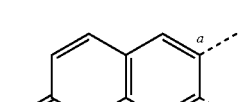
(d-6)

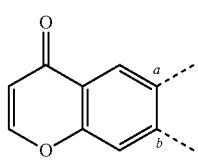
(d-7)

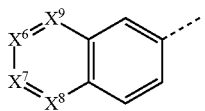 (d-8)

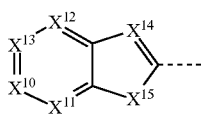 (d-9)

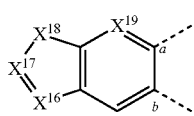 (d-10)

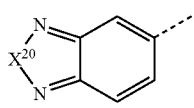 (d-11)

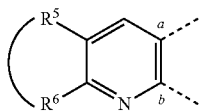 (d-12)

(d-1) and (d-2) are attached to the remainder of the molecule with a bond in position a, b or c;

(d-4), (d-6), (d-7), (d-10) and (d-12) are attached to the remainder of the molecule with a bond in position a or b;

$X^1$ is O, S or NH;

$X^2$ is O or S;

$X^3$, $X^4$ and $X^5$ each independently are CH or N; provided that exactly two of $X^3$, $X^4$ and $X^5$ are N, the other being CH;

$X^6$, $X^7$, $X^8$ and $X^9$ each independently are CH or N; provided that exactly one of $X^6$, $X^7$, $X^8$ and $X^9$ is N, the other being CH;

$X^{10}$, $X^{11}$, $X^{12}$ and $X^{13}$ each independently are CH or N; provided that maximum one of $X^{10}$, $X^{11}$, $X^{12}$ and $X^{13}$ is N, the other being CH;

$X^{14}$ is CH or N;

$X^{15}$ is O or S;

$X^{16}$ is CH or N;

$X^{17}$ is CH or N;

$X^{18}$ is NH, S or O;

$X^{19}$ is CH or N;

$X^{20}$ is NH or S;

$R^5$ and $R^6$ taken together form a bivalent radical —$R^5$-$R^6$—, having formula:

 (a),

 (b), or

 (c);

wherein the bivalent radical —$R^5$-$R^6$— may, where possible, be substituted with one or more substituents selected from the group consisting of halo, $C_{1-4}$alkyl, hydroxyl, $C_{1-4}$alkyloxy and oxo;

m represents 0, 1 or 2;

n represents 2, 3 or 4;

s represents 3, 4 or 5;

wherein radicals (d-1)-(d-11) may be substituted with one or more substituents each independently selected from the group consisting of $C_{1-4}$alkyloxy, halo, $C_{1-4}$alkylcarbonyl, $C_{1-4}$alkylthio, $C_{1-4}$alkylsulphonyl, $C_{1-4}$alkylsulphinyl, and $C_{1-4}$alkyl optionally substituted with one or more halo substituents; provided that radicals (d-1)-(d-11) are not substituted in the α-positions to the carbon atom of attachment;

and the pharmaceutically acceptable addition salts, and the solvates thereof; provided that the compound is not 5,6-dihydro-4-(2-pyridinyl)-4H-pyrrolo[1,2-a][1,4]benzodiazepine .HCl.

In an embodiment, the invention relates to compounds of Formula (I) and stereoisomeric forms thereof, wherein $R^1$ is hydrogen, halo or $C_{1-4}$alkyl;

$R^2$ is hydrogen, halo or $C_{1-4}$alkyl;

$R^3$ and $R^4$ are hydrogen;

or $R^3$ and $R^4$ taken together form a bond;

Het is a monocyclic or bicyclic heterocyclic radical selected from

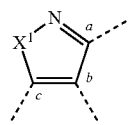 (d-1)

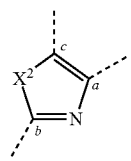 (d-2)

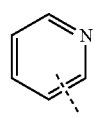 (d-3)

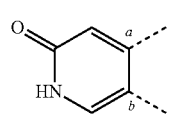 (d-4)

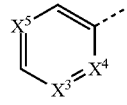 (d-5)

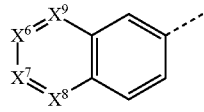 (d-8)

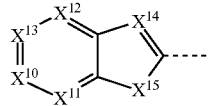 (d-9)

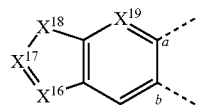 (d-10)

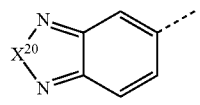 (d-11)

-continued (d-12)
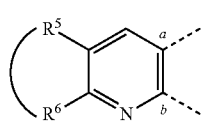

(d-1) and (d-2) are attached to the remainder of the molecule with a bond in position a, b or c;
(d-4), (d-10) and (d-12) are attached to the remainder of the molecule with a bond in position a or b;
$X^1$ is O or NH;
$X^2$ is S;
$X^3$, $X^4$ and $X^5$ each independently are CH or N; provided that exactly two of $X^3$, $X^4$ and $X^5$ are N, the other being CH;
$X^6$, $X^7$, $X^8$ and $X^9$ each independently are CH or N; provided that one or two of $X^6$, $X^7$, $X^8$ and $X^9$ are N, the other being CH;
$X^{10}$, $X^{11}$, $X^{12}$ and $X^{13}$ each independently are CH or N; provided that maximum one of $X^{10}$, $X^{11}$, $X^{12}$ and $X^{13}$ is N, the other being CH;
$X^{14}$ is CH or N;
$X^{15}$ is O or S;
$X^{16}$ is CH or N;
$X^{17}$ is CH or N;
$X^{18}$ is NH, S or O;
$X^{19}$ is CH or N;
$X^{20}$ is NH or S;
$R^5$ and $R^6$ taken together form a bivalent radical —$R^5$-$R^6$—, having formula:

—(CH$_2$)$_s$—  (c), or

—CH=CH—CH=CH—  (d);

s represents 3, 4 or 5;
wherein radicals (d-1)-(d-5) and (d-8)-(d-11) may be substituted with one or more substituents each independently selected from the group consisting of $C_{1-4}$alkyloxy, halo, $C_{1-4}$alkylcarbonyl, and $C_{1-4}$alkyl optionally substituted with one or more halo substituents; provided that radicals (d-1)-(d-5) and (d-8)-(d-11) are not substituted in the α-positions to the carbon atom of attachment;
and the pharmaceutically acceptable addition salts, and the solvates thereof;
provided that the compound is not 5,6-dihydro-4-(2-pyridinyl)-4H-pyrrolo[1,2-a][1,4]benzodiazepine .HCl.
In an embodiment, the invention relates to compounds of Formula (I) and stereoisomeric forms thereof, wherein
$R^1$ is hydrogen, halo or $C_{1-4}$alkyl;
$R^2$ is hydrogen, halo or $C_{1-4}$alkyl;
$R^3$ and $R^4$ are hydrogen;
or $R^3$ and $R^4$ taken together form a bond;
Het is a monocyclic or bicyclic heterocyclic radical selected from

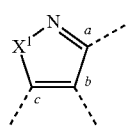
(d-1)

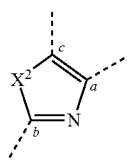
(d-2)

(d-3)

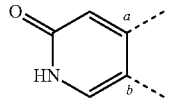
(d-4)

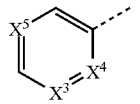
(d-5)

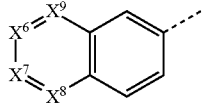
(d-8)

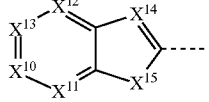
(d-9)

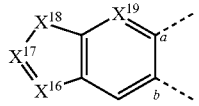
(d-10)

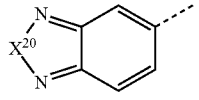
(d-11)

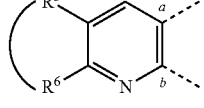
(d-12)

(d-1) and (d-2) are attached to the remainder of the molecule with a bond in position a, b or c;
(d-4), (d-10) and (d-12) are attached to the remainder of the molecule with a bond in position a or b;
$X^1$ is O or NH;
$X^2$ is S;
$X^3$, $X^4$ and $X^5$ each independently are CH or N; provided that exactly two of $X^3$, $X^4$ and $X^5$ are N, the other being CH;
$X^6$, $X^7$, $X^8$ and $X^9$ each independently are CH or N; provided that exactly one of $X^6$, $X^7$, $X^8$ and $X^9$ is N, the other being CH;
$X^{10}$, $X^{11}$, $X^{12}$ and $X^{13}$ each independently are CH or N; provided that maximum one of $X^{10}$, $X^{11}$, $X^{12}$ and $X^{13}$ is N, the other being CH;
$X^{14}$ is CH or N;
$X^{15}$ is O or S;
$X^{16}$ is CH or N;
$X^{17}$ is CH or N;

$X^{18}$ is NH, S or O;
$X^{19}$ is CH or N;
$X^{20}$ is NH or S;
$R^5$ and $R^6$ taken together form a bivalent radical —$R^5$-$R^6$—, having formula:

—(CH$_2$)$_s$— (c);

s represents 3, 4 or 5;
wherein radicals (d-1)-(d-5) and (d-8)-(d-11) may be substituted with one or more substituents each independently selected from the group consisting of $C_{1-4}$alkyloxy, halo, $C_{1-4}$alkylcarbonyl, and $C_{1-4}$alkyl optionally substituted with one or more halo substituents; provided that radicals (d-1)-(d-5) and (d-8)-(d-11) are not substituted in the α-positions to the carbon atom of attachment;
and the pharmaceutically acceptable addition salts, and the solvates thereof; provided that the compound is not 5,6-dihydro-4-(2-pyridinyl)-4H-pyrrolo[1,2-a][1,4]benzodiazepine .HCl.

In an embodiment, the invention relates to compounds of Formula (I) and stereoisomeric forms thereof, wherein
$R^1$ is hydrogen, chloro, fluoro or methyl;
$R^2$ is hydrogen, chloro, fluoro or methyl;
$R^3$ and $R^4$ are hydrogen;
or $R^3$ and $R^4$ taken together form a bond;
Het is a monocyclic or bicyclic heterocyclic radical selected from

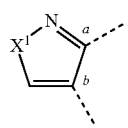 (d-1a)

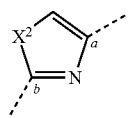 (d-2a)

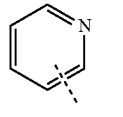 (d-3)

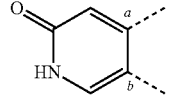 (d-4)

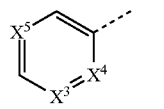 (d-5)

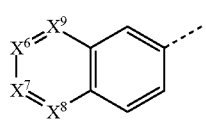 (d-8)

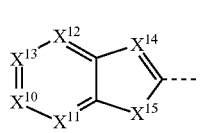 (d-9)

-continued

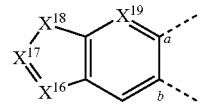 (d-10)

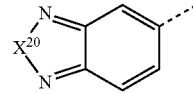 (d-11)

 (d-12)

(d-1a), (d-2a), (d-4), (d-10) and (d-12) are attached to the remainder of the molecule with a bond in position a or b;
$X^1$ is O or NH;
$X^2$ is S;
$X^3$, $X^4$ and $X^5$ each independently are CH or N; provided that exactly two of $X^3$, $X^4$ and $X^5$ are N, the other being CH;
$X^6$, $X^7$ and $X^9$ are CH;
$X^8$ is N;
$X^{10}$, $X^{11}$, $X^{12}$ and $X^{13}$ each independently are CH or N; provided that maximum one of $X^{10}$, $X^{11}$, $X^{12}$ and $X^{13}$ is N, the other being CH;
$X^{14}$ is CH or N;
$X^{15}$ is O or S;
$X^{16}$ is CH or N;
$X^{17}$ is CH or N;
$X^{18}$ is NH, S or O;
$X^{19}$ is CH or N;
$X^{20}$ is NH or S;
$R^5$ and $R^6$ taken together form a bivalent radical —$R^5$-$R^6$—, having formula:

—(CH$_2$)$_s$— (c);

s represents 3;
wherein radicals (d-1a)-(d-5) and (d-8)-(d-11) may be substituted with one or more substituents each independently selected from the group consisting of methoxy, chloro, fluoro, methylcarbonyl, and $C_{1-4}$alkyl optionally substituted with one or more fluoro substituents; provided that radicals (d-1a)-(d-5) and (d-8)-(d-11) are not substituted in the α-positions to the carbon atom of attachment;
and the pharmaceutically acceptable addition salts, and the solvates thereof;
provided that the compound is not 5,6-dihydro-4-(2-pyridinyl)-4H-pyrrolo[1,2-a][1,4]benzodiazepine .HCl.

In an embodiment, the invention relates to compounds of Formula (I) and stereoisomeric forms thereof, wherein
$R^1$ is hydrogen, halo or $C_{1-4}$alkyl;
$R^2$ is hydrogen, halo or $C_{1-4}$alkyl;
$R^3$ and $R^4$ are hydrogen;
or $R^3$ and $R^4$ taken together form a bond;
Het is a monocyclic or bicyclic heterocyclic radical selected from (d-1), (d-2), (d-3), (d-5), (d-8), (d-9), (d-10) and (d-11);
(d-1) and (d-2) are attached to the remainder of the molecule with a bond in position a, b or c;
(d-10) is attached to the remainder of the molecule with a bond in position a or b;
$X^1$ is O or NH;
$X^2$ is S;

$X^3$, $X^4$ and $X^5$ each independently are CH or N; provided that exactly two of $X^3$, $X^4$ and $X^5$ are N, the other being CH;

$X^6$, $X^7$, $X^8$ and $X^9$ each independently are CH or N; provided that exactly one of $X^6$, $X^7$, $X^8$ and $X^9$ is N, the other being CH;

$X^{10}$, $X^{11}$, $X^{12}$ and $X^{13}$ each independently are CH or N; provided that maximum one of $X^{10}$, $X^{11}$, $X^{12}$ and $X^{13}$ is N, the other being CH;

$X^{14}$ is CH or N;
$X^{15}$ is O or S;
$X^{16}$ is CH or N;
$X^{17}$ is CH or N;
$X^{18}$ is NH, S or O;
$X^{19}$ is CH or N;
$X^{20}$ is NH or S;

wherein radicals (d-1), (d-2), (d-3), (d-5), (d-8), (d-9), (d-10) and (d-11) may be substituted with one or more substituents each independently selected from the group consisting of $C_{1-4}$alkyloxy, halo, $C_{1-4}$alkylcarbonyl, and $C_{1-4}$alkyl optionally substituted with one or more halo substituents; provided that radicals (d-1), (d-2), (d-3), (d-5), (d-8), (d-9), (d-10) and (d-11) are not substituted in the α-positions to the carbon atom of attachment;

and the pharmaceutically acceptable addition salts, and the solvates thereof; provided that the compound is not 5,6-dihydro-4-(2-pyridinyl)-4H-pyrrolo[1,2-a][1,4]benzodiazepine .HCl.

In an embodiment, the invention relates to compounds of Formula (I) and stereoisomeric forms thereof, wherein
$R^1$ is hydrogen, halo or $C_{1-4}$alkyl;
$R^2$ is hydrogen, halo or $C_{1-4}$alkyl;
$R^3$ and $R^4$ are hydrogen;
or $R^3$ and $R^4$ taken together form a bond;
Het is

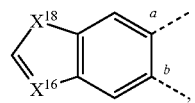

(d-9a)

$X^{15}$ is O or S; in particular O;

wherein radical (d-9a) may be substituted with one or more substituents each independently selected from the group consisting of $C_{1-4}$alkyloxy, halo, $C_{1-4}$alkylcarbonyl, and $C_{1-4}$alkyl optionally substituted with one or more halo substituents; provided that radical (d-9a) is not substituted in the α-positions to the carbon atom of attachment;

and the pharmaceutically acceptable addition salts, and the solvates thereof.

In an embodiment, the invention relates to compounds of Formula (I) and stereoisomeric forms thereof, wherein
$R^1$ is hydrogen, halo or $C_{1-4}$alkyl;
$R^2$ is hydrogen, halo or $C_{1-4}$alkyl;
$R^3$ and $R^4$ are hydrogen;
or $R^3$ and $R^4$ taken together form a bond;
Het is selected from

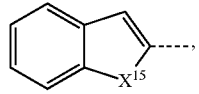

(d-9a)

and

-continued

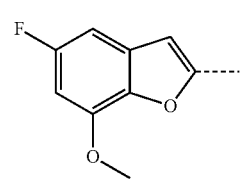

(d-10a)

(d-10a) is attached to the remainder of the molecule with a bond in position a or b;

$X^{15}$ is O or S; in particular O;
$X^{16}$ is CH or N; in particular CH;
$X^{18}$ is NH, S or O; in particular S or O; more in particular O;

wherein radicals (d-9a) and (d-10a) may be substituted with one or more substituents each independently selected from the group consisting of $C_{1-4}$alkyloxy, halo, $C_{1-4}$alkylcarbonyl, and $C_{1-4}$alkyl optionally substituted with one or more halo substituents; provided that radicals (d-9a) and (d-10a) are not substituted in the α-positions to the carbon atom of attachment;

and the pharmaceutically acceptable addition salts, and the solvates thereof.

In an embodiment, the invention relates to any of the other embodiments or any combination of the other embodiments, wherein
Het is

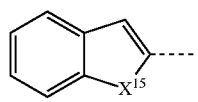

(d-9b)

In an embodiment, the invention relates to any of the other embodiments or any combination of the other embodiments, wherein Het is quinolinyl.

In an embodiment, the invention relates to any of the other embodiments or any combination of the other embodiments, wherein $R^1$ is hydrogen; $R^2$ is hydrogen; $R^3$ and $R^4$ are taken together to form a bond; and Het is quinolinyl.

In another embodiment, the invention relates to any of the other embodiments or any combination of the other embodiments, wherein $R^3$ and $R^4$ are hydrogen.

In another embodiment, the invention relates to any of the other embodiments or any combination of the other embodiments, wherein $R^3$ and $R^4$ are taken together to form a bond.

In another embodiment, the invention relates to any of the other embodiments or any combination of the other embodiments, wherein radicals (d-1)-(d-11) may be substituted with one or more substituents each independently selected from the group consisting of $C_{1-4}$alkyloxy, halo, $C_{1-4}$alkylcarbonyl, $C_{1-4}$alkylsulphonyl, $C_{1-4}$alkylsulphinyl, and $C_{1-4}$alkyl optionally substituted with one or more halo substituents;
in particular $C_{1-4}$alkyloxy, halo, $C_{1-4}$alkylcarbonyl, and $C_{1-4}$alkyl optionally substituted with one or more halo substituents;
provided that radicals (d-1)-(d-11) are not substituted in the α-positions to the carbon atom of attachment.

In another embodiment, the invention relates to any of the other embodiments or any combination of the other embodiments,
wherein radicals (d-1)-(d-2) and (d-4)-(d-11) may be substituted with one or more substituents each independently selected from the group consisting of $C_{1-4}$alkyloxy, halo, $C_{1-4}$alkylcarbonyl, $C_{1-4}$alkylthio, $C_{1-4}$alkylsulphonyl, $C_{1-4}$alkylsulphinyl, and $C_{1-4}$alkyl optionally substituted with one or more halo substituents;

wherein radical (d-3) is substituted with one or more substituents each independently selected from the group consisting of $C_{1-4}$alkyloxy, halo, $C_{1-4}$alkylcarbonyl, $C_{1-4}$alkylthio, $C_{1-4}$alkylsulphonyl, $C_{1-4}$alkylsulphinyl, and $C_{1-4}$alkyl optionally substituted with one or more halo substituents;

provided that radicals (d-1)-(d-11) are not substituted in the α-positions to the carbon atom of attachment.

In another embodiment, the invention relates to any of the other embodiments or any combination of the other embodiments, wherein Het is a monocyclic or bicyclic heterocyclic radical selected from the group consisting of pyrazolyl, pyridinyl, pyrimidinyl, pyridazinyl, benzofuranyl, benzoxazolyl, quinolinyl, furo[3,2-c]pyridinyl, furo[2,3-b]pyridinyl, furo[2,3-c]pyridinyl, benzo[b]thiophenyl, benzothiazolyl, quinoxalinyl, isoxazolyl, thiazolyl, indolyl, 1,2,3-benzothiadiazolyl, 2,1,3-benzothiadiazolyl, 1H-1,2,3-benzotriazolyl, 2H-1,2,3-benzotriazolyl, 6,7-dihydro-5H-cyclopenta[b]pyridin-3-yl, 1,2-dihydro-2-oxo-pyridinyl and benzimidazolyl;

in particular wherein Het is a monocyclic or bicyclic heterocyclic radical selected from the group consisting of pyridinyl, benzofuranyl and benzo[b]thiophenyl;

more in particular wherein Het is a monocyclic or bicyclic heterocyclic radical selected from the group consisting of benzofuranyl and benzo[b]thiophenyl;

wherein said radicals may be substituted with one or more substituents each independently selected from the group consisting of $C_{1-4}$alkyloxy, halo, $C_{1-4}$alkylcarbonyl, and $C_{1-4}$alkyl optionally substituted with one or more halo substituents;

provided that said radicals are not substituted in the α-positions to the carbon atom of attachment.

In another embodiment, the invention relates to any of the other embodiments or any combination of the other embodiments, wherein Het is a monocyclic or bicyclic heterocyclic radical selected from the group consisting of pyridinyl, benzofuranyl and benzo[b]thiophenyl;

wherein benzofuranyl and benzo[b]thiophenyl may be substituted with one or more substituents each independently selected from the group consisting of $C_{1-4}$alkyloxy, halo, $C_{1-4}$alkylcarbonyl, and $C_{1-4}$alkyl optionally substituted with one or more halo substituents;

wherein pyridinyl is substituted with one or more substituents each independently selected from the group consisting of $C_{1-4}$alkyloxy, halo, $C_{1-4}$alkylcarbonyl, and $C_{1-4}$alkyl optionally substituted with one or more halo substituents;

provided that said radicals are not substituted in the α-positions to the carbon atom of attachment.

In another embodiment, the invention relates to any of the other embodiments or any combination of the other embodiments, wherein Het being pyridinyl is substituted with one or more substituents defined in the other embodiment;

provided that pyridinyl is not substituted in the α-positions to the carbon atom of attachment.

In another embodiment, the invention relates to any of the other embodiments or any combination of the other embodiments, wherein at least one of $R^1$ and $R^2$ is other than hydrogen.

In a particular embodiment, the invention relates to any of the other embodiments or any combination of the other embodiments, wherein $R^2$ is hydrogen, chloro or fluoro.

In another embodiment, the invention relates to any of the other embodiments or any combination of the other embodiments, wherein $R^1$ or $R^2$ is in the 7-position and is other than hydrogen.

In another embodiment, the invention relates to any of the other embodiments or any combination of the other embodiments, wherein $R^1$ is in the 7-position and is chloro or fluoro; in particular $R^1$ is in the 7-position and is chloro.

In another embodiment, the invention relates to any of the other embodiments or any combination of the other embodiments, wherein $R^1$ is in the 7-position and is chloro, fluoro or methyl; in particular $R^1$ is in the 7-position and is chloro or fluoro; more in particular $R^1$ is in the 7-position and is chloro; and $R^2$ is in any of the other positions and is hydrogen, chloro, fluoro or methyl; in particular chloro, fluoro or methyl; more in particular chloro or fluoro; even more in particular chloro.

In another embodiment, the invention relates to any of the other embodiments or any combination of the other embodiments, wherein $R^2$ is in the 7-position and is chloro, fluoro or methyl.

In another embodiment, the invention relates to any of the other embodiments or any combination of the other embodiments, wherein $R^2$ is in the 7-position and is chloro, fluoro or methyl; and $R^1$ is in any of the other positions and is hydrogen, chloro or fluoro; in particular chloro or fluoro; more in particular chloro.

In another embodiment, the invention relates to any of the other embodiments or any combination of the other embodiments wherein $R^1$ is halo.

In another embodiment, the invention relates to any of the other embodiments or any combination of the other embodiments wherein $R^2$ is hydrogen.

In another embodiment, the invention relates to any of the other embodiments or any combination of the other embodiments wherein $R^1$ is halo and $R^2$ is hydrogen.

In another embodiment, the invention relates to any of the other embodiments or any combination of the other embodiments wherein Het is selected from (d-3), (d-9) and (d-10); in particular Het is selected from (d-9) and (d-10); more in particular Het is (d-9);

wherein said heterocyclic radicals may be substituted as defined in any of the other embodiments.

In another embodiment, the invention relates to any of the other embodiments or any combination of the other embodiments wherein Het is selected from (d-3), (d-9) and (d-10); wherein radicals (d-3), (d-9) and (d-10) may be substituted with one or more substituents each independently selected from the group consisting of $C_{1-4}$alkyloxy, halo, $C_{1-4}$alkylcarbonyl, $C_{1-4}$alkylthio, $C_{1-4}$alkylsulphonyl, $C_{1-4}$alkylsulphinyl, and $C_{1-4}$alkyl optionally substituted with one or more halo substituents; provided that radicals (d-3), (d-9) and (d-10) are not substituted in the α-positions to the carbon atom of attachment.

In another embodiment, the invention relates to any of the other embodiments or any combination of the other embodiments wherein Het is selected from (d-9) and (d-10); wherein radicals (d-9) and (d-10) may be substituted with one or more substituents each independently selected from the group consisting of $C_{1-4}$alkyloxy, halo, $C_{1-4}$alkylcarbonyl, $C_{1-4}$alkylthio, $C_{1-4}$alkylsulphonyl, $C_{1-4}$alkylsulphinyl, and $C_{1-4}$alkyl optionally substituted with one or more halo substituents; provided that radicals (d-9) and (d-10) are not substituted in the α-positions to the carbon atom of attachment.

In another embodiment, the invention relates to any of the other embodiments or any combination of the other embodiments wherein Het is selected from (d-8), (d-9), (d-10) and (d-11); wherein radicals (d-8), (d-9), (d-10) and (d-11) may be substituted as defined in any of the other embodiments.

In another embodiment, the invention relates to any of the other embodiments or any combination of the other embodiments wherein Het is selected from (d-6), (d-7), (d-8), (d-9), (d-10), (d-11) and (d-12); in particular Het is selected from (d-6), (d-7), (d-8), (d-9), (d-10) and (d-11);
wherein said bicyclic heterocyclic radicals may be substituted as defined in any of the other embodiments.

In another embodiment, the invention relates to any of the other embodiments or any combination of the other embodiments wherein Het is selected from (d-1), (d-2), (d-3), (d-4) and (d-5); in particular Het is selected from (d-3) and (d-5); more in particular Het is (d-3);
wherein said monocyclic heterocyclic radicals may be substituted as defined in any of the other embodiments.

In another embodiment, the invention relates to any of the other embodiments or any combination of the other embodiments wherein Het is selected from (d-1) and (d-2); in particular Het is (d-1);
wherein said monocyclic heterocyclic radicals may be substituted as defined in any of the other embodiments.

In another embodiment, the invention relates to any of the other embodiments or any combination of the other embodiments wherein Het is (d-2); wherein (d-2) may be substituted as defined in any of the other embodiments.

In another embodiment, the invention relates to any of the other embodiments or any combination of the other embodiments wherein Het is (d-5); wherein (d-5) may be substituted as defined in any of the other embodiments.

In another embodiment, the invention relates to any of the other embodiments or any combination of the other embodiments wherein Het is (d-4); wherein (d-4) may be substituted as defined in any of the other embodiments.

In another embodiment, the invention relates to any of the other embodiments or any combination of the other embodiments wherein Het is (d-8); wherein (d-8) may be substituted as defined in any of the other embodiments.

In another embodiment, the invention relates to any of the other embodiments or any combination of the other embodiments wherein Het is (d-10); wherein (d-10) may be substituted as defined in any of the other embodiments.

In another embodiment, the invention relates to any of the other embodiments or any combination of the other embodiments wherein Het is (d-11); wherein (d-11) may be substituted as defined in any of the other embodiments.

In another embodiment, the invention relates to any of the other embodiments or any combination of the other embodiments wherein Het is (d-12).

In another embodiment, the invention relates to any of the other embodiments or any combination of the other embodiments wherein Het is

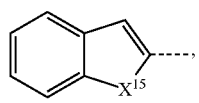

(d-9a)

wherein $X^{15}$ is O or S; in particular O;
wherein (d-9a) may be substituted as defined in any of the other embodiments.

In another embodiment, the invention relates to any of the other embodiments or any combination of the other embodiments wherein Het is selected from

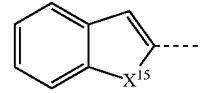

(d-9a)

and

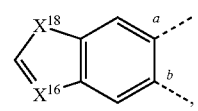

(d-10a)

(d-10a) is attached to the remainder of the molecule with a bond in position a or b;
wherein $X^{15}$ is O or S; in particular O;
wherein $X^{16}$ is CH or N; in particular CH;
wherein $X^{18}$ is NH, S or O; in particular S or O; more in particular O;
wherein radicals (d-9a) and (d-10a) may be substituted as defined in any of the other embodiments.

In another embodiment, the invention relates to any of the other embodiments or any combination of the other embodiments, wherein
$R^5$ and $R^6$ taken together form a bivalent radical —$R^5$-$R^6$—, having formula:

—(CH$_2$)$_s$—      (c), or

—CH=CH—CH=CH—      (d).

In another embodiment, the invention relates to any of the other embodiments or any combination of the other embodiments, wherein
$R^5$ and $R^6$ taken together form a bivalent radical —$R^5$-$R^6$—, having formula:

—CH=CH—CH=CH—      (d).

In another embodiment, the invention relates to any of the other embodiments or any combination of the other embodiments wherein Het is (d-12),
and $R^5$ and $R^6$ taken together form a bivalent radical —$R^5$-$R^6$—, having formula:

—CH=CH—CH=CH—      (d).

In a next embodiment the compound of Formula (I) is selected from the group consisting of:
7-chloro-5,6-dihydro-4-(6-methyl-2-pyridinyl)-4H-pyrrolo[1,2-a][1,4]benzodiazepine,
7-chloro-5,6-dihydro-4-(2-pyridinyl)-4H-pyrrolo[1,2-a][1,4]benzodiazepine,
4-(2-benzofuranyl)-7-chloro-5,6-dihydro-4H-pyrrolo[1,2-a][1,4]benzodiazepine .HCl,
7-chloro-5,6-dihydro-4-(4-pyridinyl)-4H-pyrrolo[1,2-a][1,4]benzodiazepine,
7-chloro-5,6-dihydro-4-(4-pyridinyl)-4H-pyrrolo[1,2-a][1,4]benzodiazepine .HBr,
10-chloro-5,6-dihydro-4-(4-pyridinyl)-4H-pyrrolo[1,2-a][1,4]benzodiazepine .HBr, 9-chloro-5,6-dihydro-4-(4-pyridinyl)-4H-pyrrolo[1,2-a][1,4]benzodiazepine .HBr,
8-chloro-5,6-dihydro-4-(4-pyridinyl)-4H-pyrrolo[1,2-a][1,4]benzodiazepine .HBr,
7-chloro-5,6-dihydro-4-[6-(trifluoromethyl)-3-pyridinyl]-4H-pyrrolo[1,2-a][1,4]benzodiazepine .HCl,
5,6-dihydro-4-[6-(trifluoromethyl)-3-pyridinyl]-4H-pyrrolo[1,2-a][1,4]benzodiazepine .HCl,
4-(2-benzofuranyl)-5,6-dihydro-4H-pyrrolo[1,2-a][1,4]benzodiazepine .HCl,
4-benzo[b]thien-2-yl-7-chloro-5,6-dihydro-4H-pyrrolo[1,2-a][1,4]benzodiazepine .HCl,
4-benzo[b]thien-2-yl-5,6-dihydro-4H-pyrrolo[1,2-a][1,4]benzodiazepine .HCl,
7-chloro-4-(6-ethyl-3-pyridinyl)-5,6-dihydro-4H-pyrrolo[1,2-a][1,4]benzodiazepine .HCl,
4-(2-benzofuranyl)-5,6-dihydro-7-methyl-4H-pyrrolo[1,2-a][1,4]benzodiazepine .HCl,
4-(2-benzothiazolyl)-7-chloro-5,6-dihydro-4H-pyrrolo[1,2-a][1,4]benzodiazepine .HCl,
7-chloro-5,6-dihydro-4-[2-(trifluoromethyl)-5-pyrimidinyl]-4H-pyrrolo[1,2-a][1,4]benzodiazepine .HCl,
4-benzo[b]thien-2-yl-5,6-dihydro-7-methyl-4H-pyrrolo[1,2-a][1,4]benzodiazepine .HCl,
5,6-dihydro-7-methyl-4-[6-(trifluoromethyl)-3-pyridinyl]-4H-pyrrolo[1,2-a][1,4]benzodiazepine .HCl,
7-chloro-4-(5-ethyl-2-pyridinyl)-5,6-dihydro-4H-pyrrolo[1,2-a][1,4]benzodiazepine .HCl,
7-chloro-4-(5-chloro-2-benzofuranyl)-5,6-dihydro-4H-pyrrolo[1,2-a][1,4]benzodiazepine .HCl,
4-(5-chloro-2-benzofuranyl)-5,6-dihydro-7-methyl-4H-pyrrolo[1,2-a][1,4]benzodiazepine .HCl,
7-chloro-5,6-dihydro-4-[6-(trifluoromethyl)-3-pyridazinyl]-4H-pyrrolo[1,2-a][1,4]benzodiazepine .HCl,
7-chloro-5,6-dihydro-4-(6-methyl-2-benzofuranyl)-4H-pyrrolo[1,2-a][1,4]benzodiazepine .HCl,
5,6-dihydro-4-(6-methyl-2-benzofuranyl)-4H-pyrrolo[1,2-a][1,4]benzodiazepine .HCl,
5,6-dihydro-7-methyl-4-(6-methyl-2-benzofuranyl)-4H-pyrrolo[1,2-a][1,4]benzodiazepine .HCl,
7-chloro-5,6-dihydro-4-(2-methyl-5-pyrimidinyl)-4H-pyrrolo[1,2-a][1,4]benzodiazepine .HCl,
7-chloro-4-(1-ethyl-1H-pyrazol-3-yl)-5,6-dihydro-4H-pyrrolo[1,2-a][1,4]benzodiazepine .HBr,
4-benzo[b]thien-2-yl-10-chloro-5,6-dihydro-4H-pyrrolo[1,2-a][1,4]benzodiazepine .HCl,
7,9-dichloro-5,6-dihydro-4-(6-methyl-2-benzofuranyl)-4H-pyrrolo[1,2-a][1,4]benzodiazepine .HCl,
9-chloro-5,6-dihydro-4-(7-methoxy-2-benzofuranyl)-4H-pyrrolo[1,2-a][1,4]benzodiazepine .HCl,
4-benzo[b]thien-2-yl-5,6-dihydro-10-methyl-4H-pyrrolo[1,2-a][1,4]benzodiazepine .HCl,
9-chloro-5,6-dihydro-4-(4-methyl-2-benzofuranyl)-4H-pyrrolo[1,2-a][1,4]benzodiazepine .HCl,
7,9-dichloro-4-(5-fluoro-2-benzofuranyl)-5,6-dihydro-4H-pyrrolo[1,2-a][1,4]benzodiazepine .HCl,
4-benzo[b]thien-2-yl-7,9-dichloro-5,6-dihydro-4H-pyrrolo[1,2-a][1,4]benzodiazepine .HCl,
7-chloro-4-(5-fluoro-2-benzofuranyl)-5,6-dihydro-4H-pyrrolo[1,2-a][1,4]benzodiazepine,
4-(2-benzofuranyl)-5,6-dihydro-10-methyl-4H-pyrrolo[1,2-a][1,4]benzodiazepine .HCl,
7,9-dichloro-5,6-dihydro-4-(5-methoxy-2-benzofuranyl)-4H-pyrrolo[1,2-a][1,4]benzodiazepine .HCl,
9-chloro-5,6-dihydro-4-(5-methoxy-2-benzofuranyl)-4H-pyrrolo[1,2-a][1,4]benzodiazepine .HCl,
7-chloro-5,6-dihydro-4-(5-methoxy-2-benzofuranyl)-4H-pyrrolo[1,2-a][1,4]benzodiazepine .HCl,
4-(2-benzofuranyl)-7,9-dichloro-5,6-dihydro-4H-pyrrolo[1,2-a][1,4]benzodiazepine .HCl
4-benzo[b]thien-2-yl-7-chloro-5,6-dihydro-10-methyl-4H-pyrrolo[1,2-a][1,4]benzodiazepine .HCl,
7,9-dichloro-5,6-dihydro-4-(7-methoxy-2-benzofuranyl)-4H-pyrrolo[1,2-a][1,4]benzodiazepine .HCl,
7-chloro-5,6-dihydro-4-(4-methyl-2-benzofuranyl)-4H-pyrrolo[1,2-a][1,4]benzodiazepine .HCl,
7-chloro-5,6-dihydro-10-methyl-4-[2-(trifluoromethyl)-5-pyrimidinyl]-4H-pyrrolo[1,2-a][1,4]benzodiazepine . HCl,
7-fluoro-5,6-dihydro-4-[6-(trifluoromethyl)-3-pyridinyl]-4H-pyrrolo[1,2-a][1,4]benzodiazepine .HCl,
7,9-dichloro-5,6-dihydro-4-[6-(trifluoromethyl)-3-pyridinyl]-4H-pyrrolo[1,2-a][1,4]benzodiazepine .HCl,
9-chloro-4-(5-fluoro-2-benzofuranyl)-5,6-dihydro-4H-pyrrolo[1,2-a][1,4]benzodiazepine .HCl,
7-chloro-5,6-dihydro-4-(2-methyl-6-benzoxazolyl)-4H-pyrrolo[1,2-a][1,4]benzodiazepine .HCl,
7-chloro-4-(6-chlorofuro[3,2-c]pyridin-2-yl)-5,6-dihydro-4H-pyrrolo[1,2-a][1,4]benzodiazepine .HCl,
7-chloro-4-(3-chlorobenzo[b]thien-5-yl)-5,6-dihydro-4H-pyrrolo[1,2-a][1,4]benzodiazepine .HCl,
4-(2-benzofuranyl)-10-chloro-5,6-dihydro-4H-pyrrolo[1,2-a][1,4]benzodiazepine,
7-chloro-5,6-dihydro-4-(7-methyl-2-benzofuranyl)-4H-pyrrolo[1,2-a][1,4]benzodiazepine,
7-chloro-4-(1-ethyl-1H-pyrazol-4-yl)-6H-pyrrolo[1,2-a][1,4]benzodiazepine,
4-(2-benzofuranyl)-7-chloro-6H-pyrrolo[1,2-a][1,4]benzodiazepine,
8,10-dichloro-4-(1-ethyl-1H-pyrazol-4-yl)-6H-pyrrolo[1,2-a][1,4]benzodiazepine,
7,10-dichloro-4-(1-ethyl-1H-pyrazol-4-yl)-6H-pyrrolo[1,2-a][1,4]benzodiazepine,
7-chloro-4-[6-(trifluoromethyl)-3-pyridinyl]-6H-pyrrolo[1,2-a][1,4]benzodiazepine,
4-benzo[b]thien-2-yl-7-chloro-6H-pyrrolo[1,2-a][1,4]benzodiazepine,
4-benzo[b]thien-2-yl-6H-pyrrolo[1,2-a][1,4]benzodiazepine,
4-[6-(trifluoromethyl)-3-pyridinyl]-6H-pyrrolo[1,2-a][1,4]benzodiazepine,
4-(2-benzofuranyl)-6H-pyrrolo[1,2-a][1,4]benzodiazepine,
7-chloro-4-[2-(trifluoromethyl)-5-pyrimidinyl]-6H-pyrrolo[1,2-a][1,4]benzodiazepine,
7-methyl-4-[6-(trifluoromethyl)-3-pyridinyl]-6H-pyrrolo[1,2-a][1,4]benzodiazepine,
4-(5-chloro-2-benzofuranyl)-7-methyl-6H-pyrrolo[1,2-a][1,4]benzodiazepine,
4-(2-benzofuranyl)-7-methyl-6H-pyrrolo[1,2-a][1,4]benzodiazepine,
4-benzo[b]thien-2-yl-7-methyl-6H-pyrrolo[1,2-a][1,4]benzodiazepine,
7,8-dichloro-4-(6-ethyl-3-pyridinyl)-6H-pyrrolo[1,2-a][1,4]benzodiazepine,
4-(2-benzothiazolyl)-7-chloro-6H-pyrrolo[1,2-a][1,4]benzodiazepine,
4-(2-benzothiazolyl)-7-chloro-6H-pyrrolo[1,2-a][1,4]benzodiazepine, .HCl 7-methyl-4-(2-methyl-5-pyrimidinyl)-6H-pyrrolo[1,2-a][1,4]benzodiazepine,
7-chloro-4-(2-methyl-4-pyridinyl)-6H-pyrrolo[1,2-a][1,4]benzodiazepine,
7-chloro-4-(6-methyl-2-benzofuranyl)-6H-pyrrolo[1,2-a][1,4]benzodiazepine,
4-(6-methyl-2-benzofuranyl)-6H-pyrrolo[1,2-a][1,4]benzodiazepine,
7-chloro-4-(2-methyl-5-pyrimidinyl)-6H-pyrrolo[1,2-a][1,4]benzodiazepine,
7-chloro-4-(5-chloro-2-benzofuranyl)-6H-pyrrolo[1,2-a][1,4]benzodiazepine,
4-(6-benzofuranyl)-7-chloro-6H-pyrrolo[1,2-a][1,4]benzodiazepine,
7-methyl-4-(6-methyl-2-benzofuranyl)-6H-pyrrolo[1,2-a][1,4]benzodiazepine,
4-benzo[b]thien-2-yl-9-chloro-6H-pyrrolo[1,2-a][1,4]benzodiazepine,
7-chloro-4-(5-methyl-2-benzofuranyl)-6H-pyrrolo[1,2-a][1,4]benzodiazepine,
4-(6-benzofuranyl)-7,10-dichloro-6H-pyrrolo[1,2-a][1,4]benzodiazepine,
9-chloro-4-(5-methyl-2-benzofuranyl)-6H-pyrrolo[1,2-a][1,4]benzodiazepine,
4-benzo[b]thien-2-yl-10-chloro-6H-pyrrolo[1,2-a][1,4]benzodiazepine,
4-(2-benzofuranyl)-9-chloro-6H-pyrrolo[1,2-a][1,4]benzodiazepine,
4-(2-benzofuranyl)-10-chloro-6H-pyrrolo[1,2-a][1,4]benzodiazepine,
7,9-dichloro-4-(5-ethyl-2-pyridinyl)-6H-pyrrolo[1,2-a][1,4]benzodiazepine,
7-chloro-4-(5-ethyl-2-pyridinyl)-6H-pyrrolo[1,2-a][1,4]benzodiazepine,
4-(2-methyl-4-pyridinyl)-6H-pyrrolo[1,2-a][1,4]benzodiazepine,
7-methyl-4-(2-methyl-4-pyridinyl)-6H-pyrrolo[1,2-a][1,4]benzodiazepine,
4-(6-benzothiazolyl)-7-methyl-6H-pyrrolo[1,2-a][1,4]benzodiazepine,
4-(7-methoxy-2-benzofuranyl)-6H-pyrrolo[1,2-a][1,4]benzodiazepine,
7-methyl-4-(7-methyl-2-benzofuranyl)-6H-pyrrolo[1,2-a][1,4]benzodiazepine,
4-(6-benzothiazolyl)-6H-pyrrolo[1,2-a][1,4]benzodiazepine,
4-(7-methyl-2-benzofuranyl)-6H-pyrrolo[1,2-a][1,4]benzodiazepine,
7-chloro-4-(7-methyl-2-benzofuranyl)-6H-pyrrolo[1,2-a][1,4]benzodiazepine,
4-(7-methoxy-2-benzofuranyl)-7-methyl-6H-pyrrolo[1,2-a][1,4]benzodiazepine,
4-(6-benzothiazolyl)-7-chloro-6H-pyrrolo[1,2-a][1,4]benzodiazepine,
4-[2-(trifluoromethyl)-5-pyrimidinyl]-6H-pyrrolo[1,2-a][1,4]benzodiazepine,
7-chloro-4-(2-ethyl-4-thiazolyl)-6H-pyrrolo[1,2-a][1,4]benzodiazepine,
7-chloro-4-(7-methoxy-2-benzofuranyl)-6H-pyrrolo[1,2-a][1,4]benzodiazepine,
7-chloro-4-(1-methyl-1H-indol-6-yl)-6H-pyrrolo[1,2-a][1,4]benzodiazepine,
7-chloro-4-(1-methyl-1H-indol-5-yl)-6H-pyrrolo[1,2-a][1,4]benzodiazepine,
7,9-dichloro-4-(5-methyl-2-benzofuranyl)-6H-pyrrolo[1,2-a][1,4]benzodiazepine,
7,9-dichloro-4-(6-methyl-2-benzofuranyl)-6H-pyrrolo[1,2-a][1,4]benzodiazepine,
7-chloro-4-(3-ethyl-5-isoxazolyl)-6H-pyrrolo[1,2-a][1,4]benzodiazepine,
4-benzo[b]thien-2-yl-10-methyl-6H-pyrrolo[1,2-a][1,4]benzodiazepine,
9-chloro-4-(7-methoxy-2-benzofuranyl)-6H-pyrrolo[1,2-a][1,4]benzodiazepine,
7,9-dichloro-4-(2-ethyl-4-thiazolyl)-6H-pyrrolo[1,2-a][1,4]benzodiazepine,
7-chloro-4-(6-ethyl-3-pyridinyl)-6H-pyrrolo[1,2-a][1,4]benzodiazepine,
4-benzo[b]thien-2-yl-7,9-dichloro-6H-pyrrolo[1,2-a][1,4]benzodiazepine,
7,9-dichloro-4-(1-methyl-1H-indol-5-yl)-6H-pyrrolo[1,2-a][1,4]benzodiazepine,
7,9-dichloro-4-(6-ethyl-3-pyridinyl)-6H-pyrrolo[1,2-a][1,4]benzodiazepine,
4-(2-benzofuranyl)-10-methyl-6H-pyrrolo[1,2-a][1,4]benzodiazepine,
7-chloro-4-(5-methoxy-2-benzofuranyl)-6H-pyrrolo[1,2-a][1,4]benzodiazepine,
4-(2-benzofuranyl)-7,9-dichloro-6H-pyrrolo[1,2-a][1,4]benzodiazepine,
7-chloro-4-(5-fluoro-2-benzofuranyl)-6H-pyrrolo[1,2-a][1,4]benzodiazepine,
7,9-dichloro-4-(5-methoxy-2-benzofuranyl)-6H-pyrrolo[1,2-a][1,4]benzodiazepine,
7,9-dichloro-4-(5-fluoro-2-benzofuranyl)-6H-pyrrolo[1,2-a][1,4]benzodiazepine,
9-chloro-4-(4-methyl-2-benzofuranyl)-6H-pyrrolo[1,2-a][1,4]benzodiazepine,
7-methyl-4-[2-(trifluoromethyl)-5-pyrimidinyl]-6H-pyrrolo[1,2-a][1,4]benzodiazepine,
10-chloro-4-(7-methoxy-2-benzofuranyl)-6H-pyrrolo[1,2-a][1,4]benzodiazepine,
9-chloro-4-(5-methoxy-2-benzofuranyl)-6H-pyrrolo[1,2-a][1,4]benzodiazepine,
4-(6-benzothiazolyl)-9-chloro-6H-pyrrolo[1,2-a][1,4]benzodiazepine,
4-(6-benzothiazolyl)-10-chloro-6H-pyrrolo[1,2-a][1,4]benzodiazepine,
7-chloro-4-(4-methyl-2-benzofuranyl)-6H-pyrrolo[1,2-a][1,4]benzodiazepine,
7-chloro-4-(4-ethyl-2-thiazolyl)-6H-pyrrolo[1,2-a][1,4]benzodiazepine,
7,9-dichloro-4-(4-ethyl-2-thiazolyl)-6H-pyrrolo[1,2-a][1,4]benzodiazepine,
7-chloro-4-(5-ethyl-2-thiazolyl)-6H-pyrrolo[1,2-a][1,4]benzodiazepine,
4-benzo[b]thien-2-yl-7-chloro-10-methyl-6H-pyrrolo[1,2-a][1,4]benzodiazepine,
7,9-dichloro-4-(7-methoxy-2-benzofuranyl)-6H-pyrrolo[1,2-a][1,4]benzodiazepine,
7,9-dichloro-4-(5-ethyl-2-thiazolyl)-6H-pyrrolo[1,2-a][1,4]benzodiazepine,
7-fluoro-4-[6-(trifluoromethyl)-3-pyridinyl]-6H-pyrrolo[1,2-a][1,4]benzodiazepine,
4-(6-benzothiazolyl)-7,9-dichloro-6H-pyrrolo[1,2-a][1,4]benzodiazepine,
7-chloro-4-(5,7-difluoro-2-benzofuranyl)-6H-pyrrolo[1,2-a][1,4]benzodiazepine,
7,9-dichloro-4-(7-fluoro-2-benzofuranyl)-6H-pyrrolo[1,2-a][1,4]benzodiazepine,
4-(2,1,3-benzothiadiazol-5-yl)-7-chloro-6H-pyrrolo[1,2-a][1,4]benzodiazepine, 7,9-dichloro-4-[2-(trifluoromethyl)-5-pyrimidinyl]-6H-pyrrolo[1,2-a][1,4]benzodiazepine,
7,9-dichloro-4-[6-(trifluoromethyl)-3-pyridinyl]-6H-pyrrolo[1,2-a][1,4]benzodiazepine,
9-chloro-4-(5-fluoro-2-benzofuranyl)-6H-pyrrolo[1,2-a][1,4]benzodiazepine,
7,9-dichloro-4-(5,7-difluoro-2-benzofuranyl)-6H-pyrrolo[1,2-a][1,4]benzodiazepine,
7,9-dichloro-4-(2-methyl-2H-1,2,3-benzotriazol-5-yl)-6H-pyrrolo[1,2-a][1,4]benzodiazepine,
7-chloro-4-(7-chloro-2-benzofuranyl)-6H-pyrrolo[1,2-a][1,4]benzodiazepine,
7-chloro-4-(7-fluoro-2-benzofuranyl)-6H-pyrrolo[1,2-a][1,4]benzodiazepine,
7-chloro-4-(2-methyl-2H-1,2,3-benzotriazol-5-yl)-6H-pyrrolo[1,2-a][1,4]benzodiazepine,
7-chloro-4-(7-fluorobenzo[b]thien-2-yl)-6H-pyrrolo[1,2-a][1,4]benzodiazepine,
7,9-dichloro-4-(7-fluorobenzo[b]thien-2-yl)-6H-pyrrolo[1,2-a][1,4]benzodiazepine,
7-chloro-4-(1-methyl-1H-1,2,3-benzotriazol-6-yl)-6H-pyrrolo[1,2-a][1,4]benzodiazepine,
7,9-dichloro-4-(1-methyl-1H-1,2,3-benzotriazol-6-yl)-6H-pyrrolo[1,2-a][1,4]benzodiazepine,
4-(5-benzofuranyl)-7-chloro-6H-pyrrolo[1,2-a][1,4]benzodiazepine,
7-chloro-4-(6-chloro-3-pyridinyl)-6H-pyrrolo[1,2-a][1,4]benzodiazepine,
4-(1,2,3-benzothiadiazol-5-yl)-7-chloro-6H-pyrrolo[1,2-a][1,4]benzodiazepine,
7-chloro-4-(2-methyl-5-benzothiazolyl)-6H-pyrrolo[1,2-a][1,4]benzodiazepine,
7-chloro-4-(5,6-dichloro-3-pyridinyl)-6H-pyrrolo[1,2-a][1,4]benzodiazepine,
4-benzo[b]thien-5-yl-7-chloro-6H-pyrrolo[1,2-a][1,4]benzodiazepine,
4-(7-chloro-6H-pyrrolo[1,2-a][1,4]benzodiazepin-4-yl)-1-(1-methylethyl)-2(1H)-pyridinone,
7-fluoro-4-(2-methyl-6-quinolinyl)-6H-pyrrolo[1,2-a][1,4]benzodiazepine,
7-chloro-4-(2-methyl-6-quinolinyl)-6H-pyrrolo[1,2-a][1,4]benzodiazepine,
4-(5,6-dichloro-3-pyridinyl)-7-fluoro-6H-pyrrolo[1,2-a][1,4]benzodiazepine,
4-(5,6-dichloro-3-pyridinyl)-7,9-difluoro-6H-pyrrolo[1,2-a][1,4]benzodiazepine,
7-chloro-4-(6-chloro-3-pyridinyl)-9-fluoro-6H-pyrrolo[1,2-a][1,4]benzodiazepine,
7-chloro-4-[6-(1,1-difluoroethyl)-3-pyridinyl]-6H-pyrrolo[1,2-a][1,4]benzodiazepine,
1-[5-(7-chloro-6H-pyrrolo[1,2-a][1,4]benzodiazepin-4-yl)-2-pyridinyl]-ethanone,
4-[6-(1,1-difluoroethyl)-3-pyridinyl]-7-fluoro-6H-pyrrolo[1,2-a][1,4]benzodiazepine,
4-[6-(1,1-difluoroethyl)-3-pyridinyl]-7,9-difluoro-6H-pyrrolo[1,2-a][1,4]benzodiazepine,
4-(5-chlorofuro[2,3-b]pyridin-2-yl)-7,9-difluoro-6H-pyrrolo[1,2-a][1,4]benzodiazepine,
7,9-difluoro-4-(2-methyl-6-quinolinyl)-6H-pyrrolo[1,2-a][1,4]benzodiazepine,
7-chloro-4-(6,7-dihydro-5H-cyclopenta[b]pyridin-3-yl)-6H-pyrrolo[1,2-a][1,4]benzodiazepine,
7,9-dichloro-4-[6-(1,1-difluoroethyl)-3-pyridinyl]-6H-pyrrolo[1,2-a][1,4]benzodiazepine,
1-[5-(7,9-difluoro-6H-pyrrolo[1,2-a][1,4]benzodiazepin-4-yl)-2-pyridinyl]-ethanone,
4-benzo[b]thien-5-yl-10-chloro-6H-pyrrolo[1,2-a][1,4]benzodiazepine,
7-chloro-4-[6-(1,1-difluoroethyl)-3-pyridinyl]-9-fluoro-6H-pyrrolo[1,2-a][1,4]benzodiazepine,
4-benzo[b]thien-5-yl-7-fluoro-6H-pyrrolo[1,2-a][1,4]benzodiazepine,
4-benzo[b]thien-5-yl-9-chloro-6H-pyrrolo[1,2-a][1,4]benzodiazepine,
4-benzo[b]thien-5-yl-7,9-difluoro-6H-pyrrolo[1,2-a][1,4]benzodiazepine,
1-[5-(7-fluoro-6H-pyrrolo[1,2-a][1,4]benzodiazepin-4-yl)-2-pyridinyl]-ethanone,
4-benzo[b]thien-6-yl-7-chloro-6H-pyrrolo[1,2-a][1,4]benzodiazepine,
7-chloro-4-furo[2,3-b]pyridin-5-yl-6H-pyrrolo[1,2-a][1,4]benzodiazepine,
7-chloro-4-(2-methyl-6-benzoxazolyl)-6H-pyrrolo[1,2-a][1,4]benzodiazepine,
7-chloro-4-[2-(trifluoromethyl)-4-pyridinyl]-6H-pyrrolo[1,2-a][1,4]benzodiazepine,
4-(5-benzothiazolyl)-7-chloro-6H-pyrrolo[1,2-a][1,4]benzodiazepine,
7-chloro-4-(6-chlorofuro[3,2-c]pyridin-2-yl)-6H-pyrrolo[1,2-a][1,4]benzodiazepine,
7-chloro-4-(5-chloro-7-methylfuro[2,3-c]pyridin-2-yl)-6H-pyrrolo[1,2-a][1,4]benzodiazepine,
4-(5-benzothiazolyl)-7-fluoro-6H-pyrrolo[1,2-a][1,4]benzodiazepine,
7-chloro-4-(3-chloro-5-benzofuranyl)-6H-pyrrolo[1,2-a][1,4]benzodiazepine,
4-(5-benzothiazolyl)-7,9-difluoro-6H-pyrrolo[1,2-a][1,4]benzodiazepine,
7-fluoro-4-[2-(trifluoromethyl)-5-benzothiazolyl]-6H-pyrrolo[1,2-a][1,4]benzodiazepine,
7-chloro-4-[2-(trifluoromethyl)-5-benzothiazolyl]-6H-pyrrolo[1,2-a][1,4]benzodiazepine,
9-chloro-4-[2-(trifluoromethyl)-4-pyridinyl]-6H-pyrrolo[1,2-a][1,4]benzodiazepine,
7-chloro-4-(3-chlorobenzo[b]thien-5-yl)-6H-pyrrolo[1,2-a][1,4]benzodiazepine,
7-chloro-4-(3-chloro-6-benzofuranyl)-6H-pyrrolo[1,2-a][1,4]benzodiazepine,
4-(3-chloro-5-benzofuranyl)-7,9-difluoro-6H-pyrrolo[1,2-a][1,4]benzodiazepine,
4-(3-chloro-5-benzofuranyl)-7-fluoro-6H-pyrrolo[1,2-a][1,4]benzodiazepine,
4-(10-chloro-6H-pyrrolo[1,2-a][1,4]benzodiazepin-4-yl)-1-(1-methylethyl)-2(1H)-pyridinone,
7-chloro-4-(2-chloro-5-benzofuranyl)-6H-pyrrolo[1,2-a][1,4]benzodiazepine,
9-chloro-4-(3-chlorobenzo[b]thien-5-yl)-6H-pyrrolo[1,2-a][1,4]benzodiazepine,
10-chloro-4-(3-chlorobenzo[b]thien-5-yl)-6H-pyrrolo[1,2-a][1,4]benzodiazepine,
7-chloro-4-(3-quinolinyl)-6H-pyrrolo[1,2-a][1,4]benzodiazepine,
4-(3-quinolinyl)-6H-pyrrolo[1,2-a][1,4]benzodiazepine,
9-chloro-4-(4-pyridinyl)-6H-pyrrolo[1,2-a][1,4]benzodiazepine, 4-(1H-benzimidazol-6-yl)-9-chloro-6H-pyrrolo[1,2-a][1,4]benzodiazepine,
4-(1H-benzimidazol-6-yl)-7-chloro-6H-pyrrolo[1,2-a][1,4]benzodiazepine,
9-chloro-4-(3-quinolinyl)-6H-pyrrolo[1,2-a][1,4]benzodiazepine,
7-chloro-4-(6-quinoxalinyl)-6H-pyrrolo[1,2-a][1,4]benzodiazepine,
7-chloro-5,6-dihydro-4-(6-quinoxalinyl)-4H-pyrrolo[1,2-a][1,4]benzodiazepine .HCl,
9-chloro-4-(3-chlorobenzo[b]thien-5-yl)-5,6-dihydro-4H-pyrrolo[1,2-a][1,4]benzodiazepine,
10-chloro-5,6-dihydro-4-(7-methoxy-2-benzofuranyl)-4H-pyrrolo[1,2-a][1,4]benzodiazepine,
7-chloro-5,6-dihydro-4-(7-methoxy-2-benzofuranyl)-4H-pyrrolo[1,2-a][1,4]benzodiazepine .HCl,
5,6-dihydro-4-(7-methoxy-2-benzofuranyl)-7-methyl-4H-pyrrolo[1,2-a][1,4]benzodiazepine .HCl,
5,6-dihydro-4-(7-methyl-2-benzofuranyl)-4H-pyrrolo[1,2-a][1,4]benzodiazepine .HCl,
5,6-dihydro-7-methyl-4-(7-methyl-2-benzofuranyl)-4H-pyrrolo[1,2-a][1,4]benzodiazepine .HCl,
7-chloro-4-(1-ethyl-1H-pyrazol-4-yl)-5,6-dihydro-4H-pyrrolo[1,2-a][1,4]benzodiazepine .HCl,
7,10-dichloro-4-(1-ethyl-1H-pyrazol-4-yl)-5,6-dihydro-4H-pyrrolo[1,2-a][1,4]benzodiazepine .HCl,
8,10-dichloro-4-(1-ethyl-1H-pyrazol-4-yl)-5,6-dihydro-4H-pyrrolo[1,2-a][1,4]benzodiazepine .HCl,
4-(2-benzofuranyl)-9-chloro-5,6-dihydro-4H-pyrrolo[1,2-a][1,4]benzodiazepine .HCl,
4-benzo[b]thien-2-yl-9-chloro-5,6-dihydro-4H-pyrrolo[1,2-a][1,4]benzodiazepine .HCl,
7-chloro-4-(3-pyridinyl)-6H-pyrrolo[1,2-a][1,4]benzodiazepine,
7-chloro-4-(2-quinolinyl)-6H-pyrrolo[1,2-a][1,4]benzodiazepine, and
7-chloro-4-(4-pyridinyl)-6H-pyrrolo[1,2-a][1,4]benzodiazepine,
including stereoisomeric forms thereof,
and the free bases, the pharmaceutically acceptable addition salts and the solvates thereof.

The present invention also encompasses processes for the preparation of compounds of Formula (I) and subgroups thereof.

The compounds of Formula (I) and the subgroups thereof can be prepared by a succession of steps as described hereunder. They are generally prepared from starting materials which are either commercially available or prepared by standard means obvious to those skilled in the art. The compounds of the present invention can be also prepared using standard synthetic processes commonly used by those skilled in the art of organic chemistry.

The person skilled in the art will realize that for some reactions anhydrous conditions need to be applied and/or an inert protecting atmosphere such as, for example, N$_2$ or argon, must be used.

The compounds of the present invention, can be prepared according to Scheme 1:

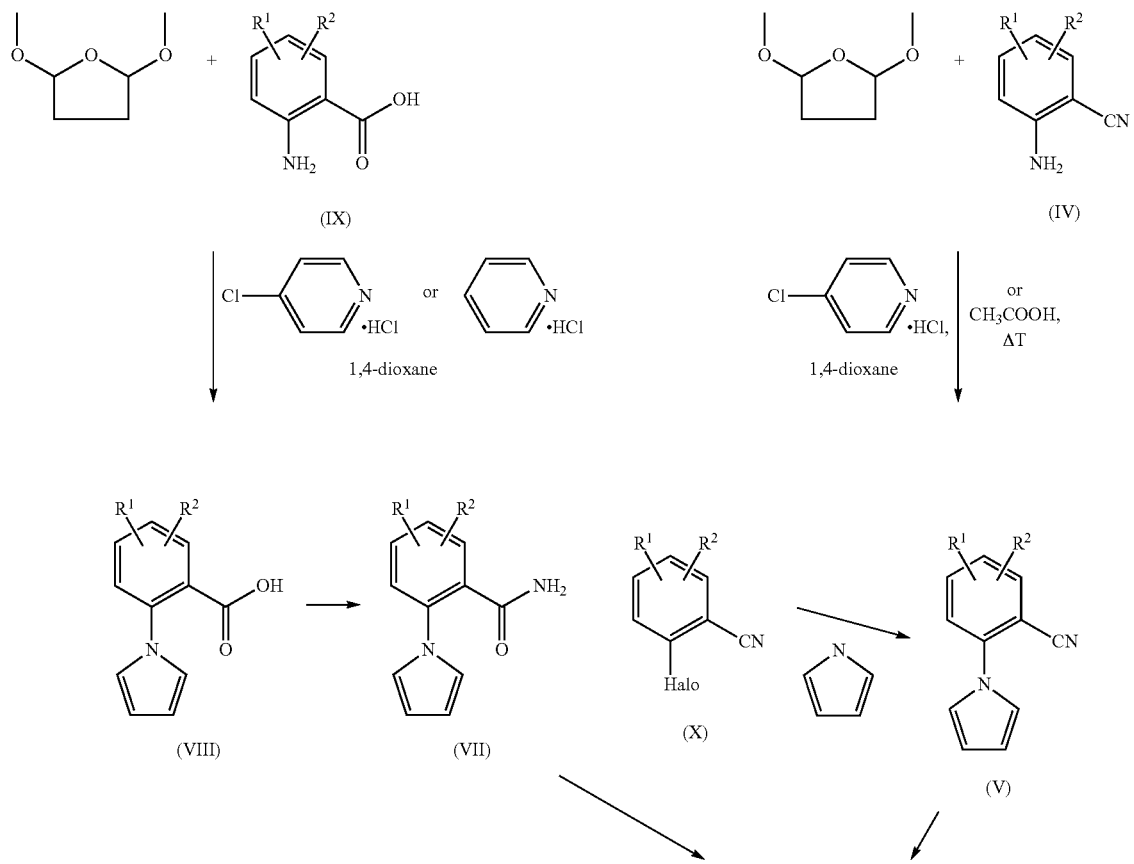

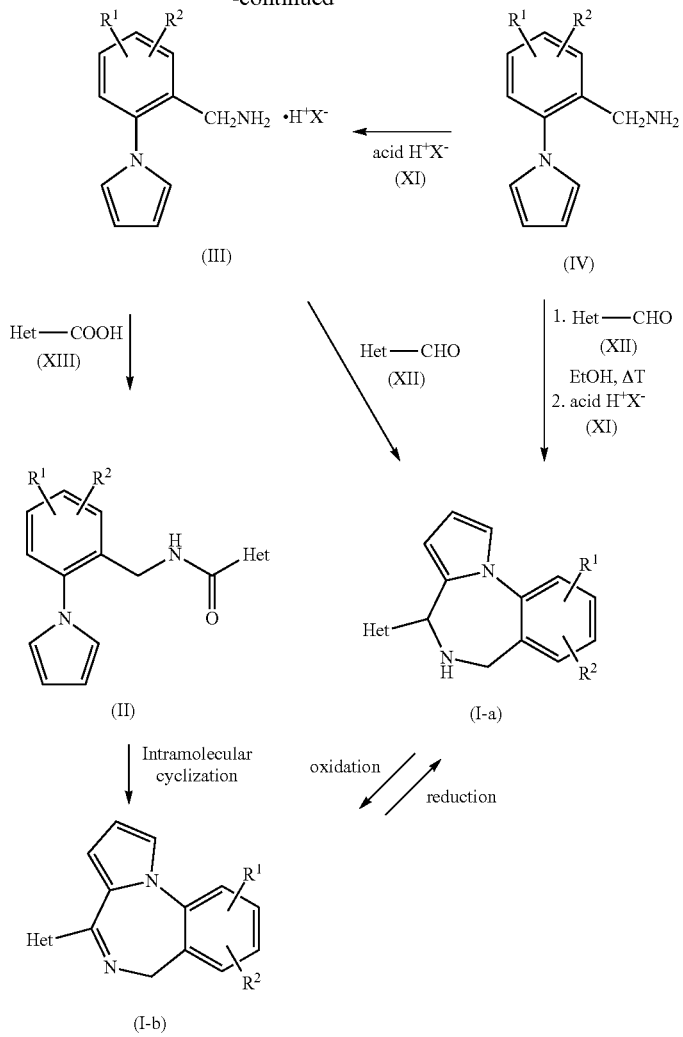

The compounds of Formula (I) wherein $R^3$ and $R^4$ together form an extra bond, said compounds being represented by formula (I-b), can be prepared from the compounds represented by the formula (I-a), following art-known amine to imine oxidation reactions. These oxidation reactions may be conducted by reacting a compound of formula (I-a) with an oxidant such as, for example, lead tetra-acetate or manganese dioxide, in a reaction inert solvent such as a halogenated hydrocarbon e.g. dichloromethane (DCM) or trichloromethane. The reaction rate can be enhanced by stirring and optionally heating the reaction mixture.

Alternatively, a compound of formula (I-b) can be prepared by an intramolecular cyclization of an intermediate of formula (II). In the presence of an acid such as, for example, $POCl_3$, the amide in the intermediate of formula (II) can function as a C-electrophile, resulting in a ring closure. The reaction may be performed in a suitable solvents such as, for example, DCM ($CH_2Cl_2$). Stirring and heating may enhance the rate of the reaction.

A compound of formula (I-a) can be prepared from an intermediate of formula (IV) by converting it in a salt (III) by reaction with an acid $H^+X^-$ of formula (XI), and reacting said salt of formula (III) with an aldehyde of formula (XII) in an appropriate solvent such as an alcohol, e.g. methanol (MeOH), ethanol (EtOH), isopropanol, at an elevated temperature, preferably at reflux temperature.

Alternatively, the intermediate of formula (IV) may be reacted first with the aldehyde of formula (XII) and the thus formed imine may be cyclized in the presence of an acid $H^+X^-$ of formula (XI) to a compound of formula (I-a).

Alternatively, a compound of formula (I-a) may be obtained by the reduction of a compound of formula (I-b) by using methods well-known to those skilled in the art.

Some compounds of formula (I-b) can be converted to other compounds of formula (I-b). For example, compounds of formula (I-b) wherein Het is selected from (d-1)-(d-11) and wherein Het is substituted with $C_{1-4}$alkylsulphonyl can be prepared by oxidation of the sulphur group in a compound of formula (I-b) wherein Het is selected from (d-1)-(d-11) and wherein Het is substituted with $C_{1-4}$alkylthio. Typically, this reaction can be carried out in the presence of an oxidizing agent such as oxone and a suitable solvent such as, for example, THF.

An intermediate of formula (II) may be prepared by a coupling reaction between an intermediate of formula (III) and (XIII). Said reaction may be performed in the presence of coupling agents such as typically 1-hydroxy-1H-benzotriazole (HOBT) and N'-(ethylcarbonimidoyl)-N,N-dimethyl-1,3-propanediamine monohydrochloride (EDCI). The reaction may be performed in the presence of a base such as triethylamine (Et$_3$N) and a suitable solvent such as, for example, DCM. Alternatively, an acid chloride derivative of (XIII) or a reactive ester derivative of (XIII) can also be used in this type of reaction to prepare an intermediate of formula (II).

An intermediate of formula (XIII) or its acid chloride or ester derivative, can be easily prepared by those skilled in the art.

Intermediates of formula (III) and (IV) are prepared by reducing a 1-(2-cyano-phenyl)pyrrole derivative of formula (V). Several procedures well-known to those skilled in the art may be used to reduce the nitrile function such as, for example:

1. LiAlH$_4$/THF [S. Raines, S. Y. Chai and F. P. Palopoli; J. Heterocyclic Chem., 13, 711-716 (1976)]
2. i. sodium bis(2-methoxyethoxy)aluminate (Red-Al®) 70% w/w Toluene, RT:
    ii. NaOH 10%, RT [G. W. H. Cheeseman and S. G. Greenberg; J. Heterocyclic Chem., 16, 241-244(1979)]
3a. i. KBH$_4$/CF$_3$COOH, THF; ii. H$_2$O; iii. HCl[P. Trinka, P. Slégel and J. Reiter; J. Prakt. Chem., 338, 675-678(1996)]
3b. Borane-dimethyl sulfide (1:1), THF
4a. RaNi (Raney Nickel)/H$_2$
4b. RaNi/thiophene solution/(MeOH/NH$_3$)

Even other well-known methods for reducing the nitrile function may also be used.

An intermediate of formula (V) in turn is commercially available or alternatively can be easily prepared by, for example, treating a 2-aminobenzonitrile derivative of formula (VI) with tetrahydro-2,5-dimethoxyfuran in an inert solvent such as dioxane or tetrahydrofuran (THF) in the presence of an acid such as 4-chloropyridine hydrochloride, or in an acidic solvent such as glacial acetic acid, at an elevated temperature, preferably at reflux temperature. Alternatively, an intermediate of formula (V) can also be prepared from an intermediate of formula (X). Typically, an intermediate of formula (X) wherein Halo is defined as Br, I, Cl or F, is reacted with pyrrole in the presence of a base such as, for example, Cs$_2$CO$_3$ or NaH, in a suitable solvent such as typically N,N-dimethylformamide (DMF).

Alternatively, an intermediate of formula (IV) may be prepared by treating an intermediate of formula (VII) with borane-dimethyl sulfide (1:1) in a suitable solvent such as, for example, THF. The reaction typically can be performed in the presence of an acid such as HCl. After the reaction has proceeded, the reaction mixture can be basified with a suitable base such as NaOH. The reaction can be performed at an elevated temperature, preferably at reflux temperature.

An intermediate of formula (VII) can be prepared from an intermediate of formula (VIII). An intermediate of formula (VIII) can be reacted with a nitrogen source such as, NH$_3$.H$_2$O in the presence of HOBT and EDCI. This type of reaction typically can be performed in a suitable solvent like DMF. Stirring of the reaction mixture may enhance the rate of reaction.

An intermediate of formula (VIII) can be easily prepared by treating an intermediate of formula (IX) with tetrahydro-2,5-dimethoxyfuran in an inert solvent such as dioxane in the presence of an acid such as pyridine hydrochloride (1:1) at an elevated temperature, preferably at reflux temperature. Alternatively, a reactive ester derivative of (IX) can also be used in this type of reaction to prepare an intermediate of formula (VIII).

All starting materials are commercially available or can be easily prepared by those skilled in the art. The synthesis of some of the starting materials is exemplified in the experimental part.

In all these preparations, the reaction products may be isolated from the reaction medium and, if necessary, further purified according to methodologies generally known in the art such as, for example, extraction, crystallization, trituration and chromatography. In particular, stereoisomers can be isolated chromatographically using a chiral stationary phase such as, for example, Chiralpak® AD (amylose 3,5 dimethylphenyl carbamate) or Chiralpak® AS, both purchased from Daicel Chemical Industries, Ltd, in Japan.

Pure stereoisomeric forms of the compounds and the intermediates of this invention may be obtained by the application of art-known procedures. Enantiomers may be separated from each other by the selective crystallization of their diastereomeric salts with optically active acids. Alternatively, enantiomers may be separated by chromatographic techniques using chiral stationary phases. Said pure stereoisomeric forms may also be derived from the corresponding pure stereoisomeric forms of the appropriate starting materials, provided that the reaction occurs stereoselectively or stereospecifically. Preferably if a specific stereoisomer is desired, said compound will be synthesized by stereoselective or stereospecific methods of preparation. These methods will advantageously employ chirally pure starting materials. Stereoisomeric forms of the compounds of Formula (I) are obviously intended to be included within the scope of the invention.

The chirally pure forms of the compounds of Formula (I) form a preferred group of compounds. It is therefore that the chirally pure forms of the intermediates and their salt forms are particularly useful in the preparation of chirally pure compounds of Formula (I). Also enantiomeric mixtures of the intermediates are useful in the preparation of compounds of Formula (I) with the corresponding configuration.

The compounds of Formula (I) and stereoisomeric forms thereof, and the pharmaceutically acceptable addition salts, and the solvates thereof, may be active against dematiaceous hyphomycetes, dimorphic pathogens, dermatophytes, zygomycetes, hyaline hyphomycetes, yeasts and yeastlike organisms.

The compounds of Formula (I) and stereoisomeric forms thereof, and the pharmaceutically acceptable addition salts, and the solvates thereof, may be active against dimorphic pathogens, yeasts and yeastlike organisms.

The compounds of Formula (I) and stereoisomeric forms thereof, and the pharmaceutically acceptable addition salts, and the solvates thereof, may be active against moulds.

The compounds of Formula (I) and stereoisomeric forms thereof, and the pharmaceutically acceptable addition salts, and the solvates thereof, may be active against a wide variety of fungi, such as *Candida* spp., e.g. *Candida albicans, Candida glabrata, Candida krucei; Candida parapsilosis, Candida kefyr, Candida tropicalis; Aspergillus* spp., e.g. *Aspergillus fumigatus, Aspergillus niger, Aspergillus flavus; Cryptococcus neoformans; Sporothrix schenckii; Epidermophyton floccosum; Microsporum* spp., e.g. *Microsporum canis, Microsporum gypseum; Trichophyton* spp., e.g. *Trichophyton mentagrophytes, Trichophyton rubrum, Trichophyton quinckeanum, Trichophyton tonsurans, Trichophyton verrucosum, Trichophyton violaceum, Trichophyton interdigitale, Trichophyton soudanense; Fusarium* spp., e.g. *Fusarium solani, Fusarium oxysporum, Fusarium proliferatum, Fusarium verticillioides; Rhizomucor* spp., e.g. *Rhizomucor miehei, Rhizomucor pusillus;*

Mucor circinelloides; Rhizopus spp., e.g. Rhizopus oryzae, Rhizopus microspores; Malassezia furfur; Acremonium spp.; Paecilomyces; Scopulariopsis; Arthrographis spp.; Scytalidium; Scedosporium spp., e.g. Scedosporium apiospermum, Scedosporium prolificans; Trichoderma spp.; Penicillium spp.; Penicillium marneffei; Blastoschizomyces.

The compounds of Formula (I) and stereoisomeric forms thereof, and the pharmaceutically acceptable addition salts, and the solvates thereof, may be active against a wide variety of fungi, such as Candida parapsilosis; Aspergillus spp., e.g. Aspergillus fumigatus, Aspergillus niger, Aspergillus flavus; Cryptococcus neoformans; Sporothrix schenckii; Epidermophyton floccosum; Microsporum spp., e.g. Microsporum canis, Microsporum gypseum; Trichophyton spp., e.g. Trichophyton mentagrophytes, Trichophyton rubrum, Trichophyton quinckeanum, Trichophyton tonsurans, Trichophyton verrucosum, Trichophyton violaceum, Trichophyton interdigitale, Trichophyton soudanense; Fusarium spp., e.g. Fusarium solani, Fusarium oxysporum, Fusarium proliferatum, Fusarium verticillioides; Rhizomucor spp., e.g. Rhizomucor miehei, Rhizomucor pusillus; Mucor circinelloides; Rhizopus spp., e.g. Rhizopus oryzae, Rhizopus microspores; Acremonium spp.; Paecilomyces; Scopulariopsis; Arthrographis spp.; Scytalidium; Scedosporium spp., e.g. Scedosporium apiospermum, Scedosporium prolificans; Trichoderma spp.; Penicillium spp.; Penicillium marneffei; Blastoschizomyces.

The compounds of Formula (I) and stereoisomeric forms thereof, and the pharmaceutically acceptable addition salts, and the solvates thereof, may be active against a wide variety of fungi, such as Candida parapsilosis; Aspergillus spp., e.g. Aspergillus fumigatus, Aspergillus niger, Aspergillus flavus; Cryptococcus neoformans; Epidermophyton floccosum; Microsporum spp., e.g. Microsporum canis, Microsporum gypseum; Trichophyton spp., e.g. Trichophyton mentagrophytes, Trichophyton rubrum, Trichophyton quinckeanum, Trichophyton tonsurans, Trichophyton verrucosum, Trichophyton violaceum, Trichophyton interdigitale, Trichophyton soudanense; Fusarium spp., e.g. Fusarium solani, Fusarium oxysporum, Fusarium proliferatum, Fusarium verticillioides; Rhizomucor spp., e.g. Rhizomucor miehei, Rhizomucor pusillus; Mucor circinelloides; Rhizopus spp., e.g. Rhizopus oryzae, Rhizopus microspores; Acremonium spp.; Paecilomyces; Scopulariopsis; Arthrographis spp.; Scytalidium; Scedosporium spp., e.g. Scedosporium apiospermum, Scedosporium prolificans; Trichoderma spp.; Penicillium spp.; Penicillium marneffei; Blastoschizomyces; in particular Aspergillus spp., e.g. Aspergillus fumigatus, Aspergillus niger, Aspergillus flavus; Cryptococcus neoformans; Epidermophyton floccosum; Microsporum spp., e.g. Microsporum canis, Microsporum gypseum; Trichophyton spp., e.g. Trichophyton mentagrophytes, Trichophyton rubrum, Trichophyton quinckeanum, Trichophyton tonsurans, Trichophyton verrucosum, Trichophyton violaceum, Trichophyton interdigitale, Trichophyton soudanense; Fusarium spp., e.g. Fusarium solani, Fusarium oxysporum, Fusarium proliferatum, Fusarium verticillioides; Rhizomucor spp., e.g. Rhizomucor miehei, Rhizomucor pusillus; Mucor circinelloides; Rhizopus spp., e.g. Rhizopus oryzae, Rhizopus microspores; Acremonium spp.; Paecilomyces; Scopulariopsis; Arthrographis spp.; Scytalidium; Scedosporium spp., e.g. Scedosporium apiospermum, Scedosporium prolificans; Trichoderma spp.; Penicillium spp.; Penicillium marneffei; Blastoschizomyces. The compounds of Formula (I) and stereoisomeric forms thereof, and the pharmaceutically acceptable addition salts, and the solvates thereof, may be active against a wide variety of fungi, such as Candida parapsilosis; Aspergillus spp.; Cryptococcus neoformans; Sporothrix schenckii; Microsporum spp.; Fusarium spp.; Scedosporium spp.;

in particular Candida parapsilosis; Aspergillus spp.; Cryptococcus neoformans; Microsporum spp.; Fusarium spp.; Scedosporium spp.;

more in particular Aspergillus spp.; Cryptococcus neoformans; Microsporum spp.; Fusarium spp.; Scedosporium spp.

The compounds of Formula (I) and stereoisomeric forms thereof, and the pharmaceutically acceptable addition salts, and the solvates thereof, may be active against a wide variety of fungi, such as Candida parapsilosis; Aspergillus spp.; Cryptococcus neoformans; Trichophyton spp.; Sporothrix schenckii; Microsporum spp.; Fusarium spp.; Scedosporium spp.;

in particular Aspergillus spp.; Microsporum spp.; Trichophyton spp.

The compounds of Formula (I) and stereoisomeric forms thereof, and the pharmaceutically acceptable addition salts, and the solvates thereof, may be active against fungi such as Candida parapsilosis, Aspergillus spp., Cryptococcus neoformans, Microsporum spp., and Trichophyton spp.

The compounds of Formula (I) and stereoisomeric forms thereof, and the pharmaceutically acceptable addition salts, and the solvates thereof, may be active against fungi such as Candida parapsilosis; Aspergillus spp., e.g. Aspergillus fumigatus, Aspergillus niger, Aspergillus flavus; Cryptococcus neoformans; Sporothrix schenckii; Epidermophyton floccosum; Microsporum canis; Trichophyton spp., e.g. Trichophyton mentagrophytes, Trichophyton rubrum, Trichophyton quinckeanum; in particular Candida parapsilosis; Aspergillus spp., e.g. Aspergillus fumigatus, Aspergillus niger, Aspergillus flavus; Cryptococcus neoformans; Epidermophyton floccosum; Microsporum canis; Trichophyton spp., e.g. Trichophyton mentagrophytes, Trichophyton rubrum, Trichophyton quinckeanum;

more in particular Aspergillus spp., e.g. Aspergillus fumigatus, Aspergillus niger, Aspergillus flavus; Cryptococcus neoformans; Epidermophyton floccosum; Microsporum canis; Trichophyton spp., e.g. Trichophyton mentagrophytes, Trichophyton rubrum, Trichophyton quinckeanum.

The compounds of Formula (I) and stereoisomeric forms thereof, and the pharmaceutically acceptable addition salts, and the solvates thereof, may be active against Candida parapsilosis, Aspergillus fumigatus, Cryptococcus neoformans, Sporothrix schenckii, Microsporum canis, Trichophyton mentagrophytes, Trichophyton rubrum, Scedosporium apiospermum and Scedosporium prolificans; in particular Aspergillus fumigatus, Microsporum canis, Trichophyton mentagrophytes, Trichophyton rubrum, Scedosporium apiospermum and Scedosporium prolificans.

The compounds of Formula (I) and stereoisomeric forms thereof, and the pharmaceutically acceptable addition salts, and the solvates thereof, may be active against fungi such as Candida parapsilosis; Aspergillus spp.; Cryptococcus neoformans; Microsporum spp.; Trichophyton spp.; Scedosporium spp.

The compounds of Formula (I) and stereoisomeric forms thereof, and the pharmaceutically acceptable addition salts, and the solvates thereof, may be active against Candida parapsilosis, Aspergillus fumigatus, Cryptococcus neoformans, Sporothrix schenckii, Microsporum canis, Trichophyton mentagrophytes, Trichophyton rubrum, Scedosporium apiospermum, Scedosporium prolificans;

in particular Candida parapsilosis, Aspergillus fumigatus, Cryptococcus neoformans, Microsporum canis, Trichophyton mentagrophytes, Trichophyton rubrum, Scedosporium apiospermum, Scedosporium prolificans;
more in particular Aspergillus fumigatus, Cryptococcus neoformans, Microsporum canis, Trichophyton mentagrophytes, Trichophyton rubrum, Scedosporium apiospermum, Scedosporium prolificans.

The compounds of Formula (I) and stereoisomeric forms thereof, and the pharmaceutically acceptable addition salts, and the solvates thereof, may be active against Candida parapsilosis, Aspergillus fumigatus, Cryptococcus neoformans, Sporothrix schenckii, Microsporum canis, Trichophyton mentagrophytes, Trichophyton rubrum, Scedosporium apiospermum, Scedosporium prolificans, Rhizopus oryzae, Rhizomucor miehei.

The compounds of Formula (I) and stereoisomeric forms thereof, and the pharmaceutically acceptable addition salts, and the solvates thereof, may be active against Candida parapsilosis B66126, Aspergillus fumigatus B42928, Cryptococcus neoformans B66663, Sporothrix schenckii B62482, Microsporum canis B68128, Trichophyton mentagrophytes B70554, Trichophyton rubrum B68183, Scedosporium apiospermum IHEM3817, Scedosporium prolificans IHEM21157.

The compounds of Formula (I) and stereoisomeric forms thereof, and the pharmaceutically acceptable addition salts, and the solvates thereof, may be active against Candida parapsilosis B66126, Aspergillus fumigatus B42928, Cryptococcus neoformans B66663, Sporothrix schenckii B62482, Microsporum canis B68128, Trichophyton mentagrophytes B70554, Trichophyton rubrum B68183, Scedosporium apiospermum IHEM3817, Scedosporium prolificans IHEM21157, Rhizopus oryzae IHEM5223 and Rhizomucor miehei IHEM13391.

The compounds of Formula (I) and stereoisomeric forms thereof, and the pharmaceutically acceptable addition salts, and the solvates thereof, may be active against Candida parapsilosis, Aspergillus fumigatus, Cryptococcus neoformans, Microsporum canis, Trichophyton mentagrophytes, Trichophyton rubrum; in particular Aspergillus fumigatus, Cryptococcus neoformans, Microsporum canis, Trichophyton mentagrophytes, Trichophyton rubrum.

The compounds of Formula (I) and stereoisomeric forms thereof, and the pharmaceutically acceptable addition salts, and the solvates thereof, may be active against Microsporum canis, Trichophyton rubrum, Aspergillus fumigatus, Cryptococcus neoformans and Trichophyton mentagrophytes;
in particular Microsporum canis B68128, Trichophyton rubrum B68183, Aspergillus fumigatus B42928, Cryptococcus neoformans B66663 and Trichophyton mentagrophytes B70554.

The compounds of Formula (I) and stereoisomeric forms thereof, and the pharmaceutically acceptable addition salts, and the solvates thereof, may be active against Candida parapsilosis B66126, Aspergillus fumigatus B42928, Cryptococcus neoformans B66663, Microsporum canis B68128, Trichophyton mentagrophytes B70554, Trichophyton rubrum B68183, Rhizopus oryzae IHEM5223, Rhizomucor miehei IHEM13391.

The compounds of Formula (I) and stereoisomeric forms thereof, and the pharmaceutically acceptable addition salts, and the solvates thereof, may be active against Candida parapsilosis B66126, Aspergillus fumigatus B42928, Cryptococcus neoformans B66663, Microsporum canis B68128, Trichophyton mentagrophytes B70554, Trichophyton rubrum B68183; in particular Aspergillus fumigatus B42928, Cryptococcus neoformans B66663, Microsporum canis B68128, Trichophyton mentagrophytes B70554, Trichophyton rubrum B68183.

The compounds of Formula (I) and stereoisomeric forms thereof, and the pharmaceutically acceptable addition salts, and the solvates thereof, may be active against a variety of fungi that infect the skin, hair and nails, as well as subcutaneous and systemic fungal pathogens.

The compounds of Formula (I) and stereoisomeric forms thereof, and the pharmaceutically acceptable addition salts, and the solvates thereof, may be active against a wide variety of fungi, such as Aspergillus spp.; Microsporum spp.; Trichophyton spp.; Scedosporium spp.; Candida parapsilosis; and Cryptococcus neoformans; in particular Aspergillus spp.; Microsporum spp.; and Trichophyton spp.

The compounds of Formula (I) and stereoisomeric forms thereof, and the pharmaceutically acceptable addition salts, and the solvates thereof, may be active against a wide variety of fungi, such as Aspergillus spp.; Microsporum spp.; Trichophyton spp.; Scedosporium spp.; in particular Trichophyton spp. and Microsporum spp.

The compounds of Formula (I) and stereoisomeric forms thereof, and the pharmaceutically acceptable addition salts, and the solvates thereof, may be active against a wide variety of fungi, such as Aspergillus fumigatus, Microsporum canis, Trichophyton mentagrophytes, Trichophyton rubrum, Scedosporium apiospermum and Scedosporium prolificans; in particular Microsporum canis, Trichophyton mentagrophytes and Trichophyton rubrum.

The compounds of Formula (I) and stereoisomeric forms thereof, and the pharmaceutically acceptable addition salts, and the solvates thereof, may be active against the 3 dermatophyte genera: Trichophyton, Microsporum and Epidermophyton; in particular against Trichophyton and Microsporum.

The compounds of Formula (I) and stereoisomeric forms thereof, and the pharmaceutically acceptable addition salts, and the solvates thereof, may be active against dermatophytes and Aspergillus spp.; in particular dermatophytes and Aspergillus fumigatus; more in particular Microsporum canis, Trichophyton mentagrophytes, Trichophyton rubrum and Aspergillus fumigatus; even more in particular Microsporum canis, Trichophyton mentagrophytes and Trichophyton rubrum.

The compounds of Formula (I) and stereoisomeric forms thereof, and the pharmaceutically acceptable addition salts, and the solvates thereof, may be active against Trichophyton mentagrophytes, Trichophyton rubrum and Aspergillus spp.; in particular Trichophyton mentagrophytes, Trichophyton rubrum and Aspergillus fumigatus.

The compounds of Formula (I) and stereoisomeric forms thereof, and the pharmaceutically acceptable addition salts, and the solvates thereof, may be active against Trichophyton mentagrophytes; Trichophyton rubrum; Aspergillus spp., e.g. Aspergillus fumigatus; Fusarium spp.; Mucor Spp.; Zygomycetes spp.; Scedosporium spp.; Microsporum canis; Sporothrix schenckii; Cryptococcus neoformans; Candida parapsilosis.

The compounds of Formula (I) and stereoisomeric forms thereof, and the pharmaceutically acceptable addition salts, and the solvates thereof, may be active against dermatophytes.

The compounds of Formula (I) and stereoisomeric forms thereof, and the pharmaceutically acceptable addition salts, and the solvates thereof, may be active against Aspergillus fumigatus.

The compounds of Formula (I) and stereoisomeric forms thereof, and the pharmaceutically acceptable addition salts, and the solvates thereof, may be active against *Microsporum canis*, in particular *Microsporum canis* B68128.

The compounds of Formula (I) and stereoisomeric forms thereof, and the pharmaceutically acceptable addition salts, and the solvates thereof, may be active against *Trichophyton rubrum*, in particular *Trichophyton rubrum* B68183.

The compounds of Formula (I) and stereoisomeric forms thereof, and the pharmaceutically acceptable addition salts, and the solvates thereof, are potent antifungals when administered orally or topically.

The compounds of the present invention may be useful as ergosterol synthesis inhibitors.

In view of the utility of the compound of Formula (I), there is provided a method of treating warm-blooded animals, including humans, suffering from, or a method of preventing warm-blooded animals, including humans, to suffer from any one of the diseases mentioned hereinbefore. Hence, compounds of Formula (I) are provided for use as a medicine. Also the use of a compound of Formula (I) in the manufacture of a medicament useful in treating fungal infections is provided. Further compounds of Formula (I) are provided for use in the treatment of fungal infections As used herein, the term "treatment" is intended to refer to all processes, wherein there may be a slowing, interrupting, arresting, or stopping of the progression of an infection, but does not necessarily indicate a total elimination of all symptoms.

The invention relates to a compound according to the general Formula (I), the stereoisomeric forms thereof and the pharmaceutically acceptable acid or base addition salts and the solvates thereof, for use as a medicament.

The invention also relates to a compound according to the general Formula (I), the stereoisomeric forms thereof and the pharmaceutically acceptable acid or base addition salts and the solvates thereof, for the treatment or prevention of fungal infections; in particular fungal infections caused by one or more of the fungi mentioned hereinbefore.

The invention also relates to a compound according to the general Formula (I), the stereoisomeric forms thereof and the pharmaceutically acceptable acid or base addition salts and the solvates thereof, for the treatment of fungal infections; in particular fungal infections caused by one or more of the fungi mentioned hereinbefore.

The invention also relates to a compound according to the general Formula (I), the stereoisomeric forms thereof and the pharmaceutically acceptable acid or base addition salts and the solvates thereof, for use in the treatment or prevention of fungal infections; in particular fungal infections caused by one or more of the fungi mentioned hereinbefore.

The invention also relates to a compound according to the general Formula (I), the stereoisomeric forms thereof and the pharmaceutically acceptable acid or base addition salts and the solvates thereof, for use in the treatment of fungal infections; in particular fungal infections caused by one or more of the fungi mentioned hereinbefore.

The invention also relates to compounds according to the general Formula (I), the stereoisomeric forms thereof and the pharmaceutically acceptable acid or base addition salts and the solvates thereof, for use in the treatment or prevention, in particular treatment, of fungal infections; in particular fungal infections caused by one or more of the fungi selected from a group consisting of fungi mentioned hereinbefore.

The invention also relates to compounds according to the general Formula (I), the stereoisomeric forms thereof and the pharmaceutically acceptable acid or base addition salts and the solvates thereof, for use in the treatment or prevention of a fungal infection, in particular a fungal infection caused by one or more of the fungi mentioned hereinbefore.

The invention also relates to compounds according to the general Formula (I), the stereoisomeric forms thereof and the pharmaceutically acceptable acid or base addition salts and the solvates thereof, for use in the treatment or prevention of a fungal infection, wherein the fungal infection is caused by one or more of the fungi selected from the group consisting of *Candida* spp.; *Aspergillus* spp.; *Cryptococcus neoformans*; *Sporothrix schenckii*; *Epidermophyton floccosum*; *Microsporum* spp.; *Trichophyton* spp; *Fusarium* spp.; *Rhizomucor* spp.; *Mucor circinelloides*; *Rhizopus* spp.; *Malassezia furfur*; *Acremonium* spp.; *Paecilomyces*; *Scopulariopsis*; *Arthrographis* spp.; *Scytalidium*; *Scedosporium* spp.; *Trichoderma* spp.; *Penicillium* spp.; *Penicillium marneffei*; and *Blastoschizomyces*;

in particular wherein the fungal infection is caused by one or more of the fungi selected from the group consisting of *Candida parapsilosis*; *Aspergillus* spp.; *Cryptococcus neoformans*; *Sporothrix schenckii*; *Epidermophyton floccosum*; *Microsporum* spp.; *Trichophyton* spp.; *Fusarium* spp.; *Rhizomucor* spp.; *Mucor circinelloides*; *Rhizopus* spp.; *Acremonium* spp.; *Paecilomyces*; *Scopulariopsis*; *Arthrographis* spp.; *Scytalidium*; *Scedosporium* spp.; *Trichoderma* spp.; *Penicillium* spp.; *Penicillium marneffei*; and *Blastoschizomyces*;

even more in particular wherein the fungal infection is caused by one or more of the fungi selected from the group consisting of *Microsporum canis, Trichophyton mentagrophytes, Trichophyton rubrum* and *Aspergillus fumigatus*.

The invention also relates to a compound according to the general Formula (I), the stereoisomeric forms thereof and the pharmaceutically acceptable acid or base addition salts and the solvates thereof, for use in the treatment or prevention of a fungal infection, wherein the fungal infection is caused by one or more of the fungi selected from the group consisting of *Candida* spp.; *Aspergillus* spp.; *Cryptococcus neoformans*; *Sporothrix schenckii*; *Epidermophyton floccosum*; *Microsporum* spp.; *Trichophyton* spp; *Fusarium* spp.; *Rhizomucor* spp.; *Mucor circinelloides*; *Rhizopus* spp.; *Malassezia furfur*; *Acremonium* spp.; *Paecilomyces*; *Scopulariopsis*; *Arthrographis* spp.; *Scytalidium*; *Scedosporium* spp.; *Trichoderma* spp.; *Penicillium* spp.; *Penicillium marneffei*; *Blastoschizomyces*; in particular wherein the fungal infection is caused by one or more of the fungi selected from the group consisting of *Aspergillus* spp.; *Microsporum* spp.; *Trichophyton* spp.; and *Scedosporium* spp.;

more in particular wherein the fungal infection is caused by one or more of the fungi selected from the group consisting of *Microsporum canis, Trichophyton mentagrophytes* and *Trichophyton rubrum*.

The compounds of Formula (I) and stereoisomeric forms thereof, and the pharmaceutically acceptable addition salts, and the solvates thereof, may be active against a wide variety of fungi, such as one or more of the fungi mentioned hereinbefore.

The novel compounds described in the present invention may be useful in the treatment or prevention of diseases or conditions selected from the group consisting of infections caused by dermatophytes, systemic fungal infections and onychomycosis.

The novel compounds described in the present invention may be useful in the treatment or prevention of diseases or conditions such as for example infections caused by dermatophytes, systemic fungal infections or onychomycosis.

The invention also relates to the use of a compound according to the general Formula (I), the stereoisomeric forms thereof and the pharmaceutically acceptable acid or base addition salts and the solvates thereof, for the manufacture of a medicament.

The invention also relates to the use of a compound according to the general Formula (I), the stereoisomeric forms thereof and the pharmaceutically acceptable acid or base addition salts and the solvates thereof, for the manufacture of a medicament for the treatment or prevention, in particular treatment, of fungal infections, in particular fungal infections caused by one or more of the fungi mentioned hereinbefore.

The compounds of the present invention can be administered to mammals, preferably humans, for the treatment or prevention, in particular treatment, of fungal infections, in particular fungal infections caused by one or more of the fungi mentioned hereinbefore.

In view of the utility of the compound of Formula (I), there is provided a method of treating warm-blooded animals, including humans, suffering from or a method of preventing warm-blooded animals, including humans, to suffer from fungal infections, in particular fungal infections caused by one or more of the fungi mentioned hereinbefore.

Said methods comprise the administration, i.e. the systemic or topical administration, preferably oral administration, of an effective amount of a compound of Formula (I), a stereoisomeric form thereof or a pharmaceutically acceptable addition salt or solvate thereof, to warm-blooded animals, including humans.

Said methods comprise the administration, i.e. the systemic or topical administration, preferably oral administration, of an effective amount of a compound of Formula (I), to warm-blooded animals, including humans.

Those of skill in the treatment of such diseases could determine the effective therapeutic daily amount from the test results presented hereinafter. An effective therapeutic daily amount would be from about 0.005 mg/kg to 50 mg/kg, in particular 0.01 mg/kg to 50 mg/kg body weight, more in particular from 0.01 mg/kg to 25 mg/kg body weight, preferably from about 0.01 mg/kg to about 15 mg/kg, more preferably from about 0.01 mg/kg to about 10 mg/kg, even more preferably from about 0.01 mg/kg to about 1 mg/kg, most preferably from about 0.05 mg/kg to about 1 mg/kg body weight. The amount of a compound according to the present invention, also referred to here as the active ingredient, which is required to achieve a therapeutically effect will of course, vary on case-by-case basis, for example with the particular compound, the route of administration, the age and condition of the recipient, and the particular disorder or disease being treated.

A method of treatment may also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

While it is possible for the active ingredient to be administered alone, it is preferable to present it as a pharmaceutical composition.

The present invention also provides compositions for treating or preventing fungal infections comprising a therapeutically effective amount of a compound of Formula (I) and a pharmaceutically acceptable carrier or diluent.

The carrier or diluent must be "acceptable" in the sense of being compatible with the other ingredients of the composition and not deleterious to the recipients thereof.

The compounds of the present invention, that are suitable to treat or prevent fungal infections, may be administered alone or in combination with one or more additional therapeutic agents. Combination therapy includes administration of a single pharmaceutical dosage formulation which contains a compound of Formula (I) and one or more additional therapeutic agents, as well as administration of the compound of Formula (I) and each additional therapeutic agents in its own separate pharmaceutical dosage formulation. For example, a compound of Formula (I) and a therapeutic agent may be administered to the patient together in a single oral dosage composition such as a tablet or capsule, or each agent may be administered in separate oral dosage formulations.

In view of their useful pharmacological properties, the subject compounds may be formulated into various pharmaceutical forms for administration purposes. The compounds according to the invention, in particular the compounds according to Formula (I), a pharmaceutically acceptable acid or base addition salt thereof, a stereochemically isomeric form thereof, or any subgroup or combination thereof may be formulated into various pharmaceutical forms for administration purposes. As appropriate compositions there may be cited all compositions usually employed for systemically administering drugs.

To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions, for example, may be prepared in which the carrier comprises saline solution, glucose solution or a mixture of saline and glucose solution. Injectable solutions containing compounds of Formula (I) may be formulated in an oil for prolonged action. Appropriate oils for this purpose are, for example, peanut oil, sesame oil, cottonseed oil, corn oil, soybean oil, synthetic glycerol esters of long chain fatty acids and mixtures of these and other oils. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. Acid or base addition salts of compounds of Formula (I) due to their increased water solubility over the corresponding base or acid form, are more suitable in the preparation of aqueous compositions.

Transungual compositions are in the form of a solution and the carrier optionally comprises a penetration enhancing agent which favours the penetration of the antifungal into and through the keratinized ungual layer of the nail. The solvent medium comprises water mixed with a co-solvent such as an alcohol having from 2 to 6 carbon atoms, e.g. ethanol.

In order to enhance the solubility and/or the stability of the compounds of Formula (I) in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the invention in pharmaceutical compositions.

The ratio of active ingredient over cyclodextrin may vary widely. For example ratios of 1/100 to 100/1 may be applied. Interesting ratios of active ingredient over cyclodextrin range from about 1/10 to 10/1. More interesting ratios of active ingredient over cyclodextrin range from about 1/5 to 5/1.

Depending on the mode of administration, the pharmaceutical composition will preferably comprise from 0.05 to 99% by weight, more preferably from 0.1 to 70% by weight, even more preferably from 0.1 to 50% by weight of the compound of Formula (I), and, from 1 to 99.95% by weight, more preferably from 30 to 99.9% by weight, even more preferably from 50 to 99.9% by weight of a pharmaceutically acceptable carrier, all percentages being based on the total weight of the composition.

For parenteral compositions, also other ingredients, to aid solubility for example, e.g. cyclodextrins, may be included. Appropriate cyclodextrins are α-, β-, γ-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated β-CD; hydroxy$C_{1-6}$alkyl, particularly hydroxyethyl, hydroxy-propyl or hydroxybutyl; carboxy$C_{1-6}$alkyl, particularly carboxymethyl or carboxy-ethyl; $C_{1-6}$alkylcarbonyl, particularly acetyl. Especially noteworthy as complexants and/or solubilizers are β-CD, randomly methylated β-CD, 2,6-dimethyl-β-CD, 2-hydroxyethyl-β-CD, 2-hydroxyethyl-γ-CD, 2-hydroxypropyl-γ-CD and (2-carboxymethoxy)propyl-β-CD, and in particular 2-hydroxypropyl-β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

The average molar substitution (M.S.) is used as a measure of the average number of moles of alkoxy units per mole of anhydroglucose. The average substitution degree (D.S.) refers to the average number of substituted hydroxyls per anhydroglucose unit. The M.S. and D.S. value can be determined by various analytical techniques such as nuclear magnetic resonance (NMR), mass spectrometry (MS) and infrared spectroscopy (IR). Depending on the technique used, slightly different values may be obtained for one given cyclodextrin derivative. Preferably, as measured by mass spectrometry, the M.S. ranges from 0.125 to 10 and the D.S. ranges from 0.125 to 3.

Other suitable compositions for oral or rectal administration comprise particles consisting of a solid dispersion comprising a compound of Formula (I) and one or more appropriate pharmaceutically acceptable water-soluble polymers.

The term "a solid dispersion" defines a system in a solid state (as opposed to a liquid or gaseous state) comprising at least two components, in casu the compound of Formula (I) and the water-soluble polymer, wherein one component is dispersed more or less evenly throughout the other component or components (in case additional pharmaceutically acceptable formulating agents, generally known in the art, are included, such as plasticizers, preservatives and the like). When said dispersion of the components is such that the system is chemically and physically uniform or homogenous throughout or consists of one phase as defined in thermodynamics, such a solid dispersion will be called "a solid solution". Solid solutions are preferred physical systems because the components therein are usually readily bioavailable to the organisms to which they are administered. This advantage can probably be explained by the ease with which said solid solutions can form liquid solutions when contacted with a liquid medium such as the gastro-intestinal juices. The ease of dissolution may be attributed at least in part to the fact that the energy required for dissolution of the components from a solid solution is less than that required for the dissolution of components from a crystalline or microcrystalline solid phase.

The term "a solid dispersion" also comprises dispersions which are less homogenous throughout than solid solutions. Such dispersions are not chemically and physically uniform throughout or comprise more than one phase. For example, the term "a solid dispersion" also relates to a system having domains or small regions wherein amorphous, microcrystalline or crystalline compound of Formula (I), or amorphous, microcrystalline or crystalline water-soluble polymer, or both, are dispersed more or less evenly in another phase comprising water-soluble polymer, or compound of Formula (I), or a solid solution comprising compound of Formula (I) and water-soluble polymer. Said domains are regions within the solid dispersion distinctively marked by some physical feature, small in size, and evenly and randomly distributed throughout the solid dispersion.

It may further be convenient to formulate the present antifungal compounds in the form of nanoparticles which have a surface modifier adsorbed on the surface thereof in an amount sufficient to maintain an effective average particle size of less than 1000 nm. Useful surface modifiers are believed to include those which physically adhere to the surface of the antifungal agent but do not chemically bond to the antifungal agent.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the present compounds involves a pharmaceutical composition whereby the present antifungals are incorporated in hydrophilic polymers and applying this mixture as a coat film over many small beads, thus yielding a composition which can conveniently be manufactured and which is suitable for preparing pharmaceutical dosage forms for oral administration.

Said beads comprise a central, rounded or spherical core, a coating film of a hydrophilic polymer and an antifungal agent and a seal-coating layer.

Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

It is especially advantageous to formulate the aforementioned pharmaceutical compositions in unit dosage form for ease of administration and uniformity of dosage.

Unit dosage form as used in the specification and claims herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions, teaspoonfuls, tablespoonfuls and the like, and segregated multiples thereof.

Since the compounds according to the invention are potent orally administrable compounds, pharmaceutical compositions comprising said compounds for administration orally are especially advantageous.

The following examples illustrate the present invention.

EXPERIMENTAL PART

Hereinafter, the term "DCM" means dichloromethane; "LCMS" means Liquid Chromatography/Mass spectrometry; "Et$_3$N" means triethylamine; "PE" means petroleum ether; "TFA" means trifluoroacetic acid; "HPLC" means high-performance liquid chromatography; "r.t." means room temperature; "m.p." means melting point; "min" means minute(s); "h" means hour(s); "EtOAc" means ethyl acetate; "EtOH" means ethanol; "MeOH" means methanol; "r.m." means reaction mixture(s); "q.s." quantum sufficit; "THF" means tetrahydrofuran; "HOAc" means acetic acid; "HBTU" means 1-[bis(dimethylamino)methylene]-1H-benzotriazol-1-ium 3-oxide hexafluoro-phosphate, "HOBT" means 1-hydroxy-1H-benzotriazole; "Me$_2$S" means dimethyl sulfide; and "EDCI" means N'-(ethylcarbonimidoyl)-N,N-dimethyl-1,3-propanediamine monohydrochloride.

The person skilled in the art will realize that for some reactions in the examples anhydrous conditions need to be applied and/or an inert protecting atmosphere such as, for example, N$_2$ or argon, must be used.

A. Preparation of the Intermediates

Example A1 a) Preparation of Intermediate 1

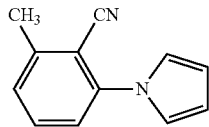

A solution of 2-amino-6-methylbenzonitrile (25.0 g, 0.189 mol) and tetrahydro-2,5-dimethoxyfuran (25.0 g, 0.189 mol) in HOAc (200 ml) was refluxed for 4 h. After reaction, the solvent was evaporated and the product was dried in vacuo and directly used as such in the next reaction step. Yield: 33.0 g of intermediate 1.

b) Preparation of Intermediate 2

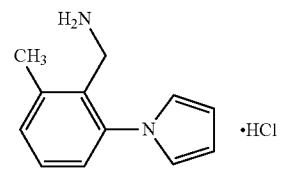

A solution of intermediate 1 (33.0 g, approximately 0.181 mol) and borane-dimethyl sulphide (1:1) (20 ml of a 10 N solution of BH$_3$ in Me$_2$S, 0.20 mol) in THF (100 ml) was refluxed for 16 h. Subsequently, HCl (6 N; 50 ml) was added at 0° C. The mixture was heated under reflux again for 30 min. The solution was cooled to 0° C. (ice-water bath) and NaOH (solid; q.s.) was added until pH>10. The mixture was extracted with DCM (3×) and the separated organic layer was dried (MgSO$_4$), filtered, and the solvent was evaporated. The residue was treated with HCl/dioxane (q.s.) to obtain 27 g of intermediate 2 (67.5% yield; .HCl).

Example A2 a) Preparation of Intermediate 3

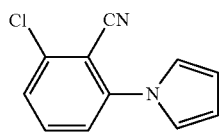 [SMILES: N#Cc1c(Cl)cccc1-n1cccc1]

A mixture of 2-amino-6-chlorobenzonitrile (17.72 g, 0.116 mol) and tetrahydro-2,5-dimethoxyfuran (0.116 mol) in HOAc (100 ml) was stirred and refluxed for 30 min. Subsequently, the mixture was cooled and evaporated. The residue was purified over silica gel on a glass filter (eluent: DCM). The product fractions were collected and the solvent was evaporated. The residue was crystallized from EtOH. Yield: 18.83 g of intermediate 3 (80% yield).

b) Preparation of Intermediate 4

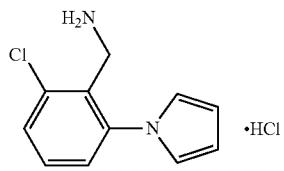 [SMILES: NCc1c(Cl)cccc1-n1cccc1 ; Cl]

Borane-dimethyl sulphide (1:1) (2.5 ml of a 10 N solution of BH$_3$ in Me$_2$S, 0.0247 mol) was added at r.t. under N$_2$ atmosphere to a solution of intermediate 3 (5.0 g, 0.0247 mol) in THF (20 ml). The mixture was heated to reflux for 10 h. After cooling to r.t., HCl (6 N; 15 ml) was added dropwise. Subsequently the mixture was heated under reflux for 30 min. The solution was cooled to 0° C. and then NaOH (6 N; q.s.) was added. The mixture was extracted with DCM (50 ml×3) and the separated organic layer was dried (Na$_2$SO$_4$), filtered, and the solvent was evaporated to yield an oil. HCl/dioxane (5 ml) and THF (20 ml) were added and the precipitate was collected by filtration and dried. Yield: 5.14 g of intermediate 4 (86% yield; .HCl).

Intermediate 6

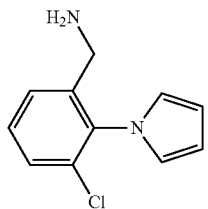 [SMILES: NCc1cccc(Cl)c1-n1cccc1]

.HCl was prepared by an analogous protocol as described for the synthesis of intermediate 4.

c) Preparation of Intermediate 5

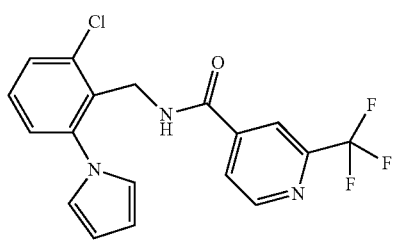 [SMILES: O=C(NCc1c(Cl)cccc1-n1cccc1)c1ccnc(C(F)(F)F)c1]

2-(Trifluoromethyl)-4-pyridinecarboxylic acid (0.28 g, 1.45 mmol) was dissolved in DCM (20 ml). Et$_3$N (1.5 ml, 9.2 mmol), HOBT (0.20 g, 1.45 mmol), EDCI (0.28 g, 1.45 mmol) and intermediate 4 (0.32 g, 1.32 mmol) were added to the solution. The r.m. was stirred overnight at r.t. Water (q.s.) was added and the mixture was extracted with DCM. The separated organic layer was dried (Na$_2$SO$_4$), filtered and the solvent was evaporated. The crude product was purified by preparative HPLC (Synergy column 150×30 mm; mobile phase: 55%-85% CH$_3$CN (0.1% TFA)/H$_2$O (0.1% TFA); flow rate 25 ml/min; 19 min). The product fractions were collected and the solvent was evaporated in vacuo. The residue was neutralized with a saturated NaHCO$_3$ solution and extracted with DCM. The organic layer was dried (Na$_2$SO$_4$), filtered and the solvent was evaporated, yielding intermediate 5 (38% yield).

Example A3

Preparation of Intermediate 7

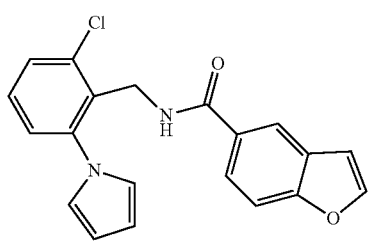 [SMILES: O=C(NCc1c(Cl)cccc1-n1cccc1)c1ccc2occc2c1]

5-Benzofurancarboxylic acid (0.285 g, 1.76 mmol) was dissolved in DCM (20 ml). Et$_3$N (1.3 ml, 8.8 mmol), HOBT (0.237 g, 1.76 mmol), EDCI (0.337 g, 1.76 mmol) and intermediate 4 (0.427 g, 1.76 mmol) were added to the solution. The r.m. was stirred overnight at r.t. Subsequently, the mixture was concentrated and water (q.s.) was added. The aqueous mixture was extracted with DCM. The separated organic layer was dried (Na$_2$SO$_4$), filtered and the solvent was evaporated. The crude product was purified by HPLC (YMC column 150×25 mm; mobile phase: 52%-72% CH$_3$CN (0.1% TFA)/H$_2$O (0.1% TFA); flow rate 20 ml/min; 20 min). The product fractions were collected and the solvent was evaporated in vacuo. The residue was neutralized with a saturated NaHCO$_3$ solution and extracted with DCM. The organic layer was dried (Na$_2$SO$_4$), filtered and the solvent was evaporated, yielding 0.190 g of intermediate 7 (32% yield).

Example A4

Preparation of Intermediate 8

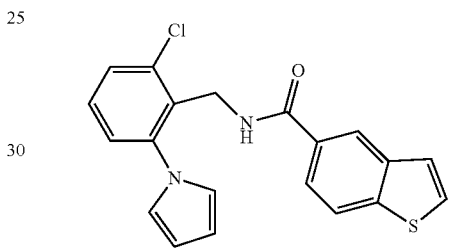

A mixture of 1-benzothiophene-5-carboxylic acid (1.01 g, 5.68 mmol), DCM (20 ml), Et$_3$N (3 ml), HOBT (0.76 g, 5.68 mmol), HBTU (2.12 g, 5.68 mmol) and intermediate 4 (1.26 g, 5.16 mmol) was stirred overnight at r.t. Subsequently, the mixture was washed with water (3×100 ml), dried (MgSO$_4$), filtered, and the solvent was evaporated under reduced pressure. The residue was purified by column chromatography over silica gel (eluent: PE/EtOAc from 10/1 to 5/1). The desired fractions were collected and the solvent was evaporated in vacuo. Yield: 1.5 g of intermediate 8 (79%).

Example A5 a) Preparation of Intermediate 9

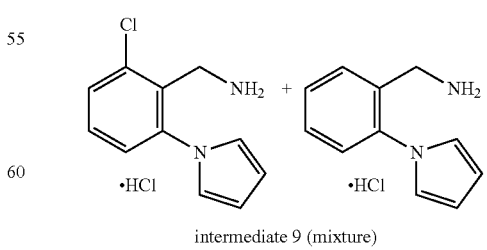

intermediate 9 (mixture)

LiAlH$_4$ (54.3 ml, 109 mmol) in anhydrous THF (20 ml) was added over a period of 2 minutes to a stirring solution of 2-chloro-6-(1H-pyrrol-1-yl)benzonitrile (20 g, 99 mmol)

in anhydrous THF (200 ml) while cooling the reaction mixture with ice. After addition, the r.m. was cooled with an ice-bath and was stirred for 1 hour. Subsequently, the reaction mixture was refluxed for 1 hour.

Then, water (100 ml) was added to 500 ml of a saturated solution of (2R,3R)-2,3-dihydroxybutanedioic acid monopotassium monosodium salt tetrahydrate (84 g, 296 mmol) (Rochelle salt). First the r.m. and then EtOAc (1 l) were added to this solution under vigorously stirring and ice cooling. The mixture was stirred for 2 hours while the mixture was allowed to reach room temperature.

The layers were separated and the aqueous layer was extracted with EtOAc (500 ml). The combined organic layers were washed with water (50 ml), dried ($Na_2SO_4$) and filtered. The filtrate was evaporated under reduced pressure to yield a yellow translucent oil. This oil was dissolved in $Et_2O$ (2 l) and HCl in dioxane (4 M, q.s.) was added to this solution. The suspension was filtered and washed with $Et_2O$, to yield 12.4 g of intermediate 9 (mixture 2 products).

b) Preparation of Intermediate 10

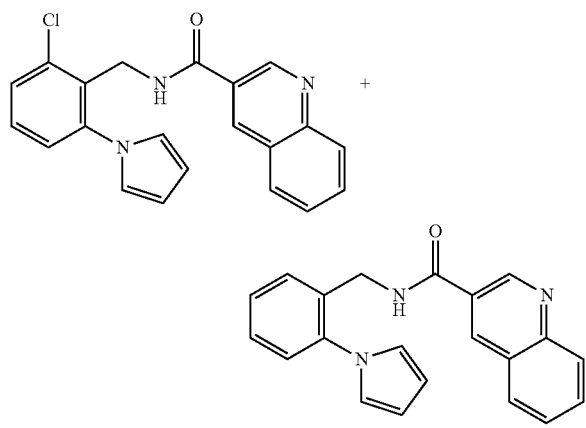

intermediate 10 (mixture)

O-(Benzo triazol-1-yl)-N,N,N',N'-tetramethyluronium tetrafluoroborate (TBTU) (1.709 g, 5.32 mmol) was added to a solution of 3-quinolinecarboxylic acid (0.838 g, 4.84 mmol) and N,N-di-iso-propylethylamine (DIPEA) (3.20 ml, 19.35 mol) in anhydrous DMF (20 ml). This mixture was stirred for 10 minutes. Subsequently, intermediate 9 (1 g) was added and the reaction mixture was left overnight at room temperature. The solvent was evaporated under reduced pressure (co-evaporated with xylene/toluene).

Water (100 ml) and EtOAc (100 ml) were added to the crude oil. Both layers were separated and the organic layer was washed twice with an aqueous solution of 1 N HCl (2×25 ml). The water layer was extracted with EtOAc (100 ml). The combined organic layers were washed with a saturated solution of $NaHCO_3$, dried ($Na_2SO_4$), filtered and evaporated under reduced pressure to yield a dark residue. The crude residue was purified using flash chromatography (100% hexane to 100% EtOAc) to yield 0.9 g of intermediate 10 as a beige solid (mixture of 2 products).

Example A6

Preparation of Intermediate 11

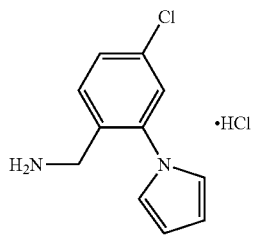 [SMILES: NCc1ccc(Cl)cc1-n1cccc1 ; Cl]

$LiAlH_4$ (125 ml, 250 mmol) in anhydrous THF (20 ml) was added over a period of 2 minutes to a stirring solution of 4-chloro-2-(1H-pyrrol-1-yl)benzonitrile (23 g, 114 mmol) in anhydrous THF (200 ml) while cooling the reaction mixture with ice. After addition, the r.m. was stirred for 1 hour at 0° C.

Ice water (100 ml) was added to 200 ml of a saturated solution of (2R,3R)-2,3-dihydroxybutanedioic acid monopotassium monosodium salt tetrahydrate (96 g, 341 mmol) (Rochelle salt). Subsequently, first the r.m. and then EtOAc (300 ml) were added to this solution under vigorously stirring and ice cooling. The mixture was stirred for 2 hours while the reaction mixture was allowed to reach room temperature.

The layers were separated and the aqueous layer was extracted with EtOAc (300 ml). The combined organic layers were washed with water (50 ml), dried ($Na_2SO_4$) and filtered. The filtrate was evaporated under reduced pressure to yield a yellow translucent oil. This oil was dissolved in $Et_2O$ (800 ml) and HCl in dioxane (q.s.) was added to this solution. The precipitating salts were filtered and washed with $Et_2O$. The filter residue was dried overnight in vacuo to yield 18 g of intermediate 11 as a yellow solid.

B. Preparation of the Compounds

Example B1 a) Preparation of Compound 1

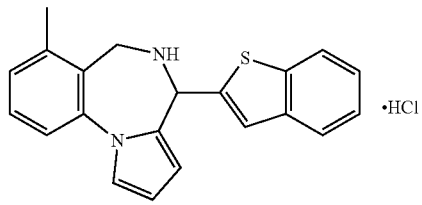 [SMILES: Cc1cccc2c1CNC(c1cc3ccccc3s1)c1cccn1-2 ; Cl]

A mixture of intermediate 2 (1.5 g, 0.0067 mol) and benzo[b]thiophene-2-carboxaldehyde (1.42 g, 0.0088 mol) in EtOH (15 ml) was stirred and refluxed for 4 h. The mixture was cooled off, and was then recrystallized overnight. The product was filtered off, and dried in vacuo. Yield: 1.45 g of compound 1 (59.2% yield; .HCl).

b) Preparation of Compound 2

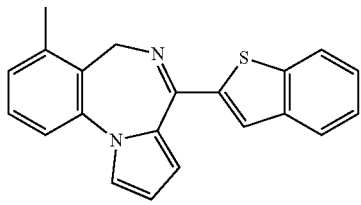 [SMILES: Cc1cccc2c1CN=C(c1cc3ccccc3s1)c1cccn1-2]

Compound 1 (1.4 g, 0.0038 mol) was treated with NH$_3$.H$_2$O (10 ml), and extracted with DCM (50 ml). The layers were separated and dried (Na$_2$SO$_4$), filtered and MnO$_2$ (6.5 g, 0.074 mol) was added. This mixture was stirred for 4 days. The precipitate was filtered off and the filtrate was evaporated. The residue was purified by column chromatography over silica gel (eluent: PE/EtOAc 5/1). The desired fractions were collected and the solvent was evaporated. Yield: 0.550 g of compound 2 (44.3% yield).

Example B2

Preparation of Compound 3

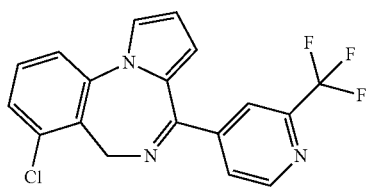 [SMILES: FC(F)(F)c1cc(C2=NCc3c(Cl)cccc3-n3cccc32)ccn1]

Intermediate 5 (0.22 g, 0.58 mmol) was dissolved in POCl$_3$ (4.5 ml). The mixture was stirred and refluxed overnight. Subsequently, the mixture was cooled and poured into water. NaOH was added to pH 7. The mixture was extracted with DCM. The separated organic layer was dried (Na$_2$SO$_4$), filtered and the filtrate was evaporated in vacuo. The residue was purified by preparative HPLC (Synergy column 150×33 mm; mobile phase: 33%-65% CH$_3$CN (0.1% TFA)/H$_2$O (0.1% TFA); flow rate 25 ml/min; 18 min). The desired fractions were collected and the solvent was evaporated in vacuo.

The residue was neutralized with a saturated NaHCO$_3$ solution. The mixture was extracted with DCM. The organic layers were dried (Na$_2$SO$_4$), filtered and the solvent was evaporated. Yield: 0.060 g of compound 3 (30% yield).

Example B3 a) Preparation of Compound 4

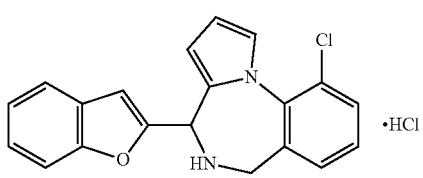 [SMILES: Clc1cccc2c1-n1cccc1C(c1cc3ccccc3o1)NC2 ; Cl]

2-Benzofurancarboxaldehyde (0.541 g, 3.7 mmol) was added to a solution of intermediate 6 (0.75 g, 3.08 mmol) in EtOH (5 ml). The r.m. was stirred and refluxed for 4 h, and was then cooled. After standing overnight, the mixture was concentrated. The residue was purified by flash column chromatography over silica gel (eluent: PE/EtOAc 20/1). The product fractions were collected and the solvent was evaporated to yield 1.0 g of compound 4 (88% yield; .HCl).

b) Preparation of Compound 5

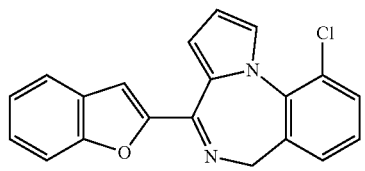 [SMILES: Clc1cccc2c1-n1cccc1C(c1cc3ccccc3o1)=NC2]

Compound 4 (1.0 g, 2.6 mmol) was treated with NH$_3$.H$_2$O (15 ml), and extracted with DCM (50 ml). The layers were separated and dried (Na$_2$SO$_4$), filtered and MnO$_2$ (2.8 g, 32.3 mmol) was added. This mixture was stirred for 2 days. The precipitate was filtered off and the filtrate was evaporated. The residue was dried in vacuo. Yield: 0.720 g of compound 5 (83% yield).

Example B4 a) Preparation of Compound 6

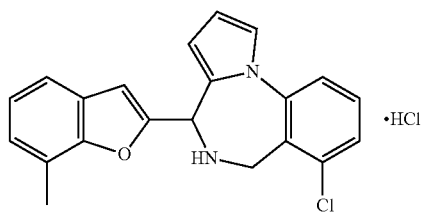 [SMILES: Cc1cccc2cc(C3NCc4c(Cl)cccc4-n4cccc43)oc12 ; Cl]

7-Methyl-2-benzofurancarboxaldehyde (1.18 g, 7.4 mmol) was added to a solution of intermediate 4 (1.5 g, 6.1 mmol) in EtOH (10 ml). The r.m. was stirred and refluxed for 4 h, and was then cooled. After standing overnight, the crystals were filtered off and dried in vacuo. Yield: 1.5 g of compound 6 (65% yield; .HCl).

b) Preparation of Compound 7

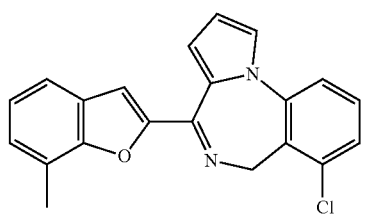 [SMILES: Cc1cccc2cc(C3=NCc4c(Cl)cccc4-n4cccc43)oc12]

Compound 6 (1.5 g, 3.9 mmol) was treated with NH₃·H₂O (15 ml), and extracted with DCM (50 ml). The layers were separated and dried (Na₂SO₄), filtered and MnO₂ (4.07 g, 46.8 mmol) was added. This mixture was stirred for 2 days. The precipitate was filtered off and the filtrate was evaporated. The residue was purified by flash column chromatography over silica gel (eluent: PE/EtOAc 4/1). The desired fractions were collected and the solvent was evaporated. Yield: 0.380 g of compound 7 (28% yield).

Example B5

Preparation of Compound 8

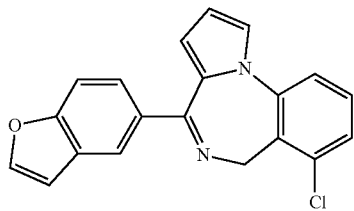 [SMILES: Clc1cccc2c1CN=C(c1ccc3sccc3c1)c1cccn1-2]

Intermediate 7 (0.19 g, 0.541 mmol) was dissolved in POCl₃ (5 ml). The mixture was stirred and refluxed overnight. Subsequently, the mixture was cooled and poured into water. NaOH was added to pH 7. The mixture was extracted with DCM. The separated organic layer was dried (MgSO₄), filtered and the filtrate was evaporated. Yield: 0.164 g of compound 8 (91% yield).

Example B6

Preparation of Compound 9

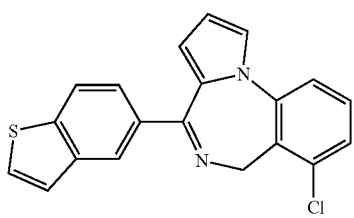

A mixture of intermediate 8 (1.5 g, 4.09 mmol) and POCl₃ (4 ml) was refluxed overnight. Subsequently, the mixture was cooled and poured into water. NaOH was added to pH 8-9. The mixture was extracted with EtOAc. The separated organic layer was dried, filtered and the filtrate was evaporated. The residue was purified by column chromatography (eluent: PE/EtOAc 30/1). The desired fractions were collected and the solvent was evaporated. Yield: 0.67 g of compound 9 (47% yield).

Example B7

Compounds 10, 21, 22, 23 and 24 were obtained as HBr salt forms. These compounds were prepared by using analogous reaction procedures as described in WO02/34752.

Example B8

Preparation of Compounds 201 and 202

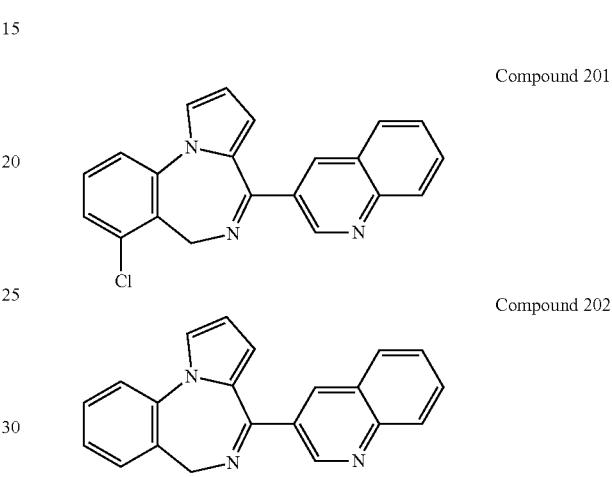

POCl₃ (9274 µl, 99 mmol) was added to intermediate 10 (900 mg). The reaction mixture was refluxed for 5 hours. The excess of POCl₃ was evaporated under reduced pressure. MeOH was added to the resulting oil. The excess MeOH was evaporated. EtOAc (q.s.) and a 2M aqueous solution of NaOH were added to the resulting crude. The two layers were separated and the water layer was extracted with EtOAc. The combined organic layers were dried over anhydrous Na₂SO₄, filtered and evaporated under reduced pressure to yield a crude which was purified over silica (100% Hexane to 100% EtOAc) to yield two pure fractions. Both fractions were triturated in EtO₂ resulting in fraction 1: 412 mg of compound 201; fraction 2: 99.4 mg of compound 202.

By using analogous reaction protocols as described in the foregoing examples, the compounds in Table 1a en Table 1b have been prepared. 'Co. No.' means compound number. 'Pr.' refers to the Example number according to which protocol the compound was synthesized. In case no salt form is indicated, the compound was obtained as a free base.

Compounds wherein $R^3$ and $R^4$ are hydrogen and for which no specific stereochemistry is indicated in Table 1a were obtained as racemic mixtures of R and S enantiomers. In order to obtain the HCl salt forms of the compounds, several procedures known to those skilled in the art were used. In a typical procedure, the compound was dissolved in a solvent such as, for example, 2-propanol, and subsequently a HCl solution in a solvent such as, for example, 2-propanol was added dropwise. Stirring for a certain period of time, typically about 10 minutes, could enhance the rate of the reactions.

TABLE 1a

| Co. No. | Pr. | R¹ | R² | Het | Salt Form |
|---|---|---|---|---|---|
| 10 | B7 | 7-Cl | H | 1-ethyl-pyrazol-3-yl | ·HBr |
| 11 | B4.a | 7-Cl | H | pyridin-2-yl | |
| 12 | B4.a | 7-Cl | H | 6-methyl-pyridin-2-yl | |
| 13 | B1.a | 7-Cl | H | 5-ethyl-pyridin-2-yl | ·HCl |
| 14 | B1.a | 7-Cl | H | 6-ethyl-pyridin-3-yl | ·HCl |
| 15 | B1.a | H | H | 6-trifluoromethyl-pyridin-3-yl | ·HCl |
| 16 | B1.a | 7-Cl | H | 6-trifluoromethyl-pyridin-3-yl | ·HCl |
| 17 | B1.a | 7-F | H | 6-trifluoromethyl-pyridin-3-yl | ·HCl |
| 18 | B1.a | 7-CH₃ | H | 6-trifluoromethyl-pyridin-3-yl | ·HCl |
| 19 | B1.a | 7-Cl | 9-Cl | 6-trifluoromethyl-pyridin-3-yl | ·HCl |
| 20 | B3.a | 7-Cl | H | pyridin-3-yl | |
| 21 | B7 | 7-Cl | H | pyridin-4-yl | ·HBr |
| 22 | B7 | 8-Cl | H | pyridin-4-yl | ·HBr |
| 23 | B7 | 9-Cl | H | pyridin-4-yl | ·HBr |
| 24 | B7 | 10-Cl | H | pyridin-4-yl | ·HBr |
| 25 | B1.a | 7-Cl | H | 2-methyl-pyrimidin-5-yl | ·HCl |
| 26 | B1.a | 7-Cl | H | 2-trifluoromethyl-pyrimidin-5-yl | ·HCl |
| 27 | B1.a | 7-Cl | 10-CH₃ | 2-trifluoromethyl-pyrimidin-5-yl | ·HCl |
| 28 | B1.a | 7-Cl | H | 6-trifluoromethyl-pyridazin-3-yl | ·HCl |
| 29 | B1.a | H | H | benzofuran-2-yl | ·HCl |
| 30 | B1.a | 7-Cl | H | benzofuran-2-yl | ·HCl |
| 4 | B3.a | 10-Cl | H | benzofuran-2-yl | ·HCl |
| 31 | B1.a | 7-Cl | 9-Cl | benzofuran-2-yl | ·HCl |
| 32 | B1.a | 7-CH₃ | H | benzofuran-2-yl | ·HCl |
| 33 | B1.a | 10-CH₃ | H | benzofuran-2-yl | ·HCl |

TABLE 1a-continued
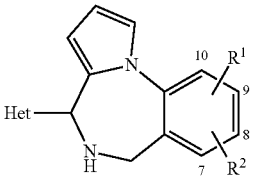
| Co. No. | Pr. | R¹ | R² | Het | Salt Form |
|---|---|---|---|---|---|
| 34 | B1.a | 7-CH₃ | H |  | •HCl |
| 35 | B1.a | 7-Cl | H |  | •HCl |
| 36 | B1.a | 7-Cl | H | 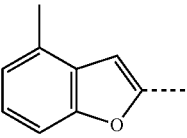 | •HCl |
| 37 | B1.a | 9-Cl | H | 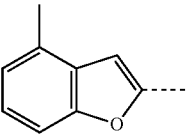 | •HCl |
| 38 | B1.a | H | H | 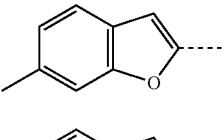 | •HCl |
| 39 | B1.a | 7-Cl | H | 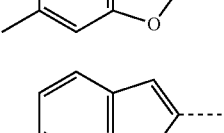 | •HCl |
| 40 | B1.a | 7-CH₃ | H | 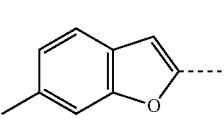 | •HCl |
| 41 | B1.a | 7-Cl | 9-Cl | 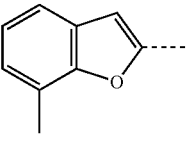 | •HCl |
| 6 | B4.a | 7-Cl | H | 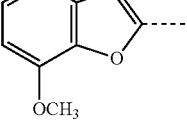 | •HCl |
| 42 | B1.a | 9-Cl | H |  | •HCl |
| 43 | B1.a | 7-Cl | 9-Cl | 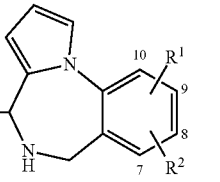 | •HCl |
| 44 | B1.a | 7-Cl | H | 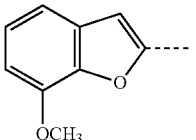 | •HCl |
| 45 | B1.a | 9-Cl | H | 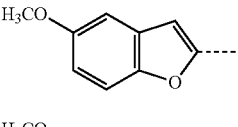 | •HCl |
| 46 | B1.a | 7-Cl | 9-Cl | 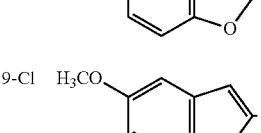 | •HCl |
| 47 | B4.a | 7-Cl | H | 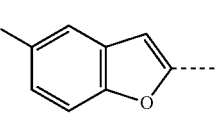 | •HCl |
| 48 | B1.a | 9-Cl | H | 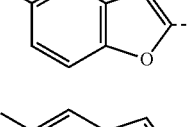 | •HCl |
| 49 | B1.a | 7-Cl | 9-Cl | 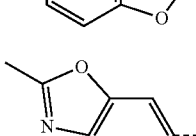 | •HCl |
| 50 | B1.a | 7-Cl | H | 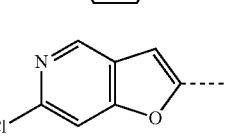 | •HCl |
| 51 | B1.a | 7-Cl | H | 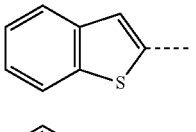 | •HCl |
| 52 | B1.a | H | H | 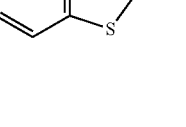 | •HCl |
| 1 | B1.a | 7-CH₃ | H |  | •HCl |

TABLE 1a-continued
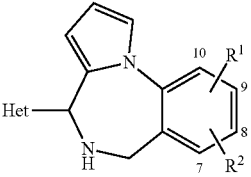
| Co. No. | Pr. | R¹ | R² | Het | Salt Form |
|---|---|---|---|---|---|
| 53 | B1.a | 7-Cl | H | 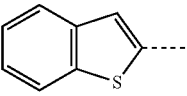 | •HCl |
| 54 | B1.a | 10-Cl | H | 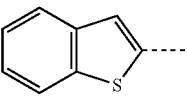 | •HCl |
| 55 | B1.a | 10-CH₃ | H | 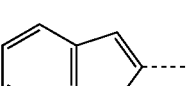 | •HCl |
| 56 | B1.a | 7-Cl | 9-Cl | 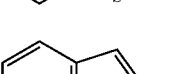 | •HCl |
| 57 | B1.a | 7-Cl | 10-CH₃ | 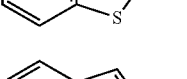 | •HCl |
| 58 | B1.a | 7-Cl | H | 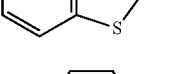 | •HCl |
| 59 | B1.a | 7-Cl | H | 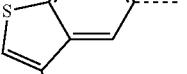 | •HCl |
| 207 | B1.a | 7-Cl | H | 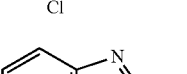 | •HCl |
| 208 | B1.a | 9-Cl | H | 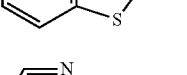 | •HCl |
| 209 | B4.a | 10-Cl | H | 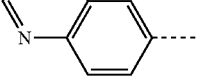 | •HCl |
| 210 | B4.a | 7-Cl | H | 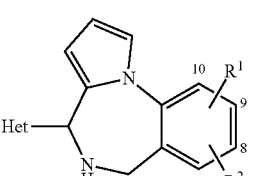 | •HCl |
| 211 | B4.a | 7-CH₃ | H | 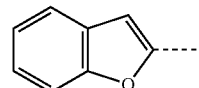 | •HCl |
| 212 | B4.a | H | H | 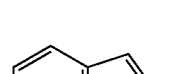 | •HCl |
| 213 | B4.a | 7-CH₃ | H | 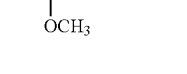 | •HCl |
| 214 | B1.a | 7-Cl | H | 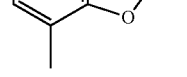 | •HCl |
| 215 | B1.a | 7-Cl | 10-Cl | 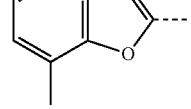 | •HCl |
| 216 | B1.a | 8-Cl | 10-Cl | 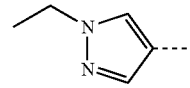 | •HCl |
| 217 | B3.a | 9-Cl | H | 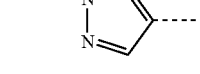 | •HCl |
| 218 | B1.a | 9-Cl | H | 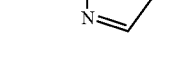 | •HCl |

TABLE 1b

| Co. No. | Pr. | R¹ | R² | Het | Salt Form/Comment |
|---|---|---|---|---|---|
| 60 | B1.b | 7-Cl | H | 1-ethyl-1H-pyrazol-4-yl | |
| 61 | B1.b | 7-Cl | 10-Cl | 1-ethyl-1H-pyrazol-4-yl | |
| 62 | B1.b | 8-Cl | 10-Cl | 1-ethyl-1H-pyrazol-4-yl | |
| 63 | B6 | 7-Cl | H | 3-ethylisoxazol-5-yl | |
| 64 | B6 | 7-Cl | H | 2-ethylthiazol-4-yl | |
| 65 | B6 | 7-Cl | 9-Cl | 2-ethylthiazol-4-yl | |
| 66 | B6 | 7-Cl | H | 5-ethylthiazol-2-yl | |
| 67 | B6 | 7-Cl | 9-Cl | 4-ethylthiazol-2-yl | |
| 68 | B6 | 7-Cl | H | 4-ethylthiazol-2-yl | |
| 69 | B6 | 7-Cl | 9-Cl | 4-ethylthiazol-2-yl | |
| 70 | B6 | 7-Cl | H | 1-isopropyl-2-oxo-1,2-dihydropyridin-4-yl | |
| 71 | B6 | 10-Cl | H | 1-isopropyl-2-oxo-1,2-dihydropyridin-4-yl | |

TABLE 1b-continued
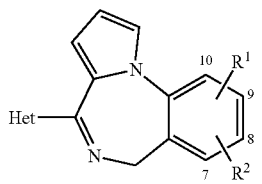
| Co. No. | Pr. | R¹ | R² | Het | Salt Form/Comment |
|---|---|---|---|---|---|
| 72 | B1.b | 7-Cl | H | 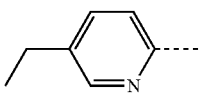 | |
| 73 | B6 | 7-Cl | 9-Cl | 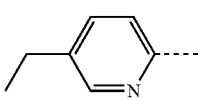 | |
| 74 | B2 | 7-Cl | H | 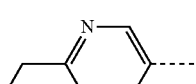 | |
| 75 | B6 | 7-Cl | 8-Cl | 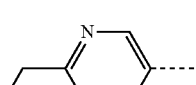 | |
| 76 | B6 | 7-Cl | 9-Cl | 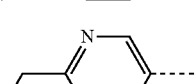 | |
| 77 | B2 | 7-Cl | H | 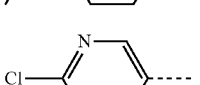 | |
| 78 | B2 | 7-Cl | 9-F | 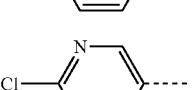 | |
| 79 | B2 | 7-Cl | H | 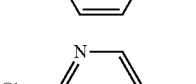 | |
| 80 | B2 | 7-F | H | 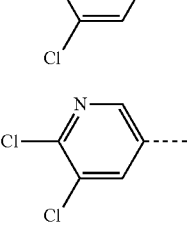 | |
| 81 | B2 | 7-F | 9-F | 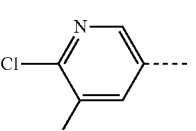 | |
| 82 | B2 | 7-Cl | H | 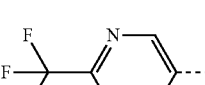 | |
| 83 | B2 | 7-F | H | 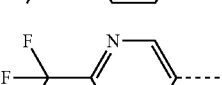 | |

TABLE 1b-continued

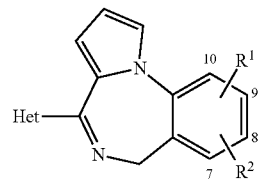

| Co. No. | Pr. | R¹ | R² | Het | Salt Form/ Comment |
|---|---|---|---|---|---|
| 84 | B2 | 7-Cl | 9-Cl | 2-(1,1-difluoroethyl)pyridin-5-yl | |
| 85 | B2 | 7-Cl | 9-F | 2-(1,1-difluoroethyl)pyridin-5-yl | |
| 86 | B2 | 7-F | 9-F | 2-(1,1-difluoroethyl)pyridin-5-yl | |
| 87 | B1.b | H | H | 2-(trifluoromethyl)pyridin-5-yl | |
| 88 | B1.b | 7-CH₃ | H | 2-(trifluoromethyl)pyridin-5-yl | |
| 89 | B1.b | 7-Cl | H | 2-(trifluoromethyl)pyridin-5-yl | |
| 90 | B1.b | 7-F | H | 2-(trifluoromethyl)pyridin-5-yl | |
| 91 | B1.b | 7-Cl | 9-Cl | 2-(trifluoromethyl)pyridin-5-yl | |
| 92 | B2 | 7-Cl | H | 2-acetylpyridin-5-yl | |
| 93 | B2 | 7-F | H | 2-acetylpyridin-5-yl | |
| 94 | B2 | 7-F | 9-F | 2-acetylpyridin-5-yl | |
| 95 | B2 | H | H | 2-methylpyridin-4-yl | |

TABLE 1b-continued
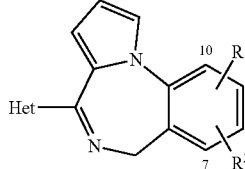
| Co. No. | Pr. | R¹ | R² | Het | Salt Form/Comment |
|---|---|---|---|---|---|
| 96 | B2 | 7-Cl | H | 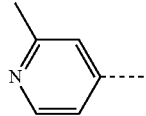 | |
| 97 | B2 | 7-CH₃ | H | 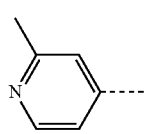 | |
| 3 | B2 | 7-Cl | H | 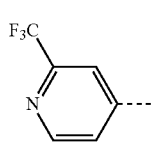 | |
| 98 | B2 | 9-Cl | H | 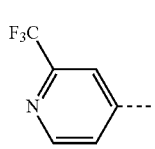 | |
| 99 | B6 | 7-CH₃ | H | 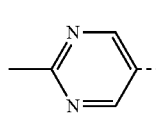 | |
| 100 | B1.b | 7-Cl | H | 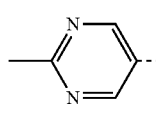 | |
| 101 | B6 | H | H | 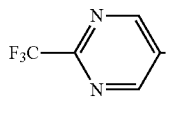 | |
| 102 | B1.b | 7-Cl | H | 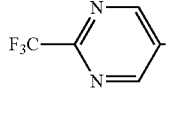 | |
| 103 | B6 | 7-CH₃ | H | 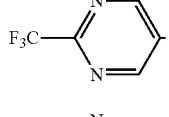 | |
| 104 | B6 | 7-Cl | 9-Cl | 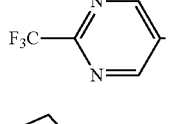 | |
| 105 | B6 | 7-Cl | H | 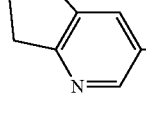 | |

TABLE 1b-continued
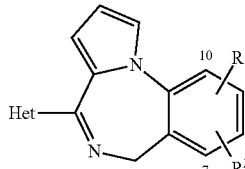
| Co. No. | Pr. | R¹ | R² | Het | Salt Form/ Comment |
|---|---|---|---|---|---|
| 196 | B6 | 7-Cl | H | 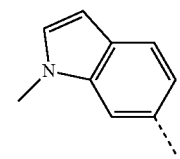 | |
| 106 | B6 | 7-Cl | H | 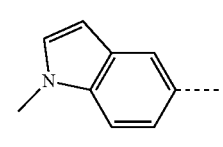 | |
| 107 | B6 | 7-Cl | 9-Cl | 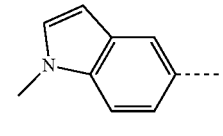 | |
| 108 | B6 | 7-Cl | H | 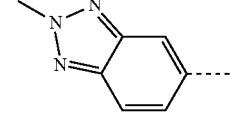 | |
| 109 | B6 | 7-Cl | 9-Cl | 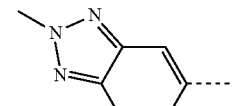 | |
| 110 | B6 | 7-Cl | H | 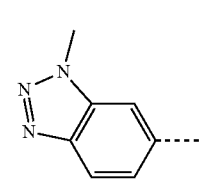 | |
| 111 | B6 | 7-Cl | 9-Cl | 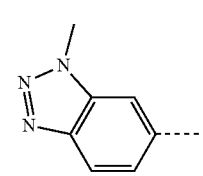 | |
| 112 | B6 | 7-Cl | H | 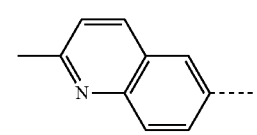 | |
| 113 | B6 | 7-F | H | 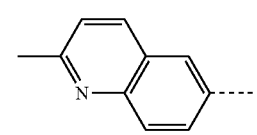 | |

TABLE 1b-continued

| Co. No. | Pr. | R¹ | R² | Het | Salt Form/Comment |
|---|---|---|---|---|---|
| 114 | B6 | 7-F | 9-F | 2-methylquinolin-6-yl | |
| 115 | B3.b | H | H | benzofuran-2-yl | |
| 116 | B3.b | 7-CH₃ | H | benzofuran-2-yl | |
| 117 | B3.b | 10-CH₃ | H | benzofuran-2-yl | |
| 118 | B3.b | 7-Cl | H | benzofuran-2-yl | |
| 119 | B3.b | 9-Cl | H | benzofuran-2-yl | |
| 5 | B3.b | 10-Cl | H | benzofuran-2-yl | |
| 120 | B3.b | 7-Cl | 9-Cl | benzofuran-2-yl | |
| 121 | B3.b | 7-Cl | H | 5-chlorobenzofuran-2-yl | |
| 122 | B3.b | 7-CH₃ | H | 5-chlorobenzofuran-2-yl | |
| 123 | B3.b | 7-Cl | H | 5-fluorobenzofuran-2-yl | |
| 124 | B3.b | 9-Cl | H | 5-fluorobenzofuran-2-yl | |

TABLE 1b-continued
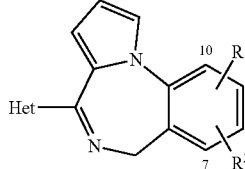
| Co. No. | Pr. | R¹ | R² | Het | Salt Form/Comment |
|---|---|---|---|---|---|
| 125 | B3.b | 7-Cl | 9-Cl | 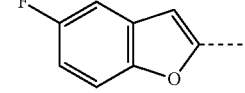 | |
| 126 | B6 | 7-Cl | H | 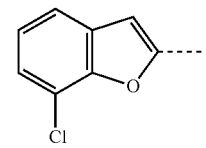 | |
| 127 | B6 | 7-Cl | H | 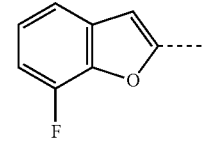 | |
| 128 | B6 | 7-Cl | H |  | |
| 129 | B6 | 7-Cl | 9-Cl |  | |
| 130 | B4.b | H | H | 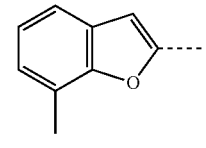 | |
| 7 | B4.b | 7-Cl | H | 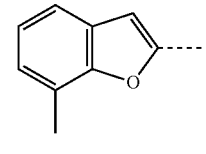 | |
| 131 | B4.b | 7-CH₃ | H | 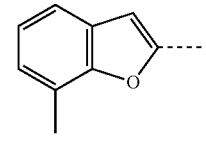 | |
| 132 | B4.b | 7-Cl | H | 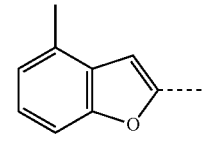 | |

TABLE 1b-continued
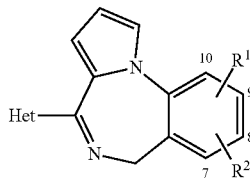
| Co. No. | Pr. | R¹ | R² | Het | Salt Form/Comment |
|---|---|---|---|---|---|
| 133 | B4.b | 9-Cl | H | 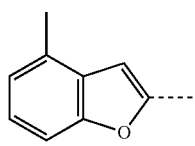 | |
| 134 | B6 | 7-Cl | H | 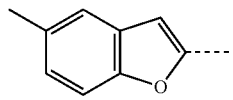 | |
| 135 | B6 | 9-Cl | H | 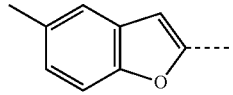 | |
| 136 | B6 | 7-Cl | 9-Cl | 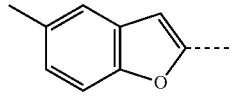 | |
| 137 | B4.b | H | H | 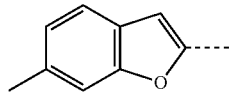 | |
| 138 | B4.b | 7-Cl | H | 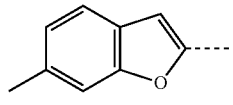 | |
| 139 | B4.b | 7-Cl | 9-Cl | 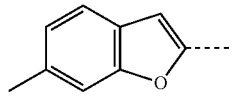 | |
| 140 | B4.b | 7-CH₃ | H | 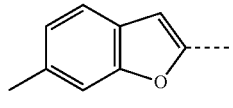 | |
| 141 | B4.b | 7-Cl | H | 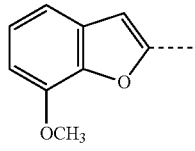 | |
| 142 | B4.b | 9-Cl | H | 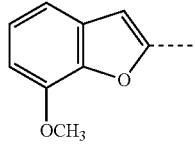 | |

TABLE 1b-continued
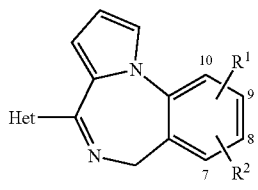
| Co. No. | Pr. | R¹ | R² | Het | Salt Form/ Comment |
|---|---|---|---|---|---|
| 143 | B4.b | 10-Cl | H | 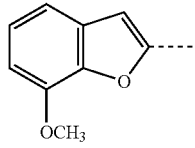 | |
| 144 | B4.b | 7-CH₃ | H | 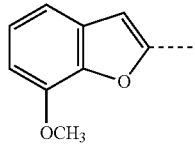 | |
| 145 | B4.b | 7-Cl | 9-Cl | 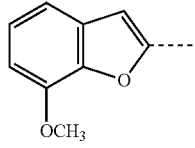 | |
| 146 | B4.b | 7-Cl | H | 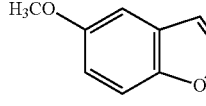 | |
| 147 | B4.b | 9-Cl | H | 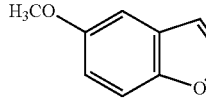 | |
| 148 | B4.b | 7-Cl | 9-Cl | 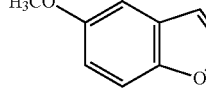 | |
| 149 | B6 | 7-Cl | 9-Cl | 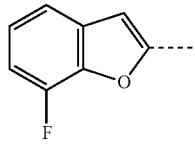 | |
| 150 | B6 | 7-Cl | H | 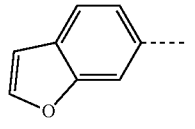 | |
| 151 | B6 | 7-Cl | 10-Cl | 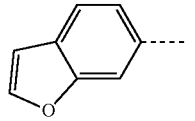 | |
| 8 | B5 | 7-Cl | H | 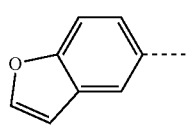 | |

TABLE 1b-continued
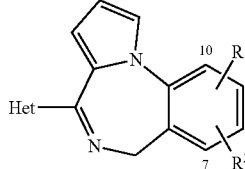
| Co. No. | Pr. | R¹ | R² | Het | Salt Form/Comment |
|---|---|---|---|---|---|
| 152 | B6 | 7-Cl | H | 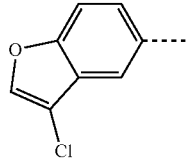 | |
| 153 | B6 | 7-F | H | 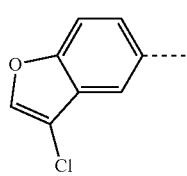 | |
| 154 | B6 | 7-F | 9-F | 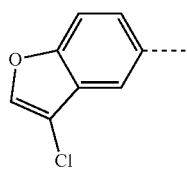 | |
| 155 | B6 | 7-Cl | H | 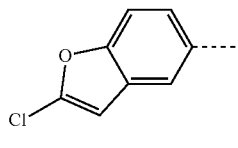 | |
| 156 | B6 | 7-Cl | H | 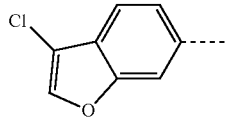 | |
| 157 | B6 | H | H | 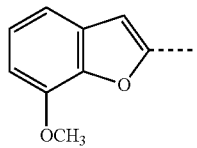 | |
| 158 | B6 | 7-F | 9-F | 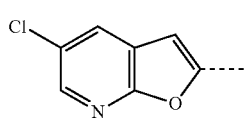 | |
| 159 | B6 | 7-Cl | H | 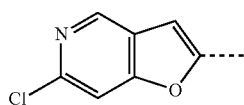 | |
| 160 | B6 | 7-Cl | H | 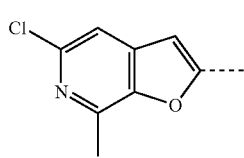 | |

TABLE 1b-continued
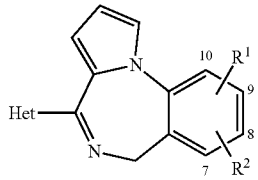
| Co. No. | Pr. | R¹ | R² | Het | Salt Form/Comment |
|---|---|---|---|---|---|
| 161 | B6 | 7-Cl | H | 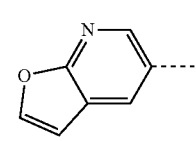 | |
| 162 | B1.b | 7-Cl | H | 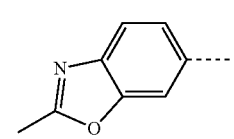 | |
| 163 | B1.b | H | H | 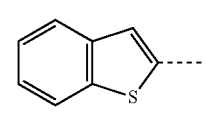 | |
| 2 | B1.b | 7-CH₃ | H | 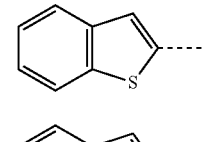 | |
| 164 | B1.b | 10-CH₃ | H | 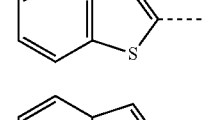 | |
| 165 | B1.b | 7-Cl | H | 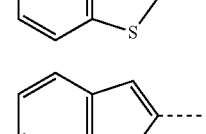 | |
| 166 | B1.b | 9-Cl | H | 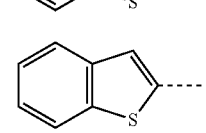 | |
| 167 | B1.b | 10-Cl | H | 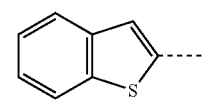 | |
| 168 | B1.b | 7-Cl | 9-Cl | 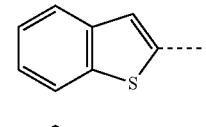 | |
| 169 | B1.b | 7-Cl | 10-CH₃ | 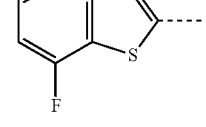 | |
| 170 | B6 | 7-Cl | H |  | |

TABLE 1b-continued
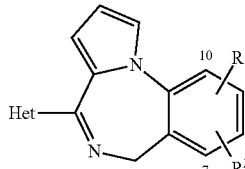
| Co. No. | Pr. | R¹ | R² | Het | Salt Form/Comment |
|---|---|---|---|---|---|
| 171 | B6 | 7-Cl | 9-Cl | 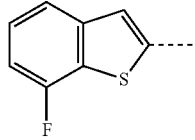 | |
| 172 | B6 | 7-Cl | H | 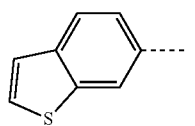 | |
| 9 | B6 | 7-Cl | H | 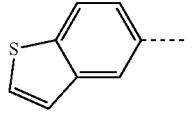 | |
| 173 | B6 | 9-Cl | H | 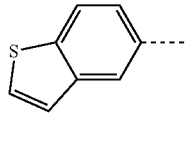 | |
| 174 | B6 | 10-Cl | H | 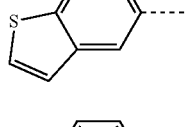 | |
| 175 | B6 | 7-F | H | 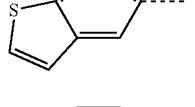 | |
| 176 | B6 | 7-F | 9-F | 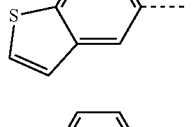 | |
| 177 | B1.b | 7-Cl | H | 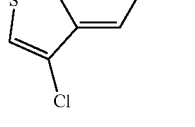 | |
| 178 | B1.b | 9-Cl | H | 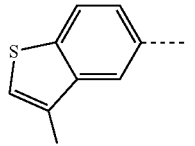 | |

TABLE 1b-continued
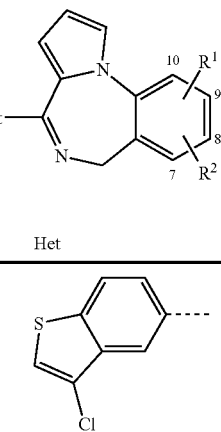
| Co. No. | Pr. | R¹ | R² | Het | Salt Form/Comment |
|---|---|---|---|---|---|
| 179 | B1.b | 10-Cl | H | 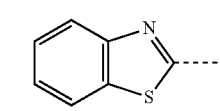 | |
| 180 | B1.b | 7-Cl | H | 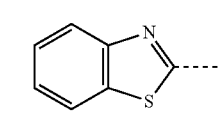 | |
| 181 | B6 | 7-Cl | H | 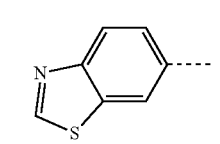 | •HCl |
| 182 | B6 | H | H | 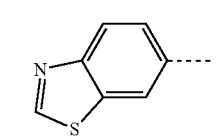 | |
| 183 | B6 | 7-CH₃ | H | | |
| 184 | B6 | 7-Cl | H | 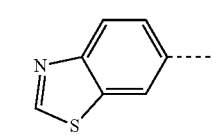 | |
| 185 | B6 | 9-Cl | H | 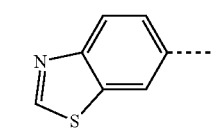 | |
| 186 | B6 | 10-Cl | H | 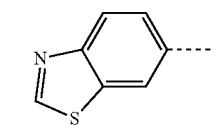 | |
| 187 | B6 | 7-Cl | 9-Cl | 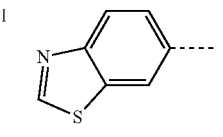 | |
| 188 | B6 | 7-Cl | H | 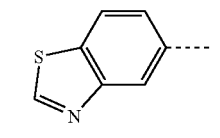 | |

TABLE 1b-continued
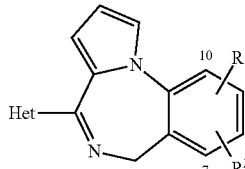
| Co. No. | Pr. | R¹ | R² | Het | Salt Form/ Comment |
|---|---|---|---|---|---|
| 189 | B6 | 7-F | H | 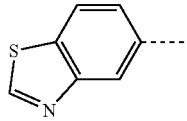 | |
| 190 | B6 | 7-F | 9-F | 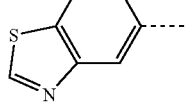 | |
| 191 | B6 | 7-Cl | H | 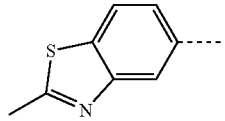 | |
| 192 | B6 | 7-F | H | 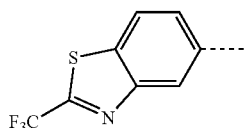 | |
| 193 | B6 | 7-Cl | H | 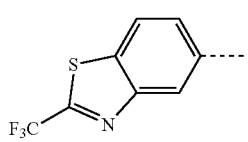 | |
| 194 | B6 | 7-Cl | H | 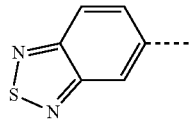 | |
| 195 | B6 | 7-Cl | H | 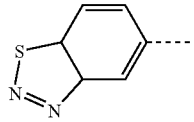 | |
| 197 | B8 | 7-Cl | H | 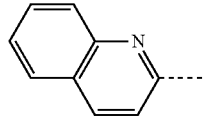 | |
| 198 | B8 | 7-Cl | H | 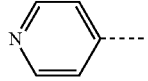 | |
| 199 | B8 | 7-Cl | H | 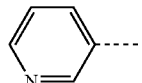 | |

TABLE 1b-continued

| Co. No. | Pr. | R¹ | R² | Het | Salt Form/ Comment |
|---|---|---|---|---|---|
| 200 | B1.b | 7-Cl | H | quinoxalin-2-yl | |
| 201 | B8 | 7-Cl | H | quinolin-3-yl | |
| 202 | B8 | H | H | quinolin-3-yl | |
| 203 | B8 | 9-Cl | H | pyridin-4-yl | |
| 204 | B8 | 9-Cl | H | 1H-benzimidazol-5-yl | |
| 205 | B8 | 7-Cl | H | 1H-benzimidazol-5-yl | 80% pure, containing 20% dehalogenated product |
| 206 | B8 | 9-Cl | H | quinolin-3-yl | |

C. Analytical Results

LCMS—General Procedure A

The HPLC measurement was performed using an Agilent 1100 module comprising a pump, a diode-array detector (DAD) (wavelength used 220 nm), a column heater and a column as specified in the respective methods below. Flow from the column was split to a Agilent MSD Series G1946C and G1956A. MS detector was configured with API-ES (atmospheric pressure electrospray ionization). Mass spectra were acquired by scanning from 100 to 1000. The capillary needle voltage was 2500 V for positive and 3000 V for negative ionization mode. Fragmentation voltage was 50 V. Drying gas temperature was maintained at 350° C. at a flow of 10 l/min.

LCMS—General Procedure B

The HPLC measurement was performed using an Alliance HT 2790 (Waters) system comprising a quaternary pump with degasser, an autosampler, a column oven (set at 40° C., unless otherwise indicated), a diode-array detector (DAD) and a column as specified in the respective methods below. Flow from the column was split to a MS spectrometer. The MS detector was configured with an electrospray ionization source. Mass spectra were acquired by scanning from 100 to 1000 in 1 second using a dwell time of 0.1 second. The capillary needle voltage was 3 kV and the source temperature was maintained at 140° C. Nitrogen was used as the nebulizer gas. Data acquisition was performed with a Waters-Micromass MassLynx-Openlynx data system.

LCMS—General Procedure C

The LC measurement was performed using an Acquity UPLC (Waters) system comprising a binary pump, a sample organizer, a column heater (set at 55° C.), a diode-array detector (DAD) and a column as specified in the respective methods below. Flow from the column was split to a MS spectrometer. The MS detector was configured with an electrospray ionization source. Mass spectra were acquired by scanning from 100 to 1000 in 0.18 seconds using a dwell time of 0.02 seconds. The capillary needle voltage was 3.5 kV and the source temperature was maintained at 140° C. Nitrogen was used as the nebulizer gas. Data acquisition was performed with a Waters-Micromass MassLynx-Openlynx data system.

LCMS—General Procedure D

The HPLC measurement was performed using a Waters acquity H-class UPLC system comprising a quaternary pump with degasser, an autosampler, a column oven with a column heater. This was coupled to a waters TUV (Tunable UV) detector and waters TQD ESI (electrospray ionization) mass spectrometer. The MS detector was configured with an electrospray ionization source. A waters acquity UPLC BEH C18 1.7 µm 2.1×50 mm column was used. Column temperature was 30° C. and flow rate 0.7 mL/min unless otherwise noted. Mass ES positive mode spectra were acquired by scanning from 151 to 1000 in 0.1 second. ES negative mode spectra were acquired by scanning from 151 to 1000 in 0.1 second. The capillary needle voltage was 2 kV and the source temperature was maintained at 140° C. Nitrogen was used as the nebulizer gas. Data acquisition was performed with a Waters-Micromass MassLynx-Openlynx data system.

LCMS Method 1

In addition to general procedure A: Reversed phase HPLC was carried out on a YMC-Pack ODS-AQ, 50×2.0 mm 5 µm column with a flow rate of 0.8 ml/min. Two mobile phases (mobile phase A: water with 0.1% TFA; mobile phase B: acetonitrile with 0.05% TFA) were used. First, 100% A was hold for 1 minute. Then a gradient was applied to 40% A and 60% B in 4 minutes and hold for 2.5 minutes. Typical injection volumes of 2 µl were used. Oven temperature was 50° C. (MS polarity: positive)

LCMS Method 2

In addition to general procedure A: Reversed phase HPLC was carried out on a YMC-Pack ODS-AQ, 50×2.0 mm 5 µm column with a flow rate of 0.8 ml/min. 2 mobile phases (mobile phase A: water with 0.1% TFA; mobile phase B: $CH_3CN$ with 0.05% TFA) were used. First, 90% A and 10% B was hold for 0.8 min. Then a gradient was applied to 20% A and 80% B in 3.7 min and hold for 3 min. Typical injection volumes of 2 µl were used. Oven temperature was 50° C. (MS polarity: positive)

LCMS Method 3

In addition to general procedure A: Reversed phase HPLC was carried out on an Ultimate XB-C18, 50×2.1 mm 5 µm column with a flow rate of 0.8 ml/min. Two mobile phases (mobile phase C: 10 mmol/l $NH_4HCO_3$; mobile phase D: $CH_3CN$) were used. First, 100% C was hold for 1 minute. Then a gradient was applied to 40% C and 60% D in 4 minutes and hold for 2.5 min. Typical injection volumes of 2 µl were used. Oven temperature was 50° C. (MS polarity: positive)

LCMS Method 4

In addition to general procedure B: Reversed phase HPLC was carried out on an Xterra MS C18 column (3.5 µm, 4.6×100 mm) with a flow rate of 1.6 ml/min. Three mobile phases (mobile phase A: 95% 25 mM ammoniumacetate+ 5% acetonitrile; mobile phase B: acetonitrile; mobile phase C: methanol) were employed to run a gradient condition from 100% A to 1% A, 49% B and 50% C in 6.5 minutes, to 1% A and 99% B in 1 minute and hold these conditions for 1 minute and reequilibrate with 100% A for 1.5 minutes. An injection volume of 10 µl was used. Cone voltage was 10 V for positive ionization mode and 20 V for negative ionization mode.

LCMS Method 5

In addition to general procedure A: Reversed phase HPLC was carried out on a YMC-Pack ODS-AQ, 50×2.0 mm 5 µm column with a flow rate of 0.8 ml/min. Two mobile phases (mobile phase A: water with 0.1% TFA; mobile phase B: acetonitrile with 0.05% TFA) were used. First, 70% A and 30% B was hold for 0.8 minutes. Then a gradient was applied to 10% A and 90% B in 3.2 minutes and hold for 3.5 minutes. Typical injection volumes of 2 µl were used. Oven temperature was 50° C. (MS polarity: positive)

LCMS Method 6

In addition to general procedure A: Reversed phase HPLC was carried out on an Ultimate XB-C18, 50×2.1 mm 5 µm column with a flow rate of 0.8 ml/min. Two mobile phases (mobile phase C: 10 mmol/L $NH_4HCO_3$; mobile phase D: acetonitrile) were used. First, 90% C and 10% D was hold for 0.8 minutes. Then a gradient was applied to 20% C and 80% D in 3.7 minutes and hold for 3 minutes. Typical injection volumes of 2 µl were used. Oven temperature was 50° C. (MS polarity: positive)

LCMS Method 7

In addition to general procedure C: Reversed phase UPLC (Ultra Performance Liquid Chromatography) was carried out on a bridged ethylsiloxane/silica hybrid (BEH) C18 column (1.7 µm, 2.1×50 mm; Waters Acquity) with a flow rate of 0.8 ml/min. Two mobile phases (10 mM ammonium acetate in $H_2O$/acetonitrile 95/5; mobile phase B: acetonitrile) were used to run a gradient condition from 95% A and 5% B to 5% A and 95% B in 1.3 minutes and hold for 0.3 minutes. An injection volume of 0.5 µl was used. Cone voltage was 10 V for positive ionization mode and 20 V for negative ionization mode.

LCMS Method 8

In addition to general procedure D: Solvent A: water with 0.1% formic acid; Solvent B: acetonitrile with 0.1% formic acid. In 1.75 min from 95% A, 5% B to 95% B, 5% A, then 0.25 min 95% B, 5% A. with 0.75 min reequilibration towards 5% B. UV detection wavelength: 254 nm, MS polarity: positive and negative. Cone voltage was 10 V for positive and negative ionization mode. Typical injection volumes of 1 µl were used.

Melting Points

For a number of compounds, melting points (m.p.) were determined with a WRS-2A melting point apparatus purchased from Shanghai Precision and Scientific Instrument Co. Ltd. Melting points were measured with a linear heating up rate of 0.2-5.0° C./min The reported values are melt ranges. The maximum temperature was 300° C.

For compound 20, the m.p. was determined with a DSC823e (Mettler-Toledo). The m.p. was measured with a temperature gradient of 30° C./minute. Maximum temperature was 400° C. The value is indicated as a peak value.

The results of the analytical measurements are shown in table 2.

TABLE 2

Retention time ($R_t$) in min., [M + H]$^+$ peak (protonated molecule), and m.p. (melting point in ° C.). ("n.d." means not determined; "dec" means decomposed).

| Co. No. | $R_t$ | [M + H]$^+$ | LCMS Method | m.p. (° C.) |
|---|---|---|---|---|
| 1 | 3.74 | 331 | 2 | 242.4-247.7 |
| 2 | 3.79 | 329 | 2 | 108.9-181.5 |
| 3 | 3.27 | 362 | 2 | 158.2-160.6 |
| 5 | 3.63 | 333 | 2 | 159.9-160.8 |
| 7 | 3.76 | 347 | 2 | 175.2-177.3 |
| 8 | 3.26 | 333 | 2 | 163.9-164.1 |
| 9 | 3.69 | 349 | 2 | 182.5-154.9 |
| 13 | 3.52 | 324 | 2 | dec |
| 14 | 3.78 | 324 | 1 | — |
| 15 | 4.50 | 330 | 1 | 240.8-241.3 |
| 16 | 3.50 | 364 | 2 | 200.1-201.9 |
| 17 | 4.25 | 348 | 1 | 238.9-240.4 |
| 18 | 3.47 | 344 | 2 | 244.7-246.5 |
| 19 | 3.60 | 398 | 2 | 244.4-246.1 |
| 20 | n.d. | n.d. | — | 185.21 |
| 21 | 4.89 | 296 | 4 | — |
| 25 | 3.75 | 311 | 1 | 193.7-200.1 |
| 26 | 4.63 | 365 | 1 | 249.0-252.0 |
| 28 | 4.15 | 365 | 1 | 175.0-178.0 |
| 29 | 3.70 | 301 | 2 | 230.2-232.7 |
| 30 | 3.69 | 335 | 2 | 233.6-235.0 |
| 31 | 3.78 | 369 | 2 | 234.6-237.1 |
| 32 | 3.69 | 315 | 2 | — |
| 33 | 3.56 | 315 | 2 | dec |
| 34 | 3.85 | 349 | 2 | 245.3-248.5 |
| 35 | 3.89 | 369 | 2 | 208.2-214.0 |
| 36 | 3.49 | 349 | 2 | 241.8-243.2 |
| 37 | 3.96 | 349 | 2 | 232.4-232.9 |
| 38 | 3.68 | 315 | 2 | 248.1-252.6 |
| 39 | 3.72 | 349 | 2 | 176.2-176.8 |
| 40 | 3.80 | 329 | 2 | 244.4-245.8 |
| 41 | 4.13 | 383 | 2 | 267.1-268.2 |
| 42 | 3.89 | 365 | 2 | 238.9-240.2 |
| 43 | 3.87 | 399 | 2 | 219.1-220.9 |
| 44 | 3.37 | 365 | 2 | 225.8-226.4 |
| 45 | 6.51 | 365 | 3 | 225.6-230.9 |
| 46 | 3.69 | 399 | 2 | 241.3-243.8 |
| 47 | 3.57 | 353 | 2 | 115.3-116.4 |
| 48 | 3.73 | 353 | 2 | 228.9-229.3 |
| 49 | 3.83 | 387 | 2 | 234.8-235.4 |
| 50 | 2.80 | 350 | 2 | — |
| 51 | 2.86 | 370 | 2 | — |
| 52 | 3.80 | 317 | 2 | 194.4-194.9 |
| 53 | 3.87 | 351 | 2 | 189.9-190.8 |
| 55 | 3.78 | 331 | 2 | dec |
| 56 | 3.93 | 385 | 2 | 236.6-238.6 |
| 57 | 3.80 | 365 | 2 | 253.5-255.1 |
| 58 | 4.02 | 385 | 2 | 206.0-208.0 |
| 59 | 3.58 | 352 | 2 | 223.5-231.4 |
| 60 | 3.95 | 311 | 1 | 154.3-156.6 |
| 61 | 3.36 | 345 | 2 | 101.0-108.3 |
| 62 | 3.30 | 345 | 2 | 185.5-187.4 |
| 63 | 4.59 | 312 | 1 | 156.0-156.9 |
| 64 | 3.46 | 328 | 2 | 119.4-123.5 |
| 65 | 3.47 | 362 | 2 | — |
| 66 | 3.45 | 328 | 2 | 142.8-144.8 |
| 67 | 3.96 | 362 | 2 | — |
| 68 | 3.50 | 328 | 2 | 142.0-143.1 |
| 69 | 4.12 | 362 | 2 | 144.7-145.4 |
| 70 | 4.75 | 352 | 1 | — |
| 71 | 5.00 | 352 | 1 | — |
| 72 | 3.34 | 322 | 2 | 198.0-199.5 |
| 73 | 3.63 | 356 | 2 | — |
| 74 | 6.00 | 322 | 3 | 162.3-163.0 |
| 75 | 3.38 | 356 | 2 | 140.1-143.0 |
| 76 | 3.21 | 356 | 2 | 170.2-171.9 |
| 77 | 3.03 | 328 | 2 | 171.7-173.1 |
| 78 | 2.72 | 346 | 2 | 146.0-148.0 |
| 79 | 3.74 | 362 | 2 | 153.5-154.2 |
| 80 | 3.26 | 346 | 2 | 157.2-157.9 |
| 81 | 3.47 | 364 | 2 | 175.7-178.0 |
| 82 | 3.00 | 358 | 2 | 176.1-176.8 |
| 83 | 4.01 | 342 | 1 | 149.1-149.6 |
| 84 | 3.46 | 392 | 2 | 122.5-124.1 |
| 85 | 3.15 | 376 | 2 | — |
| 86 | 4.07 | 360 | 1 | 128.8-129.6 |
| 87 | 4.40 | 328 | 1 | — |
| 88 | 3.42 | 342 | 2 | 135.1-136.6 |
| 89 | 3.58 | 362 | 2 | 175.3-176.6 |
| 90 | 4.22 | 346 | 1 | — |
| 91 | 3.79 | 396 | 2 | 147.8-149.1 |
| 92 | 3.92 | 336 | 1 | 186.1-187.7 |
| 94 | 3.75 | 338 | 1 | 214.2-215.9 |
| 95 | 5.37 | 274 | 3 | 231.5-232.8 |
| 96 | 4.05 | 308 | 1 | 188.4-190.0 |
| 97 | 3.92 | 288 | 1 | 178.5-180.0 |
| 98 | 3.77 | 362 | 2 | — |
| 99 | 3.87 | 289 | 1 | 177.0-177.9 |
| 100 | 3.92 | 309 | 1 | 228.6-230.1 |
| 101 | 4.54 | 329 | 1 | 133.2-134.2 |
| 102 | 5.59 | 363 | 1 | 142.4-145.0 |
| 103 | 4.40 | 343 | 1 | 151.4-153.9 |
| 104 | 4.44 | 397 | 2 | 180.5-181.9 |
| 105 | 2.73 | 334 | 2 | 182.7-184.4 |
| 106 | 3.83 | 346 | 2 | — |
| 107 | 3.65 | 380 | 2 | 210.9-211.5 |
| 108 | 3.02 | 348 | 2 | 250.0-252.0 |
| 109 | 3.26 | 382 | 2 | 213.4-216.0 |
| 110 | 3.90 | 348 | 1 | 222.4-223.7 |
| 111 | 3.03 | 382 | 2 | 224.1-224.6 |
| 112 | 5.97 | 358 | 3 | — |
| 113 | 5.75 | 342 | 3 | — |
| 114 | 5.86 | 360 | 3 | 209.5-210.0 |
| 115 | 3.58 | 299 | 2 | — |
| 116 | 3.54 | 313 | 2 | 133.6-136.0 |
| 117 | 3.40 | 313 | 2 | 145.6-146.5 |
| 118 | 3.57 | 333 | 2 | 180.1-182.5 |
| 119 | 3.65 | 333 | 2 | 206.3-208.9 |
| 120 | 3.76 | 367 | 2 | 228.9-230.1 |
| 121 | 2.41 | 367 | 5 | 204.4-207.0 |
| 122 | 3.83 | 347 | 2 | 200.4-202.7 |
| 123 | 3.55 | 351 | 2 | 186.6-186.7 |
| 124 | 3.66 | 351 | 2 | 173.6-175.1 |
| 125 | 3.88 | 385 | 2 | 173.6-175.4 |
| 126 | 3.70 | 367 | 2 | 190.3-192.6 |
| 127 | 3.54 | 351 | 2 | 198.6-199.4 |
| 128 | 3.64 | 369 | 2 | 182.0-184.3 |
| 129 | 4.03 | 403 | 2 | 202.0-202.3 |
| 130 | 3.63 | 313 | 2 | 126.3-128.5 |
| 131 | 3.87 | 327 | 2 | 197.2-197.5 |
| 132 | 3.65 | 347 | 2 | 262.0-263.2 |
| 133 | 3.79 | 347 | 2 | 218.7-219.5 |
| 134 | 3.80 | 347 | 2 | 178.3-180.6 |
| 135 | 3.82 | 347 | 2 | 156.5-157.1 |
| 136 | 4.07 | 381 | 2 | 192.9-193.2 |
| 137 | 3.57 | 313 | 2 | 232.0-237.9 |
| 138 | 3.84 | 347 | 2 | 197.0-198.2 |
| 139 | 4.07 | 381 | 2 | 198.2-201.3 |
| 140 | 3.87 | 327 | 2 | 138.1-138.3 |
| 141 | 3.76 | 363 | 2 | 180.7-182.2 |
| 142 | 3.85 | 363 | 2 | 186.2-187.9 |
| 143 | 6.41 | 363 | 3 | — |
| 144 | 3.80 | 343 | 2 | 188.8-190.1 |
| 145 | 5.33 | 397 | 6 | — |
| 146 | 3.45 | 363 | 2 | 151.1-152.3 |
| 147 | 3.75 | 363 | 2 | 215.1-216.7 |
| 148 | 3.68 | 397 | 2 | 108.6-109.9 |
| 149 | 3.85 | 385 | 2 | 207.2-209.1 |
| 150 | 3.50 | 333 | 2 | — |
| 151 | 7.62 | 367 | 3 | 206.4-207.7 |

TABLE 2-continued

Retention time ($R_t$) in min., [M + H]⁺ peak (protonated molecule), and m.p. (melting point in ° C.). ("n.d." means not determined; "dec" means decomposed).

| Co. No. | $R_t$ | [M + H]⁺ | LCMS Method | m.p. (° C.) |
|---|---|---|---|---|
| 152 | 3.31 | 367 | 2 | 209.3–210.4 |
| 153 | 3.74 | 351 | 2 | 185.4–186.1 |
| 154 | 3.81 | 369 | 2 | 173.1–177.3 |
| 155 | 3.89 | 367 | 2 | — |
| 156 | 3.91 | 367 | 2 | — |
| 157 | 3.59 | 329 | 2 | 159.0–162.3 |
| 158 | 3.24 | 370 | 2 | 235.0–235.5 |
| 159 | 3.00 | 368 | 2 | 219.0–219.9 |
| 160 | 3.37 | 382 | 2 | — |
| 161 | 3.74 | 334 | 1 | 208.1–209.0 |
| 162 | 2.84 | 348 | 2 | 244.8–246.4 |
| 163 | 3.73 | 315 | 2 | 171.1–173.6 |
| 164 | 3.77 | 329 | 2 | 190.1–190.3 |
| 165 | 3.95 | 349 | 2 | 162.0–165.5 |
| 166 | 3.95 | 349 | 2 | 253.5–257.7 |
| 167 | 3.98 | 349 | 2 | 178.3–178.8 |
| 168 | 4.07 | 383 | 2 | 155.3–157.6 |
| 169 | 3.96 | 363 | 2 | — |
| 170 | 4.39 | 367 | 2 | 170.6–171.7 |
| 171 | 5.01 | 401 | 2 | 184.4–185.6 |
| 172 | 3.07 | 349 | 2 | 186.0–188.4 |
| 173 | 3.48 | 349 | 2 | 205.4–207.7 |
| 174 | 3.49 | 349 | 2 | 211.8–213.0 |
| 175 | 3.17 | 333 | 2 | — |
| 176 | 3.29 | 351 | 2 | 176.4–178.1 |
| 177 | 3.37 | 383 | 2 | dec |
| 178 | 4.05 | 383 | 2 | — |
| 179 | 4.02 | 383 | 2 | — |
| 180 | 5.06 | 350 | 2 | 177.4–177.8 |
| 181 | 5.25 | 350 | 2 | 174.3–176.0 |
| 182 | 5.83 | 316 | 3 | 179.1–181.1 |
| 183 | 4.71 | 330 | 6 | 232.5–235.4 |
| 184 | 3.20 | 350 | 2 | 231.5–232.8 |
| 185 | 3.28 | 350 | 2 | 196.8–198.0 |
| 186 | 3.24 | 350 | 2 | 187.8–189.0 |
| 187 | 3.38 | 384 | 2 | 224.0–225.6 |
| 188 | 5.99 | 350 | 3 | 172.5–173.8 |
| 189 | 3.79 | 334 | 1 | — |
| 190 | 5.86 | 352 | 3 | 149.9–153.4 |
| 191 | 3.37 | 364 | 2 | 164.6–165.4 |
| 192 | 3.86 | 402 | 2 | 135.0–139.5 |
| 193 | 3.94 | 418 | 2 | — |
| 194 | 3.03 | 351 | 2 | 200.8–202.7 |
| 195 | 3.23 | 351 | 2 | 207.7–208.1 |
| 196 | 3.75 | 346 | 2 | 238.4–240.9 |
| 197 | 1.22 | 344 | 7 | — |
| 198 | 0.97 | 294 | 7 | — |
| 199 | 1.17 | 294 | 8 | — |
| 200 | 1.29 | 345 | 8 | — |
| 201 | 1.13 | 344 | 7 | — |
| 202 | 1.03 | 310 | 7 | — |
| 203 | 0.98 | 294 | 7 | — |
| 204 | 0.87 | 333 | 7 | — |
| 205 | 0.85 | 333 | 7 | — |
| 206 | 1.14 | 344 | 7 | — |
| 207 | 1.30 | 347 | 8 | — |

¹H NMR

For a number of compounds, ¹H NMR spectra were recorded on a Bruker DPX-300 or on a Bruker DPX-400 spectrometer with standard pulse sequences, operating at 300 MHz and 400 MHz respectively, using CHLOROFORM-d (deuterated chloroform, CDCl₃) or DMSO-d₆ (deuterated DMSO, dimethyl-d6 sulfoxide) as solvents.

Co. No. 118: (300 MHz, CDCl₃) δ ppm 4.26 (d, J=12.1 Hz, 1 H) 5.65 (d, J=12.3 Hz, 1 H) 6.46-6.57 (m, 1 H) 6.94 (dd, J=4.0, 1.3 Hz, 1 H) 7.20 (s, 1 H) 7.21-7.43 (m, 6 H) 7.56-7.65 (m, 2 H).

Co. No. 115: (400 MHz, CDCl₃) δ ppm 4.49 (br. s., 1 H) 5.01 (br. s., 1 H) 6.47-6.58 (m, 1 H) 6.86-7.02 (m, 1 H) 7.15-7.45 (m, 7 H) 7.52 (d, J=7.3 Hz, 1 H) 7.56-7.61 (m, 2 H).

Co. No. 116: (300 MHz, CDCl₃) δ ppm 2.66 (s, 3 H) 4.23 (d, J=11.3 Hz, 1 H) 5.35 (d, J=12.4 Hz, 1 H) 6.55 (br. s., 1 H) 7.03 (br. s., 1 H) 7.19-7.52 (m, 7 H) 7.58-7.68 (m, 2 H).

Co. No. 1: (300 MHz, DMSO-d₆) δ ppm 2.59 (s, 3 H) 3.69 (d, J=13.6 Hz, 1 H) 4.39 (d, J=13.9 Hz, 1 H) 5.64 (br. s., 1 H) 6.15-6.28 (m, 1 H) 6.28-6.39 (m, 1 H) 7.27-7.57 (m, 7 H) 7.81-8.11 (m, 2 H) 10.31 (br. s., 1 H) 10.94 (br. s., 1 H).

Co. No. 82: (300 MHz, CDCl₃) δ ppm 4.20 (br. s., 1 H), 5.52 (br. s., 1 H), 6.42-6.54 (m, 2 H), 6.58 (s, 1 H), 7.23-7.33 (m, 2 H), 7.33-7.46 (m, 3 H), 7.68 (d, J=8.7 Hz, 1 H), 7.87 (s, 1 H).

Co. No. 88: (300 MHz, CDCl₃) δ ppm 2.64 (s, 3 H) 4.21 (br. s., 1 H) 5.28 (br. s., 1 H) 6.36-6.63 (m, 2 H) 7.16-7.37 (m, 3 H) 7.44 (br. s., 1 H) 7.71 (d, J=8.1 Hz, 1 H) 8.24 (d, J=7.5 Hz, 1 H) 9.02 (s, 1 H).

Co. No. 150: (400 MHz, CDCl₃) δ ppm 4.23 (br. s., 1 H) 5.58 (br. s., 1 H) 6.49 (br. s., 1 H) 6.58 (br. s., 1 H) 6.80 (br. s., 1 H) 7.28-7.35 (m, 2 H) 7.39 (br. s., 2 H) 7.53-7.66 (m, 1 H) 7.69 (br. s., 2 H) 7.90 (br. s., 1 H).

Co. No. 130: (300 MHz, CDCl₃) δ ppm 2.62 (s, 3 H) 4.49 (br. s., 1 H) 5.02 (br. s., 1 H) 6.39-6.58 (m, 1 H) 6.84-6.98 (m, 1 H) 7.07-7.22 (m, 3 H) 7.29-7.35 (m, 1 H) 7.35-7.47 (m, 4 H) 7.53 (d, J=7.2 Hz, 1 H).

Co. No. 184: (400 MHz, CDCl₃) δ ppm 4.23 (br. s., 1 H) 5.56 (br. s., 1 H) 6.42-6.51 (m, 1 H) 6.53 (dd, J=3.8, 1.5 Hz, 1 H) 7.28-7.35 (m, 2 H) 7.39 (m, J=3.1, 3.1, 2.1 Hz, 2 H) 7.89 (dd, J=8.5, 1.5 Hz, 1 H) 8.11 (d, J=8.5 Hz, 1 H) 8.37 (d, J=1.5 Hz, 1 H) 9.06 (s, 1 H).

Co. No. 7: (300 MHz, CDCl₃) δ ppm 2.60 (s, 3 H) 4.23 (d, J=8.9 Hz, 1 H) 5.62 (d, J=9.4 Hz, 1 H) 6.50 (br. s., 1 H) 6.92 (br. s., 1 H) 7.17 (m, J=9.8 Hz, 3 H) 7.23-7.49 (m, 5 H).

Co. No. 117: (400 MHz, DMSO-d₆) δ ppm 2.32 (s, 3 H) 4.13 (d, J=10.8 Hz, 1 H) 4.82 (d, J=10.8 Hz, 1 H) 6.46 (dd, J=3.6, 2.9 Hz, 1 H) 6.85 (dd, J=3.9, 1.4 Hz, 1 H) 7.23-7.30 (m, 2 H) 7.31-7.36 (m, 2 H) 7.36-7.45 (m, 2 H) 7.56-7.65 (m, 2 H) 7.70 (d, J=7.8 Hz, 1 H).

Co. No. 175: (400 MHz, CDCl₃) δ ppm 4.29 (br. s., 1 H) 5.17 (br. s., 1 H) 6.48 (m, J=3.3, 3.3 Hz, 1 H) 6.57 (m, J=2.3 Hz, 1 H) 7.09 (t, J=8.5 Hz, 1 H) 7.20 (d, J=8.0 Hz, 1 H) 7.30-7.39 (m, 2 H) 7.40 (br. s., 1 H) 7.47 (d, J=5.5 Hz, 1 H) 7.75 (dd, J=8.5, 1.5 Hz, 1 H) 7.88 (d, J=8.5 Hz, 1 H) 8.18 (d, J=1.5 Hz, 1 H).

Co. No. 3: (300 MHz, CDCl₃) δ ppm 4.26 (br. s, 1 H), 5.55 (br. s, 1 H), 6.42-6.57 (m, 2 H), 7.28 (dd, J=7.9, 1.5 Hz, 1 H), 7.33 (t, J=7.9 Hz, 1 H), 7.38-7.45 (m, 2 H), 7.82 (d, J=5.1 Hz, 1 H), 8.05 (s, 1 H), 8.75 (d, J=5.0 Hz, 1 H).

Co. No. 194: (400 MHz, CDCl₃) δ ppm 4.26 (br. s., 1 H) 5.63 (br. s., 1 H) 6.51 (m, J=2.8 Hz, 1 H) 6.60 (br. s., 1 H) 7.30-7.37 (m, 2 H) 7.38-7.47 (m, 2 H) 8.00 (d, J=9.3 Hz, 1 H) 8.16 (d, J=9.0 Hz, 1 H) 8.30 (s, 1 H).

Co. No. 65: (400 MHz, CDCl₃) δ ppm 1.41 (t, J=7.5 Hz, 3 H) 3.12 (q, J=7.7 Hz, 2 H) 4.16 (br. s., 1 H) 5.52 (br. s., 1 H) 6.48 (m, J=3.4, 3.4 Hz, 1 H) 6.79 (dd, J=3.6, 1.4 Hz, 1 H) 7.25 (d, J=1.8 Hz, 1 H) 7.29-7.33 (m, 1 H) 7.39 (d, J=1.8 Hz, 1 H) 7.57 (s, 1 H).

Co. No. 173: (300 MHz, CDCl₃) δ ppm 4.54 (br. s., 1 H), 4.87 (br. s., 1 H), 6.46-6.57 (m, 1 H), 6.57-6.67 (m, 1 H), 7.30 (dd, J=8.1, 2.1 Hz, 1 H), 7.36 (d, J=5.5 Hz, 1 H), 7.39-7.52 (m, 4 H), 7.74 (dd, J=8.5, 1.6 Hz, 1 H), 7.90 (d, J=8.5 Hz, 1 H), 8.19 (s, 1 H).

Co. No. 172: (300 MHz, CDCl₃) δ ppm 4.21 (br. s., 1 H), 5.53 (br. s., 1 H), 6.46 (t, J=3.2 Hz, 1 H), 6.54 (dd, J=3.6, 1.5 Hz, 1 H), 7.27-7.32 (m, 2 H), 7.32-7.42 (m, 3 H), 7.51 (d, J=5.4 Hz, 1 H), 7.75 (dd, J=8.3, 1.3 Hz, 1 H), 7.80 (d, J=8.3 Hz, 1 H), 8.24 (s, 1 H).

Co. No. 185: (300 MHz, CDCl₃) δ ppm 4.51 (br. s., 1 H), 4.84 (br. s., 1 H), 6.44-6.51 (m, 1 H), 6.51-6.58 (m, 1 H), 7.28 (dd, J=8.1, 1.9 Hz, 1 H), 7.35-7.47 (m, 3 H), 7.87 (dd, J=8.6, 1.7 Hz, 1 H), 8.11 (d, J=8.6 Hz, 1 H), 8.33 (s, 1 H), 9.06 (s, 1 H).

Co. No. 85: (300 MHz, CDCl$_3$) δ ppm 2.01 (t, J=18.6 Hz, 3 H), 4.25 (br. s, 1 H), 5.51 (br. s, 1 H), 6.55 (dd, J=4.0, 2.8 Hz, 1 H), 6.61 (dd, J=3.9, 1.6 Hz, 1 H), 7.06 (dd, J=8.8, 2.5 Hz, 1 H), 7.20 (dd, J=8.2, 2.5 Hz, 1 H), 7.45 (dd, J=2.8, 1.6 Hz, 1 H), 7.69 (d, J=8.2 Hz, 1 H), 8.19 (dd, J=8.2, 2.2 Hz, 1 H), 8.89 (d, J=2.2 Hz, 1 H).

Co. No. 105: (300 MHz, CDCl$_3$) δ ppm 2.15 (quin, J=7.6 Hz, 2 H), 2.95 (t, J=7.4 Hz, 2 H), 3.04 (t, J=7.7 Hz, 2 H), 4.17 (br. s., 1 H), 5.52 (br. s., 1 H), 6.46 (dd, J=3.8, 2.8 Hz, 1 H), 6.52 (dd, J=3.8, 1.7 Hz, 1 H), 7.25-7.43 (m, 4 H), 7.89 (s, 1 H), 8.57 (s, 1 H).

Co. No. 126: (400 MHz, CDCl$_3$) δ ppm 4.23 (d, J=11.3 Hz, 1 H), 5.65 (d, J=11.5 Hz, 1 H), 6.52 (t, J=3.3 Hz, 1 H), 6.94 (d, J=3.9 Hz, 1 H), 7.19 (t, J=7.8 Hz, 1 H), 7.22-7.29 (m, 2 H), 7.31 (t, J=8.0 Hz, 1 H), 7.34-7.43 (m, 3 H), 7.50 (d, J=7.8 Hz, 1 H).

Co. No. 131: (400 MHz, CDCl$_3$) δ ppm 2.61 (s, 3 H), 2.65 (s, 3 H), 4.19 (d, J=11.5 Hz, 1 H), 5.30 (d, J=11.5 Hz, 1 H), 6.45-6.56 (m, 1 H), 6.93 (br. s, 1 H), 7.10-7.29 (m, 6 H), 7.39 (br. s., 1 H), 7.42 (dd, J=6.9, 2.3 Hz, 1 H).

Co. No. 138: (300 MHz, CDCl$_3$) δ ppm 2.45 (s, 3 H), 4.20 (d, J=11.5 Hz, 1 H), 5.59 (d, J=11.5 Hz, 1 H), 6.47 (t, J=3.4 Hz, 1 H), 6.90 (d, J=3.8 Hz, 1 H), 7.04 (d, J=8.0 Hz, 1 H), 7.11 (s, 1 H), 7.19-7.39 (m, 5 H), 7.43 (d, J=7.9 Hz, 1 H).

Co. No. 174: (400 MHz, CDCl$_3$) δ ppm 4.32 (d, J=11.1 Hz, 1 H), 4.86 (d, J=11.1 Hz, 1 H), 6.42-6.45 (m, 1 H), 6.53 (dd, J=3.8, 1.5 Hz, 1 H), 7.24 (t, J=7.8 Hz, 1 H), 7.36 (d, J=5.1 Hz, 1 H), 7.42-7.53 (m, 3 H), 7.58 (dd, J=2.9, 1.5 Hz, 1 H), 7.82 (dd, J=8.5, 1.7 Hz, 1 H), 7.88 (d, J=8.4 Hz, 1 H), 8.22 (d, J=1.0 Hz, 1 H).

Co. No. 123: (400 MHz, DMSO-d$_6$) δ ppm 4.14 (br. s, 1 H), 5.36 (br. s, 1 H), 6.58 (dd, J=3.8, 2.9 Hz, 1 H), 7.00 (dd, J=3.8, 1.6 Hz, 1 H), 7.27 (td, J=9.2, 2.7 Hz, 1 H), 7.33 (d, J=0.9 Hz, 1 H), 7.45-7.56 (m, 4 H), 7.68 (dd, J=9.0, 4.1 Hz, 1 H), 7.78 (dd, J=2.9, 1.6 Hz, 1 H).

Co. No. 76: (400 MHz, CDCl$_3$) δ ppm 1.31 (t, J=7.6 Hz, 3 H), 2.87 (q, J=7.6 Hz, 2 H), 4.15 (s, 1 H), 5.47 (s, 1 H), 6.48 (dd, J=3.9, 2.8 Hz, 1 H), 6.53 (dd, J=3.8, 1.6 Hz, 1 H), 7.18 (d, J=8.1 Hz, 1 H), 7.31 (d, J=2.0 Hz, 1 H), 7.35 (dd, J=2.9, 1.6 Hz, 1 H), 7.41 (d, J=2.0 Hz, 1 H), 7.95 (dd, J=8.1, 2.3 Hz, 1 H), 8.78 (d, J=2.3 Hz, 1 H).

Co. No. 141: (400 MHz, CDCl$_3$) δ ppm 3.85 (s, 3 H), 4.22 (d, J=11.5 Hz, 1 H), 5.61 (d, J=11.5 Hz, 1 H), 6.50 (t, J=3.3 Hz, 1 H), 6.88 (d, J=8.5, 1.8 Hz, 1 H), 6.93 (d, J=3.4 Hz, 1 H), 7.08-7.16 (m, 2 H), 7.22-7.33 (m, 2 H), 7.35 (s, 1 H), 7.39 (d, J=7.5 Hz, 1 H), 7.45 (d, J=8.6 Hz, 1 H).

Co. No. 119: (400 MHz, CDCl$_3$) δ ppm 4.44 (br. s, 1 H), 4.99 (br. s, 1 H), 6.53 (dd, J=3.7, 3.0 Hz, 1 H), 6.96 (dd, J=3.8, 1.7 Hz, 1 H), 7.21 (s, 1 H), 7.26 (t, J=7.5 Hz, 1 H), 7.29 (dd, J=8.1, 2.1 Hz, 1 H), 7.33-7.42 (m, 3 H), 7.45 (d, J=8.1 Hz, 1 H), 7.60 (t, J=8.6 Hz, 2 H).

Co. No. 121: (400 MHz, CDCl$_3$) δ ppm 4.24 (br. d, J=11.5 Hz, 1 H), 5.64 (br. d, J=11.4 Hz, 1 H), 6.53 (t, J=3.3 Hz, 1 H), 6.93 (br. s, 1 H), 7.15 (br. s., 1 H), 7.22-7.35 (m, 3 H), 7.35-7.44 (m, 2 H), 7.52 (d, J=8.7 Hz, 1 H), 7.57 (s, 1 H).

D. Pharmacological Examples

Example D.1

Measurement of Antifungal Activity in vitro

The standard susceptibility screen is performed in 96-well plates (U-bottom, Greiner Bio-One). Serial dilutions (2-fold or 4-fold) of 20 mM compound stock solutions are made in 100% DMSO, followed by an intermediate dilution step in water. These serial dilutions (10 μl) are then spotted onto test-plates that can be stored in the dark at 4° C. for a maximum period of 2 weeks. An adequate broad dose-range is included with 64 μM as the highest in-test concentration. The culture medium RPMI-1640 is supplemented with L-glutamine, 2% glucose and buffered with 3-(N-morpholino)-propanesulfonic acid (MOPS) at pH 7.0±0.1.

The different fungal species/isolates (Table 3a) are cryopreserved and 1/1000 diluted in medium just prior to use. A standard inoculum of 200 μl containing 10$^3$ colony-forming unit (cfu) is then added to each well. A positive control (100% growth=fungal culture without antifungal) and a negative control (0% growth=RPMI-MOPS medium) are included on each plate. Optimal incubation time and temperature are dependent on the fungal species and vary from 24 h for yeasts (37° C.) to one week or more for dermatophytes (27° C.). Inhibition of fungal growth is measured after adding 10 μl of 0.005% (w/v) resazurin (Sigma Aldrich) to each well, based on the principle that living cells convert the non-fluorescent blue resazurin into the pink and fluorescent resorufin, allowing fluorimetric reading ($\lambda_{ex}$ 550 nm and $\lambda_{em}$ 590 nm) after an additional incubation period ('resa' time mentioned in Table 3a). Results are shown in Table 3b as pIC$_{50}$ values.

TABLE 3a

Incubation conditions for the different fungal species. 'Resa time' represents the additional incubation time after the addition of resazurin to the test system.

| Species | Temperature (° C.) | Time | Resa time |
|---|---|---|---|
| Microsporum canis | 27 | 9 days | 24 hours |
| Trichophyton mentagrophytes | 27 | 7 days | 24 hours |
| Trichophyton rubrum | 27 | 7 days | 24 hours |
| Scedosporium apiospermum | 37 | 48 hours | 17 hours |
| Scedosporium prolificans | 37 | 48 hours | 17 hours |
| Sporothrix schenkii | 27 | 4 days | 24 hours |
| Aspergillus fumigatus | 27 | 48 hours | 17 hours |
| Candida parapsilosis | 37 | 24 hours | 4 hours |
| Cryptococcus neoformans | 37 | 24 hours | 4 hours |
| Rhizopus oryzae | 37 | 24 hours | 6 hours |
| Rhizomucor miehei | 37 | 48 hours | 17 hours |

TABLE 3b

Activities of the test compounds in vitro

| Co. No. | Inf. A | Inf. B | Inf. C | Inf. D | Inf. E | Inf. F | Inf. G | Inf. H | Inf. I | Inf. J | Inf. K |
|---|---|---|---|---|---|---|---|---|---|---|---|
| 1 | 5.52 | 6.35 | 7.17 | 4.34 | 5.70 | <4.19 | 6.69 | <4.19 | 5.74 | <4.19 | <4.19 |
| 2 | 6.19 | 6.48 | 6.78 | <4.19 | 5.70 | 5.70 | 6.37 | 6.28 | 5.79 | <4.19 | <4.19 |
| 3 | <4.19 | 6.90 | 7.37 | <4.19 | 5.87 | <4.19 | 6.64 | 5.67 | 5.52 | <4.19 | <4.19 |
| 5 | 6.18 | 6.50 | 7.16 | <4.19 | 5.57 | 5.45 | 6.97 | 5.22 | 6.51 | <4.19 | 5.10 |
| 7 | 5.56 | 6.76 | 7.19 | 5.01 | 6.52 | 6.12 | 6.61 | 6.29 | 6.67 | <4.19 | 5.15 |
| 8 | 4.85 | 6.37 | 7.41 | 6.10 | 6.31 | 5.37 | 6.75 | 4.99 | 6.36 | <4.80 | 4.35 |

TABLE 3b-continued

Activities of the test compounds in vitro

| Co. No. | Inf. A | Inf. B | Inf. C | Inf. D | Inf. E | Inf. F | Inf. G | Inf. H | Inf. I | Inf. J | Inf. K |
|---|---|---|---|---|---|---|---|---|---|---|---|
| 9 | 5.78 | 6.97 | 7.44 | 6.22 | 7.89 | 6.19 | 7.01 | 6.26 | 7.40 | <4.19 | 5.63 |
| 10 | <4.19 | 4.25 | <4.19 | <4.19 | <4.19 | <4.19 | <4.19 | n.d. | n.d. | n.d. | n.d. |
| 11 | 4.49 | 4.73 | 4.71 | <4.19 | 4.31 | 4.93 | 4.72 | n.d. | n.d. | n.d. | n.d. |
| 12 | 4.59 | <4.49 | 4.92 | <4.49 | <4.49 | 4.82 | <4.49 | n.d. | n.d. | n.d. | n.d. |
| 13 | <4.19 | 5.40 | 5.70 | <4.19 | <4.19 | 4.52 | 5.00 | n.d. | n.d. | n.d. | n.d. |
| 14 | <4.19 | 5.30 | 5.30 | <4.19 | <4.19 | 4.28 | 4.74 | n.d. | n.d. | n.d. | n.d. |
| 15 | <4.19 | 4.25 | 4.70 | <4.19 | <4.19 | 4.92 | 4.56 | n.d. | n.d. | n.d. | n.d. |
| 16 | <4.19 | 5.19 | 5.69 | <4.19 | <4.19 | 4.64 | 5.28 | n.d. | n.d. | n.d. | n.d. |
| 17 | <4.19 | 4.46 | 4.71 | <4.19 | <4.19 | 4.23 | <4.19 | n.d. | n.d. | n.d. | n.d. |
| 18 | <4.19 | 5.05 | 5.52 | <4.19 | <4.19 | <4.19 | 4.62 | n.d. | n.d. | n.d. | n.d. |
| 19 | <4.19 | 4.95 | 5.65 | <4.19 | <4.19 | 5.02 | 4.57 | n.d. | n.d. | n.d. | n.d. |
| 20 | <4.19 | 4.67 | 4.87 | <4.19 | <4.19 | <4.19 | <4.19 | n.d. | n.d. | n.d. | n.d. |
| 21 | 4.70 | 5.04 | 5.52 | <4.19 | <4.19 | 4.66 | n.d. | n.d. | n.d. | n.d. | n.d. |
| 22 | <4.19 | 5.22 | 5.10 | <4.19 | <4.19 | 4.32 | n.d. | n.d. | n.d. | n.d. | n.d. |
| 23 | <4.19 | 4.72 | 5.00 | <4.19 | <4.19 | 4.57 | 4.39 | n.d. | n.d. | n.d. | n.d. |
| 24 | <4.19 | 4.57 | 4.74 | <4.19 | <4.19 | <4.19 | <4.19 | n.d. | n.d. | n.d. | n.d. |
| 25 | <4.19 | 4.43 | 4.19 | <4.19 | <4.19 | <4.19 | <4.19 | n.d. | n.d. | n.d. | n.d. |
| 26 | <4.19 | 4.92 | 5.10 | <4.19 | <4.19 | <4.19 | 4.44 | n.d. | n.d. | n.d. | n.d. |
| 27 | <4.90 | <4.90 | <4.90 | <4.90 | <4.90 | <4.90 | <4.90 | n.d. | n.d. | n.d. | n.d. |
| 28 | <4.19 | 4.29 | 4.43 | <4.19 | <4.19 | <4.19 | 4.28 | n.d. | n.d. | n.d. | n.d. |
| 29 | <4.19 | 5.30 | 5.70 | <4.19 | <4.19 | 4.80 | 5.30 | n.d. | n.d. | n.d. | n.d. |
| 30 | 4.89 | 6.27 | 6.29 | 5.22 | 6.32 | <4.19 | 6.15 | 4.94 | <4.19 | <4.19 | <4.19 |
| 31 | <4.19 | 5.59 | 5.31 | <4.19 | <4.19 | <4.19 | 4.87 | n.d. | n.d. | n.d. | n.d. |
| 32 | 4.35 | 5.70 | 6.10 | <4.19 | <4.19 | 4.39 | 5.70 | n.d. | n.d. | n.d. | n.d. |
| 33 | <4.19 | 5.22 | 4.49 | <4.19 | <4.19 | 4.38 | 4.98 | n.d. | n.d. | n.d. | n.d. |
| 34 | <4.19 | 6.40 | 6.72 | <4.19 | <4.19 | <4.19 | 6.22 | <4.19 | 5.66 | <4.19 | <4.19 |
| 35 | <4.19 | 5.70 | 6.07 | <4.19 | <4.19 | <4.19 | 5.70 | n.d. | n.d. | n.d. | n.d. |
| 36 | <4.19 | 5.19 | 5.10 | <4.19 | <4.19 | <4.19 | 5.21 | n.d. | n.d. | n.d. | n.d. |
| 37 | <4.19 | 4.38 | 5.31 | <4.19 | <4.19 | 5.39 | 4.41 | n.d. | n.d. | n.d. | n.d. |
| 38 | 4.40 | 5.15 | 5.22 | <4.19 | 4.41 | <4.19 | 5.22 | n.d. | n.d. | n.d. | n.d. |
| 39 | 5.52 | 5.52 | 5.15 | <4.19 | 5.52 | <4.19 | 5.15 | n.d. | n.d. | n.d. | n.d. |
| 40 | <4.19 | 5.52 | 4.77 | <4.19 | <4.19 | <4.19 | 4.47 | n.d. | n.d. | n.d. | n.d. |
| 41 | <4.19 | <4.19 | 4.80 | <4.19 | <4.19 | <4.19 | <4.19 | n.d. | n.d. | n.d. | n.d. |
| 42 | <4.19 | 4.19 | 5.06 | <4.19 | <4.19 | 4.89 | 4.49 | n.d. | n.d. | n.d. | n.d. |
| 43 | <4.19 | 4.52 | 4.30 | <4.19 | <4.19 | <4.19 | <4.19 | n.d. | n.d. | n.d. | n.d. |
| 44 | <4.19 | 5.31 | 5.20 | <4.19 | <4.19 | <4.19 | 4.77 | n.d. | n.d. | n.d. | n.d. |
| 45 | 4.80 | 5.32 | 5.09 | <4.19 | <4.19 | 4.62 | <4.19 | n.d. | n.d. | n.d. | n.d. |
| 46 | <4.19 | 5.12 | <4.19 | <4.19 | <4.19 | <4.19 | <4.19 | n.d. | n.d. | n.d. | n.d. |
| 47 | <4.19 | 5.84 | 6.25 | <4.19 | 4.91 | <4.19 | 5.08 | 6.03 | 6.38 | <4.19 | 4.81 |
| 48 | <4.19 | 4.30 | 5.39 | <4.19 | <4.19 | 4.84 | <4.19 | n.d. | n.d. | n.d. | n.d. |
| 49 | <4.80 | 4.82 | 5.28 | <4.19 | <4.19 | <4.19 | <4.19 | n.d. | n.d. | n.d. | n.d. |
| 50 | <4.19 | 4.56 | 4.49 | <4.19 | <4.19 | <4.19 | <4.19 | n.d. | n.d. | n.d. | n.d. |
| 51 | <4.19 | 5.40 | 5.63 | <4.19 | <4.19 | 4.45 | 4.94 | n.d. | n.d. | n.d. | n.d. |
| 52 | 5.40 | 5.70 | 6.13 | <4.19 | 5.30 | 6.00 | 5.70 | n.d. | n.d. | n.d. | n.d. |
| 53 | 4.92 | 5.70 | 6.10 | <4.19 | 5.40 | 5.70 | 5.70 | n.d. | n.d. | n.d. | n.d. |
| 54 | n.d. | n.d. | n.d. | n.d. | n.d. | n.d. | n.d. | n.d. | n.d. | n.d. | n.d. |
| 55 | 5.04 | 5.70 | 6.30 | <4.19 | 5.55 | 5.32 | 5.72 | 4.86 | 5.47 | <4.19 | <4.19 |
| 56 | <4.19 | <4.19 | 5.71 | <4.19 | <4.19 | <4.19 | 4.48 | n.d. | n.d. | n.d. | n.d. |
| 57 | <4.19 | 5.24 | 5.10 | <4.19 | <4.19 | <4.19 | <4.19 | n.d. | n.d. | n.d. | n.d. |
| 58 | <4.19 | 5.08 | 6.29 | <4.19 | 4.48 | 4.58 | 5.09 | n.d. | n.d. | n.d. | n.d. |
| 59 | 4.85 | 6.22 | 6.47 | <4.19 | <4.19 | <4.19 | 6.00 | n.d. | n.d. | n.d. | n.d. |
| 60 | <4.19 | 5.18 | 5.70 | <4.19 | 4.30 | <4.19 | 4.47 | n.d. | n.d. | n.d. | n.d. |
| 61 | <4.19 | 4.66 | 4.52 | <4.19 | <4.19 | 4.44 | 4.39 | n.d. | n.d. | n.d. | n.d. |
| 62 | 4.51 | 4.59 | 5.22 | 4.23 | 4.70 | 5.15 | 4.86 | n.d. | n.d. | n.d. | n.d. |
| 63 | <4.19 | <4.19 | 5.72 | <4.19 | <4.19 | <4.19 | 5.58 | n.d. | n.d. | n.d. | n.d. |
| 64 | <4.19 | 5.42 | 5.46 | <4.19 | <4.19 | 4.70 | 5.94 | n.d. | n.d. | n.d. | n.d. |
| 65 | 4.56 | 4.72 | 5.19 | <4.19 | <4.19 | 5.06 | 5.48 | n.d. | n.d. | n.d. | n.d. |
| 66 | <4.19 | 4.98 | 6.18 | <4.19 | <4.19 | <4.19 | 4.19 | n.d. | n.d. | n.d. | n.d. |
| 67 | <4.19 | 4.50 | 4.71 | <4.19 | <4.19 | <4.19 | <4.19 | n.d. | n.d. | n.d. | n.d. |
| 68 | <4.19 | 4.91 | 5.58 | <4.19 | <4.19 | 4.38 | 4.80 | n.d. | n.d. | n.d. | n.d. |
| 69 | <4.19 | 4.71 | 5.09 | <4.19 | <4.19 | <4.19 | <4.19 | n.d. | n.d. | n.d. | n.d. |
| 70 | 5.17 | 6.36 | 6.99 | 5.12 | 6.00 | 5.28 | 6.40 | 5.68 | 6.38 | 5.50 | 4.52 |
| 71 | 5.42 | 5.83 | 5.55 | <4.19 | <4.19 | 5.00 | 5.78 | n.d. | n.d. | n.d. | n.d. |
| 72 | <4.49 | 5.61 | 6.05 | <4.49 | <4.49 | <4.49 | <4.49 | n.d. | n.d. | n.d. | n.d. |
| 73 | <4.49 | 5.10 | 6.09 | <4.49 | <4.49 | <4.49 | <4.49 | n.d. | n.d. | n.d. | n.d. |
| 74 | 4.44 | 5.91 | 6.31 | 4.92 | 5.25 | <4.19 | 6.18 | 6.29 | 6.88 | <4.19 | <4.19 |
| 75 | <4.19 | 6.45 | <4.19 | <4.19 | <4.19 | <4.19 | <4.19 | n.d. | n.d. | n.d. | n.d. |
| 76 | 4.46 | 6.34 | 5.75 | <4.19 | 4.72 | 4.82 | 5.00 | 5.07 | 5.46 | <4.19 | 4.49 |
| 77 | 4.52 | 5.67 | 6.22 | 4.69 | 6.05 | 5.03 | 5.71 | 4.88 | 5.57 | <4.19 | <4.19 |
| 78 | <4.19 | 5.41 | 6.18 | 5.07 | 5.42 | <4.19 | 4.47 | n.d. | n.d. | n.d. | n.d. |
| 79 | <4.19 | 5.72 | 6.33 | 4.69 | 6.63 | <4.19 | 5.76 | 6.12 | 6.28 | <4.19 | <4.19 |
| 80 | 5.42 | 5.09 | 5.79 | <4.19 | 5.59 | <4.19 | 5.23 | n.d. | n.d. | n.d. | n.d. |
| 81 | 5.65 | <4.19 | <4.19 | 4.19 | 5.58 | <4.19 | <4.19 | n.d. | n.d. | n.d. | n.d. |
| 82 | <4.19 | 6.37 | 6.85 | 5.285 | 6.28 | <4.19 | 6.24 | 6.01 | 6.24 | <4.19 | <4.19 |
| 83 | <4.19 | 4.97 | 6.68 | <4.19 | 5.33 | <4.19 | 5.88 | <4.19 | 6.09 | <4.19 | <4.19 |
| 84 | 5.65 | 6.24 | 6.26 | 5.44 | 6.24 | 5.88 | 5.88 | 5.31 | <4.19 | <4.19 | <4.19 |

TABLE 3b-continued

Activities of the test compounds in vitro

| Co. No. | Inf. A | Inf. B | Inf. C | Inf. D | Inf. E | Inf. F | Inf. G | Inf. H | Inf. I | Inf. J | Inf. K |
|---|---|---|---|---|---|---|---|---|---|---|---|
| 85 | 4.63 | 6.73 | 6.81 | 5.61 | 6.28 | 5.86 | 6.60 | 5.44 | 4.81 | <4.19 | <4.19 |
| 86 | 4.94 | 5.67 | 6.30 | 5.56 | 5.68 | 4.99 | 5.59 | 4.43 | 5.77 | <4.19 | <4.19 |
| 87 | <4.19 | 5.97 | 6.54 | <4.19 | 4.94 | <4.19 | 5.18 | <4.19 | 5.71 | <4.19 | <4.19 |
| 88 | 4.85 | 6.63 | 7.10 | <4.19 | <4.19 | <4.19 | 5.80 | 5.28 | 6.14 | <4.19 | <4.19 |
| 89 | <4.19 | 6.14 | 6.75 | 6.17 | 5.70 | <4.19 | 6.23 | <4.19 | 6.28 | <4.19 | <4.19 |
| 90 | <4.19 | 5.42 | 6.19 | <4.19 | <4.19 | <4.19 | 5.33 | n.d. | n.d. | n.d. | n.d. |
| 91 | 5.10 | 5.69 | 6.27 | <4.19 | 5.75 | <4.19 | 5.72 | <4.19 | 5.28 | <4.19 | <4.19 |
| 92 | <4.19 | <4.19 | 6.09 | <4.19 | <4.19 | <4.19 | <4.19 | <4.19 | <4.19 | <4.19 | <4.19 |
| 93 | <4.19 | 5.26 | 6.16 | <4.19 | 5.02 | <4.19 | 5.63 | n.d. | n.d. | n.d. | n.d. |
| 94 | <4.19 | 5.71 | 6.19 | 4.59 | 5.13 | 4.58 | 5.92 | <4.19 | <4.19 | <4.19 | <4.19 |
| 95 | <4.49 | <4.49 | 5.17 | <4.49 | <4.49 | <4.49 | 4.58 | n.d. | n.d. | n.d. | n.d. |
| 96 | <4.19 | 4.80 | 5.10 | <4.19 | 4.40 | <4.19 | 5.00 | n.d. | n.d. | n.d. | n.d. |
| 97 | <4.49 | 4.87 | 5.99 | <4.49 | <4.49 | <4.49 | 4.83 | n.d. | n.d. | n.d. | n.d. |
| 98 | 4.49 | <4.19 | 4.47 | 5.06 | 4.49 | 5.03 | 4.48 | n.d. | n.d. | n.d. | n.d. |
| 99 | <4.19 | 5.10 | 4.89 | <4.19 | <4.19 | <4.19 | <4.19 | n.d. | n.d. | n.d. | n.d. |
| 100 | <4.19 | 4.21 | <4.19 | <4.19 | <4.19 | <4.19 | <4.19 | n.d. | n.d. | n.d. | n.d. |
| 101 | <4.19 | 4.56 | 5.23 | <4.19 | <4.19 | <4.19 | 5.57 | n.d. | n.d. | n.d. | n.d. |
| 102 | 4.59 | 6.34 | 6.84 | <4.19 | 5.05 | <4.19 | 6.01 | <4.19 | 5.18 | <4.19 | <4.19 |
| 103 | <4.19 | <4.19 | 4.49 | <4.19 | <4.19 | <4.19 | <4.19 | n.d. | n.d. | n.d. | n.d. |
| 104 | <4.19 | <4.19 | 5.91 | <4.19 | 5.54 | <4.19 | <4.19 | n.d. | n.d. | n.d. | n.d. |
| 105 | 5.70 | 6.67 | 6.87 | 4.91 | 5.76 | 5.30 | 6.91 | 7.52 | 8.00 | <4.19 | 4.23 |
| 106 | 4.90 | 5.79 | 6.18 | 5.09 | 5.05 | 5.26 | 5.51 | n.d. | n.d. | n.d. | n.d. |
| 107 | 5.16 | 6.31 | 5.92 | 4.87 | 5.06 | 5.53 | 5.44 | 4.90 | 5.48 | <4.19 | <4.19 |
| 108 | <4.49 | 4.98 | 5.99 | <4.49 | <4.49 | <4.49 | 5.43 | n.d. | n.d. | n.d. | n.d. |
| 109 | <4.19 | <4.19 | 5.70 | <4.19 | <4.19 | 4.34 | 4.37 | n.d. | n.d. | n.d. | n.d. |
| 110 | 4.44 | 5.30 | 5.96 | 4.58 | 5.50 | 5.09 | 5.60 | 4.77 | 5.89 | <4.49 | <4.49 |
| 111 | 4.41 | 5.69 | 6.09 | <4.19 | 5.76 | 5.74 | 5.31 | 5.77 | 6.77 | <4.19 | 4.53 |
| 112 | <4.19 | 5.18 | 6.02 | <4.19 | <4.19 | 5.07 | <4.19 | n.d. | n.d. | n.d. | n.d. |
| 113 | <4.19 | <4.19 | 5.86 | <4.19 | <4.19 | <4.19 | <4.19 | n.d. | n.d. | n.d. | n.d. |
| 114 | <4.19 | <4.19 | 5.75 | <4.19 | <4.19 | <4.19 | <4.19 | n.d. | n.d. | n.d. | n.d. |
| 115 | 5.70 | 7.02 | 7.47 | 4.25 | 6.82 | 5.70 | 7.28 | <4.19 | 5.98 | <4.19 | 4.88 |
| 116 | 5.84 | 7.39 | 7.52 | 4.70 | 6.26 | 5.65 | 6.83 | 6.22 | 6.46 | <4.19 | 4.81 |
| 117 | 5.74 | 6.52 | 7.07 | <4.19 | 5.98 | 5.77 | 6.43 | 4.80 | 5.97 | <4.19 | 4.80 |
| 118 | 5.70 | 7.39 | 7.01 | 5.70 | 7.38 | 5.30 | 7.07 | <4.19 | n.d. | <4.19 | <4.19 |
| 119 | 6.00 | 6.54 | 6.87 | 5.61 | 6.30 | 6.40 | 6.62 | <4.19 | 6.17 | <4.19 | <4.19 |
| 120 | 4.86 | 6.16 | 6.31 | <4.19 | 5.99 | 5.52 | 5.81 | 4.19 | 5.52 | <4.19 | <4.19 |
| 121 | 6.11 | 6.96 | 6.82 | <4.19 | 5.52 | <4.19 | 6.86 | 5.97 | 6.15 | 5.77 | 5.58 |
| 122 | 5.42 | 6.90 | 6.86 | <4.19 | 5.38 | 4.69 | 5.55 | <4.19 | 4.62 | <4.19 | <4.19 |
| 123 | 5.04 | 6.75 | 6.96 | <4.19 | 6.25 | 4.98 | 6.23 | 6.02 | 6.44 | <4.19 | 5.14 |
| 124 | 5.10 | 5.63 | 6.22 | <4.19 | 6.25 | 6.32 | 5.75 | <4.19 | 5.90 | 5.08 | <4.19 |
| 125 | 4.91 | 5.85 | 5.72 | <4.19 | 5.70 | 5.69 | 5.55 | 5.31 | 6.05 | <4.19 | <4.19 |
| 126 | <4.19 | 6.33 | 6.87 | <4.19 | 6.29 | 5.18 | 6.34 | 5.45 | 6.64 | <4.19 | <4.19 |
| 127 | <4.19 | 6.44 | 6.94 | <4.19 | 6.31 | 5.22 | 6.40 | 4.80 | 6.64 | <4.19 | <4.19 |
| 128 | <4.19 | 6.02 | 6.87 | <4.19 | 5.99 | 4.69 | 6.30 | <4.19 | 7.10 | <4.19 | <4.19 |
| 129 | <4.19 | <4.19 | 4.96 | <4.19 | 5.61 | <4.19 | <4.19 | n.d. | n.d. | n.d. | n.d. |
| 130 | 5.50 | 6.70 | 7.69 | 5.35 | 6.00 | 6.31 | 6.79 | 6.01 | 5.08 | 4.95 | 4.91 |
| 131 | 5.51 | 6.50 | 7.10 | 4.81 | 6.11 | 6.11 | 6.31 | 5.355 | 5.99 | <4.34 | 4.59 |
| 132 | <4.49 | 4.59 | 5.54 | <4.49 | <4.49 | <4.49 | <4.49 | n.d. | n.d. | n.d. | n.d. |
| 133 | <4.19 | <4.19 | <4.19 | <4.19 | <4.19 | 5.83 | <4.19 | n.d. | n.d. | n.d. | n.d. |
| 134 | 4.50 | 6.68 | 7.16 | 4.54 | 5.66 | <4.19 | 6.66 | <4.19 | 6.48 | <4.19 | <4.19 |
| 135 | <4.19 | 4.41 | 5.91 | <4.19 | <4.19 | 4.54 | <4.19 | n.d. | n.d. | n.d. | n.d. |
| 136 | <4.19 | 4.41 | 5.67 | <4.19 | <4.19 | <4.19 | <4.19 | n.d. | n.d. | n.d. | n.d. |
| 137 | 5.52 | 6.81 | 7.18 | 4.74 | 6.00 | 5.10 | 6.89 | 5.16 | 6.21 | 4.48 | 4.50 |
| 138 | <4.19 | 6.99 | 6.83 | <4.19 | <4.19 | <4.19 | 6.83 | 5.78 | 6.32 | <4.19 | <4.19 |
| 139 | <4.19 | 4.46 | 4.40 | <4.19 | <4.19 | <4.19 | <4.19 | n.d. | n.d. | n.d. | n.d. |
| 140 | 6.23 | 6.44 | 7.50 | 4.34 | 5.05 | 4.60 | 6.11 | 5.35 | 6.36 | <4.19 | 4.68 |
| 141 | <4.19 | 6.88 | 6.86 | <4.19 | <4.19 | <4.19 | 7.64 | <4.19 | 5.05 | <4.19 | <4.19 |
| 142 | <4.19 | <4.19 | 5.64 | <4.19 | <4.19 | <4.19 | <4.19 | n.d. | n.d. | n.d. | n.d. |
| 143 | 5.49 | <4.19 | 6.11 | <4.19 | <4.19 | <4.19 | 5.20 | n.d. | n.d. | n.d. | n.d. |
| 144 | 5.69 | 6.49 | >8.41 | 4.57 | 5.62 | 5.31 | 7.45 | 4.71 | 6.26 | <4.19 | 4.44 |
| 145 | <4.19 | 4.81 | 5.11 | <4.19 | <4.19 | <4.19 | <4.19 | n.d. | n.d. | n.d. | n.d. |
| 146 | <4.19 | 5.76 | 6.19 | <4.19 | <4.19 | <4.19 | 5.44 | <4.19 | 4.80 | <4.19 | <4.19 |
| 147 | <4.19 | 5.66 | 5.35 | <4.19 | <4.19 | <4.19 | <4.19 | n.d. | n.d. | n.d. | n.d. |
| 148 | <4.19 | 5.82 | 5.04 | <4.19 | <4.19 | <4.19 | 4.19 | n.d. | n.d. | n.d. | n.d. |
| 149 | <4.19 | 5.35 | 6.10 | <4.19 | 5.47 | 4.81 | 5.61 | <4.19 | 5.79 | <4.19 | <4.19 |
| 150 | 5.52 | 6.14 | 8.25 | 4.68 | 6.00 | 4.57 | 6.15 | <4.19 | 5.93 | <4.19 | <4.19 |
| 151 | <4.19 | <4.19 | 4.95 | <4.19 | <4.19 | <4.19 | <4.19 | n.d. | n.d. | n.d. | n.d. |
| 152 | 5.11 | 6.34 | 6.85 | 5.59 | 6.26 | 5.82 | 6.46 | 4.28 | 5.15 | <4.19 | <4.19 |
| 153 | <4.19 | <4.19 | <4.19 | 5.00 | <4.19 | 5.16 | <4.19 | n.d. | n.d. | n.d. | n.d. |
| 154 | <4.19 | <4.19 | <4.19 | <4.19 | <4.19 | <4.19 | <4.19 | n.d. | n.d. | n.d. | n.d. |
| 155 | 5.66 | 6.82 | 7.15 | 4.94 | 5.88 | 5.81 | 6.82 | n.d. | n.d. | n.d. | n.d. |
| 156 | <4.19 | <4.19 | <4.19 | <4.19 | 4.48 | 4.51 | 4.49 | n.d. | n.d. | n.d. | n.d. |
| 157 | <4.49 | 5.79 | 6.58 | 4.61 | <4.49 | <4.49 | 5.96 | n.d. | n.d. | n.d. | n.d. |
| 158 | <4.19 | 5.70 | 5.72 | <4.19 | <4.19 | 5.20 | 5.17 | 4.37 | 6.00 | <4.19 | <4.19 |
| 159 | <4.49 | 6.41 | 6.46 | <4.49 | <4.49 | <4.49 | <4.49 | n.d. | n.d. | n.d. | n.d. |
| 160 | <4.49 | 5.03 | 5.84 | <4.49 | 5.85 | 5.61 | 5.48 | n.d. | n.d. | n.d. | n.d. |

TABLE 3b-continued

Activities of the test compounds in vitro

| Co. No. | Inf. A | Inf. B | Inf. C | Inf. D | Inf. E | Inf. F | Inf. G | Inf. H | Inf. I | Inf. J | Inf. K |
|---|---|---|---|---|---|---|---|---|---|---|---|
| 161 | 5.02 | 5.96 | 6.12 | <4.19 | 5.04 | 4.56 | 5.40 | 6.47 | 6.27 | <4.19 | <4.19 |
| 162 | 4.22 | 5.23 | 5.61 | <4.19 | 4.36 | 4.49 | 5.21 | n.d. | n.d. | n.d. | n.d. |
| 163 | 5.59 | 6.14 | 6.71 | 5.12 | 5.61 | 6.51 | 5.99 | 5.63 | 6.27 | 4.98 | 5.06 |
| 164 | 5.40 | 5.86 | 6.51 | 4.97 | 5.70 | 5.85 | 6.29 | 5.66 | 6.44 | <4.19 | 5.15 |
| 165 | 5.12 | 6.19 | 6.70 | <4.19 | 5.28 | 5.81 | 5.86 | <4.19 | 4.46 | <4.19 | <4.19 |
| 166 | 5.52 | 5.70 | 5.70 | <4.19 | 6.00 | 6.00 | 5.52 | 4.33 | 5.65 | 5.37 | <4.19 |
| 167 | 5.70 | 6.01 | 6.79 | 4.90 | 5.38 | 5.86 | 5.97 | 5.72 | 6.31 | <4.19 | 5.10 |
| 168 | 6.22 | 4.96 | 6.18 | <4.19 | 6.73 | 6.41 | 6.40 | <4.19 | 6.48 | <4.19 | <4.19 |
| 169 | <4.19 | 5.00 | 6.01 | <4.19 | <4.19 | <4.19 | <4.19 | n.d. | n.d. | n.d. | n.d. |
| 170 | 5.55 | 6.23 | 6.63 | <4.19 | 5.74 | 6.47 | 6.18 | 5.63 | 6.51 | <4.19 | <4.19 |
| 171 | <4.19 | <4.19 | 5.73 | <4.19 | <4.19 | 6.50 | <4.19 | n.d. | n.d. | n.d. | n.d. |
| 172 | 5.59 | 6.90 | 7.35 | 5.80 | 6.29 | 5.85 | 6.81 | 5.15 | 5.45 | <4.19 | 4.72 |
| 173 | 5.70 | 6.54 | 6.41 | 5.71 | 6.30 | 6.41 | 6.51 | 5.08 | 4.54 | <4.19 | 5.08 |
| 174 | 6.06 | 6.54 | 6.87 | <4.19 | 6.30 | 6.43 | 6.80 | <4.19 | 4.80 | <4.19 | <4.19 |
| 175 | 5.70 | 6.90 | 7.36 | 6.17 | 6.85 | 6.41 | 7.11 | 5.08 | 5.56 | 5.07 | 5.14 |
| 176 | 5.70 | 6.89 | 6.90 | 6.03 | 6.49 | 6.49 | 6.57 | 5.54 | 6.15 | <4.19 | <4.19 |
| 177 | <4.19 | <4.19 | <4.19 | <4.19 | <4.19 | 5.73 | <4.19 | n.d. | n.d. | n.d. | n.d. |
| 178 | <4.19 | <4.19 | 4.37 | <4.19 | 5.93 | 6.49 | 4.26 | n.d. | n.d. | n.d. | n.d. |
| 179 | 4.41 | 4.80 | 5.03 | <4.19 | 4.49 | 4.67 | 4.69 | n.d. | n.d. | n.d. | n.d. |
| 180 | <4.19 | 4.40 | 6.03 | <4.19 | <4.19 | <4.19 | 4.39 | n.d. | n.d. | n.d. | n.d. |
| 181 | <4.19 | 5.69 | 5.94 | <4.19 | <4.19 | <4.19 | 4.98 | n.d. | n.d. | n.d. | n.d. |
| 182 | <4.49 | 5.52 | 6.70 | 4.58 | 4.94 | 4.91 | 5.87 | n.d. | n.d. | n.d. | n.d. |
| 183 | 4.77 | 5.85 | 6.68 | 5.31 | 5.26 | 4.49 | 5.99 | <4.49 | 4.96 | <4.49 | <4.49 |
| 184 | <4.19 | 6.70 | 7.32 | <4.19 | 6.27 | <4.19 | 6.51 | <4.19 | 6.15 | <4.19 | <4.19 |
| 185 | 5.28 | 6.39 | 6.73 | 4.23 | 6.29 | 6.33 | 6.04 | 4.41 | 5.16 | <4.19 | <4.19 |
| 186 | 5.15 | 5.95 | 6.34 | <4.19 | 5.63 | 5.69 | 6.06 | 4.78 | 5.40 | <4.19 | 4.35 |
| 187 | 5.09 | 5.68 | 6.77 | 4.50 | 5.98 | 5.46 | 6.22 | 5.79 | 6.92 | <4.19 | <4.19 |
| 188 | <4.19 | 6.20 | 6.64 | 4.90 | 5.56 | 4.98 | 6.05 | 6.29 | 6.24 | <4.19 | 4.42 |
| 189 | <4.19 | 5.29 | 6.05 | <4.19 | 5.02 | 5.06 | 5.52 | n.d. | n.d. | n.d. | n.d. |
| 190 | <4.19 | 5.56 | 6.14 | <4.19 | <4.19 | 4.93 | 5.31 | n.d. | n.d. | n.d. | n.d. |
| 191 | 4.75 | 5.69 | 6.18 | <4.19 | 5.42 | 5.00 | 5.80 | 4.88 | 6.35 | <4.19 | <4.19 |
| 192 | <4.19 | <4.19 | 4.29 | <4.19 | <4.19 | 4.81 | 5.03 | n.d. | n.d. | n.d. | n.d. |
| 193 | <4.19 | <4.19 | <4.19 | <4.19 | <4.19 | <4.19 | <4.19 | n.d. | n.d. | n.d. | n.d. |
| 194 | <4.19 | <4.19 | 6.82 | <4.19 | <4.19 | <4.19 | 6.06 | n.d. | n.d. | n.d. | n.d. |
| 195 | <4.19 | <4.19 | 6.34 | <4.19 | <4.19 | <4.19 | <4.19 | n.d. | n.d. | n.d. | n.d. |
| 196 | 5.00 | 6.36 | 6.77 | 5.25 | 5.65 | 5.84 | 6.17 | 4.35 | 5.72 | <4.19 | <4.19 |
| 197 | 5.00 | 6.00 | 6.00 | 4.00 | <4 | 5.00 | 5.33 | <4 | 5.00 | n.d. | n.d. |
| 198 | <4 | 4.00 | <4 | <4 | <4 | 5.00 | <4 | <4 | <4 | n.d. | n.d. |
| 199 | <4 | 4.50 | 5.00 | <4 | <4 | 5.00 | <4 | <4 | <4 | n.d. | n.d. |
| 201 | <4 | 6.00 | 6.00 | <4 | <4 | <4 | <4 | <4 | 7.00 | n.d. | n.d. |
| 202 | 6.00 | 8.00 | 7.00 | <4 | 5.67 | 5.00 | 6.33 | 5.00 | 7.00 | n.d. | n.d. |
| 203 | <4 | 4.50 | 4.67 | <4 | <4 | <4 | <4 | <4 | <4 | n.d. | n.d. |
| 204 | <4 | 4.50 | 4.67 | <4 | <4 | <4 | <4 | <4 | <4 | n.d. | n.d. |
| 205 | <4 | n.d. | <4 | <4 | <4 | <4 | <4 | n.d. | n.d. | n.d. | n.d. |
| 206 | 5.33 | 5.00 | 6.00 | <4 | 5.33 | 5.33 | 5.33 | 5.00 | 6.00 | n.d. | n.d. |

('n.d.' means not determined; 'Inf.' means infection; values are pIC$_{50}$ values)
Inf. 'A': *Sporothrix schenkii* B62482
Inf. 'B': *Microsporum canis* B68128
Inf. 'C': *Trichophyton rubrum* B68183
Inf. 'D': *Candida parapsilosis* B66126
Inf. 'E': *Aspergillus fumigatus* B42928
Inf. 'F': *Cryptococcus neoformans* B66663
Inf. 'G': *Trichophyton mentagrophytes* B70554
Inf. 'H': *Scedosporium apiospermum* IHEM3817
Inf. 'I': *Scedosporium prolificans* IHEM21157
Inf. 'J': *Rhizopus oryzae* IHEM5223
Inf. 'K': *Rhizomucor miehei* IHEM13391
n.d. means not determined E. Composition Example "Active ingredient" as used throughout these examples, relates to a compound of Formula (I), including any stereochemically isomeric form thereof, a pharmaceutically acceptable salt thereof or a solvate thereof; in particular to any one of the exemplified compounds.

Example E1

Injectable Solution 1.8 Grams methyl 4-hydroxybenzoate and 0.2 grams sodium hydroxide are dissolved in about 0.5 l of boiling water for injection. After cooling to about 50° C. there are added while stirring 0.05 grams propylene glycol and 4 grams of the active ingredient. The solution is cooled to room temperature and supplemented with water for injection q.s. ad 1 l, giving a solution comprising 4 mg/ml of active ingredient. The solution is sterilized by filtration and filled in sterile containers.

Example E2

Transungual Composition 0.144 g KH$_2$PO$_4$, 9 g NaCl, 0.528 g Na$_2$HPO$_4$.2H$_2$O is added to 800 ml H$_2$O and the mixture is stirred. The pH is adjusted to 7.4 with NaOH and 500 mg NaN₃ is added. Ethanol (42 v/v %) is added and the pH is adjusted to 2.3 with HCl.

15 mg active ingredient is added to 2.25 ml PBS (Phosphate Buffer Saline)/Ethanol (42%; pH 2.3) and the mixture is stirred and treated with ultrasound. 0.25 ml PBS/Ethanol (42%; pH 2.3) is added and the mixture is further stirred and treated with ultrasound until all active ingredient is dissolved, yielding the desired transungual composition.

Example E3

Oral Drops

500 Grams of the A.I. is dissolved in 0.5 l of a sodium hydroxide solution and 1.5 l of the polyethylene glycol at 60~80° C. After cooling to 30~40° C. there are added 35 l of polyethylene glycol and the mixture is stirred well. Then there is added a solution of 1750 grams of sodium saccharin in 2.5 l of purified water and while stirring there are added 2.5 l of cocoa flavor and polyethylene glycol q.s. to a volume of 50 l, providing an oral drop solution comprising 10 mg/ml of A.I. The resulting solution is filled into suitable containers.

Example E4

Capsules

20 Grams of the A.I., 6 grams sodium lauryl sulfate, 56 grams starch, 56 grams lactose, 0.8 grams colloidal silicon dioxide, and 1.2 grams magnesium stearate are vigorously stirred together. The resulting mixture is subsequently filled into 1000 suitable hardened gelatin capsules, comprising each 20 mg of the active ingredient.

Example E5

Film-coated Tablets

Preparation of Tablet Core

A mixture of 100 grams of the A.I., 570 grams lactose and 200 grams starch is mixed well and thereafter humidified with a solution of 5 grams sodium dodecyl sulfate and 10 grams polyvinylpyrrolidone in about 200 ml of water. The wet powder mixture is sieved, dried and sieved again. Then there is added 100 grams microcrystalline cellulose and 15 grams hydrogenated vegetable oil. The whole is mixed well and compressed into tablets, giving 10.000 tablets, each containing 10 mg of the active ingredient.

Coating

To a solution of 10 grams methyl cellulose in 75 ml of denaturated ethanol there is added a solution of 5 grams of ethyl cellulose in 150 ml of dichloromethane. Then there are added 75 ml of dichloromethane and 2.5 ml 1,2,3-propanetriol. 10 Grams of polyethylene glycol is molten and dissolved in 75 ml of dichloromethane. The latter solution is added to the former and then there are added 2.5 grams of magnesium octadecanoate, 5 grams of polyvinylpyrrolidone and 30 ml of concentrated colour suspension and the whole is homogenated. The tablet cores are coated with the thus obtained mixture in a coating apparatus.

Example E6

2% Cream

Stearyl alcohol (75 mg), cetyl alcohol (20 mg), sorbitan monostearate (20 mg) and isopropyl myristate (10 mg) are introduced in a doublewall jacketed vessel and heated until the mixture has completely molten. This mixture is added to a separately prepared mixture of purified water, propylene glycol (200 mg) and polysorbate 60 (15 mg) having a temperature of 70 to 75° C. while using a homogenizer for liquids. The resulting mixture is allowed to cool to below 25° C. while continuously mixing. A solution of A.I. (20 mg), polysorbate 80 (1 mg) and purified water q.s. ad 1 g and a solution of sodium sulfite anhydrous (2 mg) in purified water are next added to the emulsion while continuously mixing. The cream is homogenized and filled into suitable tubes.

Example E7

2% Cream

A mixture of A.I. (2 g), phosphatidyl choline (20 g), cholesterol (5 g) and ethyl alcohol (10 g) is stirred and heated at 55-60° C. until complete solution and is added to a solution of methyl paraben(0.2 g), propyl paraben (0.02 g), disodium edetate (0.15 g) and sodium chloride (0.3 g) in purified water (ad 100 g) while homogenizing. Hydroxypropylmethylcellulose (1.5 g) in purified water is added and the mixing is continued until swelling is complete.

The invention claimed is:

1. A compound of formula (I)

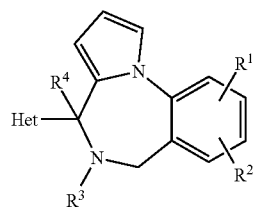

(I)

or a stereoisomeric form thereof, wherein, $R^1$ is hydrogen, halo, $C_{1-4}$alkyl or $C_{1-4}$alkyloxy;
$R^2$ is hydrogen, halo, $C_{1-4}$alkyl or $C_{1-4}$alkyloxy;
$R^3$ and $R^4$ are hydrogen;
or $R^3$ and $R^4$ taken together form a bond;
Het is a monocyclic or bicyclic heterocyclic radical selected from

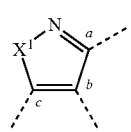

(d-1)

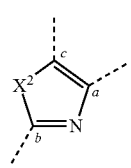

(d-2)

(d-3)

-continued

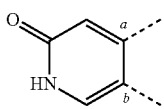 (d-4)

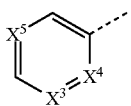 (d-5)

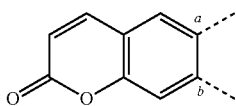 (d-6)

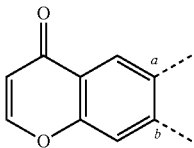 (d-7)

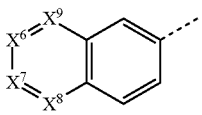 (d-8)

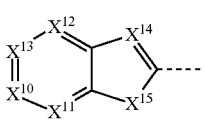 (d-9)

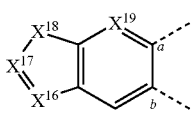 (d-10)

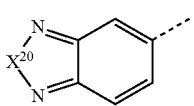 (d-11)

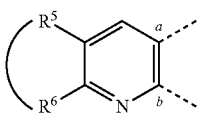 (d-12)

(d-1) and (d-2) are attached to the remainder of the molecule with a bond in position a, b or c;
(d-4), (d-6), (d-7), (d-10) and (d-12) are attached to the remainder of the molecule with a bond in position a or b;
$X^1$ is O, S or NH;
$X^2$ is O or S;
$X^3$, $X^4$ and $X^5$ each independently are CH or N; provided that exactly two of $X^3$, $X^4$ and $X^5$ are N, the other being CH;
$X^6$, $X^7$, $X^8$ and $X^9$ each independently are CH or N; provided that one or two of $X^6$, $X^7$, $X^8$ and $X^9$ are N, the other being CH;
$X^{10}$, $X^{11}$, $X^{12}$ and $X^{13}$ each independently are CH or N; provided that maximum one of $X^{10}$, $X^{11}$, $X^{12}$ and $X^{13}$ is N, the other being CH;
$X^{14}$ is CH or N;
$X^{15}$ is NH, O or S;
$X^{16}$ is CH or N;
$X^{17}$ is CH or N;
$X^{18}$ is NH, S or O;
$X^{19}$ is CH or N;
$X^{20}$ is NH or S;
$R^5$ and $R^6$ taken together form a bivalent radical —$R^5$-$R^6$—, having formula:

$$—(CH_2)_m—O—(CH_2)_{n-m}— \quad (a),$$

$$—(CH_2)_{n-m}—O—(CH_2)_m— \quad (b),$$

$$—(CH_2)_s— \quad (c), or$$

$$—CH=CH—CH=CH— \quad (d);$$

wherein the bivalent radical —$R^5$-$R^6$— may, where possible, be substituted with one or more substituents selected from the group consisting of halo, $C_{1-4}$alkyl, hydroxyl,
$C_{1-4}$alkyloxy and oxo;
m represents 0, 1 or 2;
n represents 2, 3 or 4;
s represents 3, 4 or 5;
wherein radicals (d-1)-(d-11) may be substituted with one or more substituents each independently selected from the group consisting of $C_{1-4}$alkyloxy, halo, $C_{1-4}$alkylcarbonyl, $C_{1-4}$alkylthio, $C_{1-4}$alkylsulphonyl, $C_{1-4}$alkylsulphinyl, and $C_{1-4}$alkyl optionally substituted with one or more halo substituents;
provided that radicals (d-1)-(d-11) are not substituted in the α-positions to the carbon atom of attachment;
or a pharmaceutically acceptable addition salt or a solvate thereof;
provided that the compound is not 5,6-dihydro-4-(2-pyridinyl)-4H-pyrrolo[1,2-a][1,4] benzodiazepine or a salt thereof, or 5,6-dihydro-4-(3-pyridinyl)-4H-pyrrolo[1,2,a][1,4] benzodiazepine or a salt thereof.

2. The compound according to claim 1 or a stereoisomeric form thereof, wherein,
$R^1$ is hydrogen, halo or $C_{1-4}$alkyl;
$R^2$ is hydrogen, halo or $C_{1-4}$alkyl;
$R^3$ and $R^4$ are hydrogen;
or $R^3$ and $R^4$ taken together form a bond;
Het is a monocyclic or bicyclic heterocyclic radical selected from (d-1), (d-2), (d-3), (d-4), (d-5), (d-8), (d-9), (d-10), (d-11) and (d-12);
(d-1) and (d-2) are attached to the remainder of the molecule with a bond in position a, b or c;
(d-4), (d-6), (d-7), (d-10) and (d-12) are attached to the remainder of the molecule with a bond in position a or b;
$X^1$ is O or NH;
$X^2$ is S;
$X^3$, $X^4$ and $X^5$ each independently are CH or N; provided that exactly two of $X^3$, $X^4$ and $X^5$ are N, the other being CH;
$X^6$, $X^7$, $X^8$ and $X^9$ each independently are CH or N; provided that one or two of $X^6$, $X^7$, $X^8$ and $X^9$ are N, the other being CH;
$X^{10}$, $X^{11}$, $X^{12}$ and $X^{13}$ each independently are CH or N; provided that maximum one of $X^{10}$, $X^{11}$, $X^{12}$ and $X^{13}$ is N, the other being CH;
$X^{14}$ is CH or N;
$X^{15}$ is O or S;
$X^{16}$ is CH or N;
$X^{17}$ is CH or N;
$X^{18}$ is NH, S or O;
$X^{19}$ is CH or N;

$X^{20}$ is NH or S;

$R^5$ and $R^6$ taken together form a bivalent radical —$R^5$-$R^6$—, having formula:

—(CH$_2$)$_s$—               (c), or

—CH═CH—CH═CH—        (d);

s represents 3, 4 or 5;

wherein radicals (d-1)-(d-5) and (d-8)-(d-11) may be substituted with one or more substituents each independently selected from the group consisting of $C_{1-4}$alkyloxy, halo, $C_{1-4}$alkylcarbonyl, and $C_{1-4}$alkyl optionally substituted with one or more halo substituents; provided that radicals (d-1)-(d-5) and (d-8)-(d-11) are not substituted in the α-positions to the carbon atom of attachment;

or a pharmaceutically acceptable addition salt or a solvate thereof.

3. The compound according to claim 1 wherein $R^3$ and $R^4$ are taken together to form a bond.

4. The compound according to claim 1 wherein wherein $R^1$ or $R^2$ is in the 7-position and is other than hydrogen.

5. The compound according to claim 1, wherein Het is selected from (d-3), (d-9) and (d-10);

wherein radicals (d-3), (d-9) and (d-10) may be substituted with one or more substituents each independently selected from the group consisting of $C_{1-4}$alkyloxy, halo, $C_{1-4}$alkylcarbonyl, $C_{1-4}$alkylthio, $C_{1-4}$alkylsulphonyl, $C_{1-4}$alkylsulphinyl, and $C_{1-4}$alkyl optionally substituted with one or more halo substituents; provided that radicals (d-3), (d-9) and (d-10) are not substituted in the a-positions to the carbon atom of attachment.

6. The compound according to claim 5, wherein Het is selected from (d-9) and (d-10);

wherein radicals (d-9) and (d-10) may be substituted with one or more substituents each independently selected from the group consisting of $C_{1-4}$alkyloxy, halo, $C_{1-4}$alkylcarbonyl, $C_{1-4}$alkylthio, $C_{1-4}$alkylsulphonyl, $C_{1-4}$alkylsulphinyl, and $C_{1-4}$alkyl optionally substituted with one or more halo substituents; provided that radicals (d-9) and (d-10) are not substituted in the α-positions to the carbon atom of attachment.

7. A pharmaceutical composition comprising a pharmaceutically acceptable carrier and, as active ingredient, a therapeutically effective amount of a compound as defined in claim 1.

8. A method for treating a patient suffering from a fungal infection, said method comprising administering to said patient a therapeutically effective amount of a compound of claim 1.

\* \* \* \* \*